(12) United States Patent
Golan et al.

(10) Patent No.: US 8,945,632 B2
(45) Date of Patent: Feb. 3, 2015

(54) METHODS AND COMPOSITIONS FOR INHIBITING THE NUCLEAR FACTOR κB PATHWAY

(75) Inventors: Avi Golan, Midreshet Ben Guirion (IL); Jacob Gopas, Beer Sheva (IL); Janet Ozer, Ashdod (IL); Nadav Eisner, Yeruham (IL); Adelbert Bacher, Garching (DE); Wolfgang Eisenreich, Freising (DE); Elena Ostrozhenkova, Jena (DE); Hila Winer, Raanana (IL)

(73) Assignees: Ben Gurion University of the Negev R&D Authority, Beer Sheva (IL); Mor Research Applications Ltd., Tel Aviv (IL)

( * ) Notice: Subject to any disclaimer, the term of this patent is extended or adjusted under 35 U.S.C. 154(b) by 0 days.

(21) Appl. No.: 13/810,668

(22) PCT Filed: Jul. 19, 2011

(86) PCT No.: PCT/IL2011/000576
§ 371 (c)(1),
(2), (4) Date: Jan. 17, 2013

(87) PCT Pub. No.: WO2012/011103
PCT Pub. Date: Jan. 26, 2012

(65) Prior Publication Data
US 2013/0122114 A1    May 16, 2013

Related U.S. Application Data

(60) Provisional application No. 61/365,380, filed on Jul. 19, 2010, provisional application No. 61/367,479, filed on Jul. 26, 2010, provisional application No. 61/377,988, filed on Aug. 30, 2010, provisional application No. 61/444,806, filed on Feb. 21, 2011.

(51) Int. Cl.
| | | |
|---|---|---|
| *A61K 31/24* | (2006.01) | |
| *A61K 31/44* | (2006.01) | |
| *A61K 31/70* | (2006.01) | |
| *A61K 31/438* | (2006.01) | |
| *A61K 31/4747* | (2006.01) | |
| *A61K 36/62* | (2006.01) | |
| *A61K 31/7048* | (2006.01) | |
| *A61K 33/24* | (2006.01) | |

(52) U.S. Cl.
CPC ........... *A61K 31/438* (2013.01); *A61K 31/4747* (2013.01); *A61K 36/62* (2013.01); *A61K 31/7048* (2013.01); *A61K 33/24* (2013.01)
USPC .............. 424/649; 514/278; 514/27; 435/375

(58) Field of Classification Search
CPC . A61K 36/62; A61K 424/649; A61K 514/27; A61K 514/278
USPC ..................................... 424/649; 514/27, 278
See application file for complete search history.

(56) References Cited

U.S. PATENT DOCUMENTS

| | | |
|---|---|---|
| 4,775,405 A | 10/1988 | Caulder et al. |
| 5,876,728 A | 3/1999 | Kass et al. |
| 2003/0180292 A1* | 9/2003 | Hanna et al. ............... 424/141.1 |
| 2007/0118916 A1 | 5/2007 | Puzio et al. |
| 2011/0182909 A1* | 7/2011 | Tidmarsh ................... 424/155.1 |

FOREIGN PATENT DOCUMENTS

| | | |
|---|---|---|
| JP | 2002/047146 | 2/2002 |
| JP | 2003252779 | 9/2003 |
| JP | 2005232039 | 9/2005 |

OTHER PUBLICATIONS

Ozer et al. (Cancer Biology &Therapy 8:19, 1860-1868 (2009).*
Titi Farmacia , (2009) 57(2) 141-156).*
McCutcheon Ethanopharmcology of Western North American Plants (1996).*
Binder Ann N Y Acad Sci. May 2009;1165:285-93.*
Ozer et al, Nuphar lutea thioalkaloids inhibit the nuclear factor κb pathway, potentiate apoptosis and are synergistic with cisplatin and etoposide, Cancer Biology & Therapy, 8:19, pp. 1860-1868, Oct. 1, 2009.
Matsuda, Nuphar alkaloids with immediately apoptosis-inducing activity from Nuphar pumilum and their structural requirements for the activity, Bioorganic & Medicinal Chemistry Letters 16, pp. 1567-1573, 2006.
International Search Report mailed on May 8, 2012 for International Application No. PCT/IL2011/000576.
Akinjogunla et al, Antimicrobial potential of *Nymphaea lotus* (Nymphaeaceae) against wound pathogens, Journal of Medicinal Plants Research, Mar. 2009, vol. 3(3), pp. 138-141.
Lohi et al, Antibacterial properties of *Nymphaea lotus* (Nymphaeaceae) tuber extract against clinical and phyto pathogens, Journal of Pharmacy Research, 2011, vol. 4(4), pp. 1231-1233.
Chauhan et al, Pharmacological evaluations for the antifertility effect of the ethanolic seed extract of *Nelumbo nucifera* (Sacred Lotus), Pharmacologyonline, 2009, vol. 2, pp. 636-643.

(Continued)

*Primary Examiner* — Shirley V Gembeh
(74) *Attorney, Agent, or Firm* — Pearl Cohen Zedek Latzer Baratz LLP

(57) ABSTRACT

The current invention provides therapeutic methods which include inhibition of nuclear factor κb pathway in a cell based on the discovery of an active fraction of a plant extract termed NUP or a composition which includes NUP. NUP is used in treating and managing different diseases such as cancer, inflammation, and virus infections.

17 Claims, 37 Drawing Sheets

(56) References Cited

OTHER PUBLICATIONS

Efferth, Natural products pave their way in cancer therapy, Cancer Biology & Therapy, Oct. 1, 2009, vol. 8, No. 19, pp. 1869-1870.
European Supplementary Search Report mailed on Dec. 2, 2013 for European application No. 11809371.5.
Yoshikawa et al., "Crude drugs from aquatic plants. VI. On the alkaloid constituents of Chinese *Nupharis rhizoma*, the dried rhizome of *Nuphar pumilum* (Timm.) DC. (Nymphaceae): structures and rearrangement reaction of thiohemiaminal type nuphar alkaloids", Heterocycles, International journal for reviews and communications in heterocyclic chemistry, Elsevier science publishers B.V. Amsterdam, NL, vol. 45, No. 9, pp. 1824-1915, Jan. 1, 1997.
Matsuda et al., "Dimeric Sesquiterpene Thioalkaloids with Potent Immunosuppressive Activity from the Rhizome of *Nuphar pumilum*: Structural Requirements of Nuphar Alkaloids for Immunosuppressive Activity", Bioorganic & Medicinal Chemistry, No. 9, pp. 1031-1035, 2001.
Wang et al., "NF-kappaB Signaling Pathway, Inflammation and Colorectal Cancer", Cellular & Molecular Immunology, vol. 6, No. 5, pp. 327-334, Oct. 2009.
Pasparakis et al., "IKK/NF-kappaB signaling in chronic inflammation", Cytokine, vol. 48, No. 11-12, 2009.

\* cited by examiner

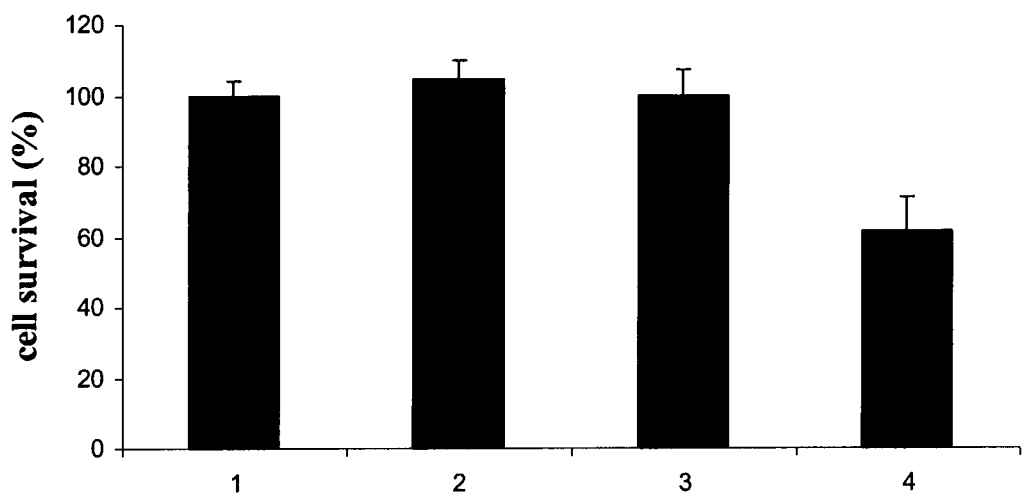
Figure 15B
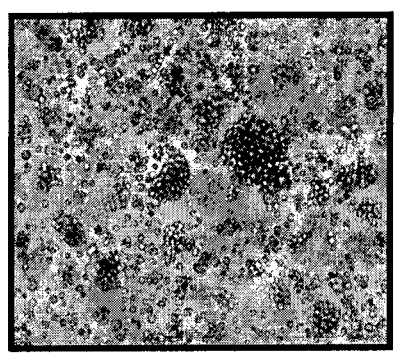 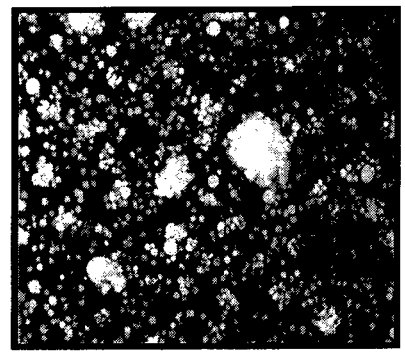
Figure 16A         Figure 16B

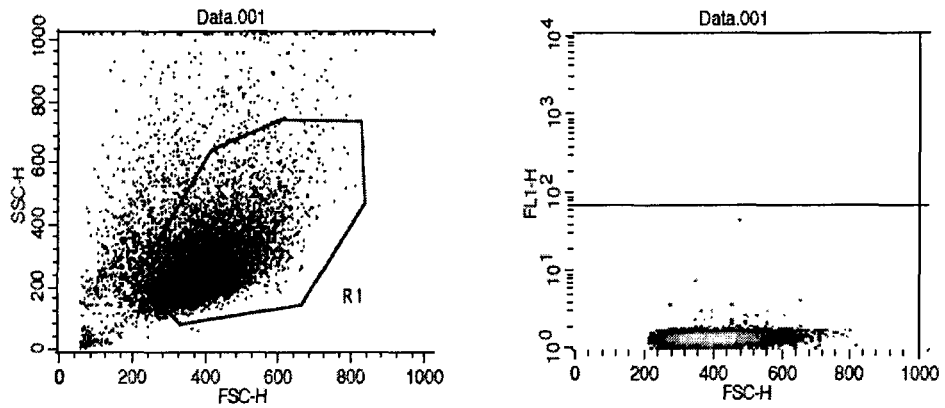
Quadrant Statistics
File: Data.001
Acquisition Date: 24-Jun-10
Gated Events: 9872
X Parameter: FSC-H (Linear)
Quad Location: 1001, 66
Log Data Units: Linear Values
Gate: G1
Total Events: 11426
Y Parameter: FL1-H (Log)
| Quad | Events | % Gated | % Total | X Mean | X Geo Mean | Y Mean | Y Geo Mean |
|---|---|---|---|---|---|---|---|
| UL | 0 | 0.00 | 0.00 | *** | *** | *** | *** |
| UR | 0 | 0.00 | 0.00 | *** | *** | *** | *** |
| LL | 9872 | 100.00 | 86.40 | 404.55 | 395.43 | 1.47 | 1.45 |
| LR | 0 | 0.00 | 0.00 | *** | *** | *** | *** |
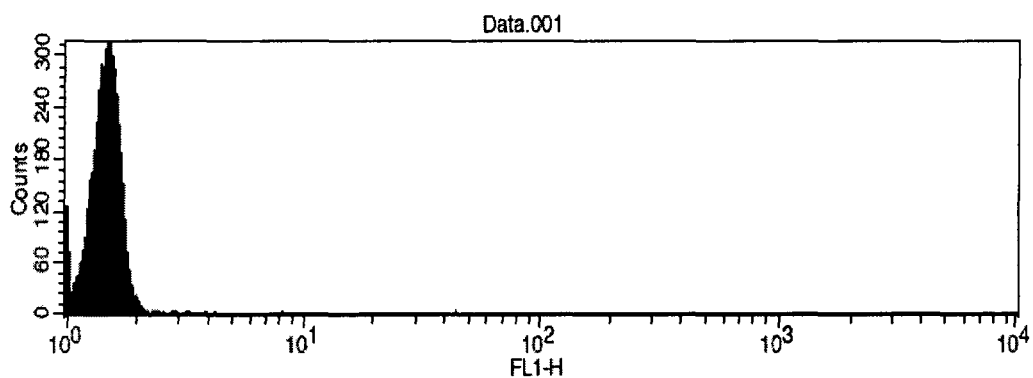
Figure 17A

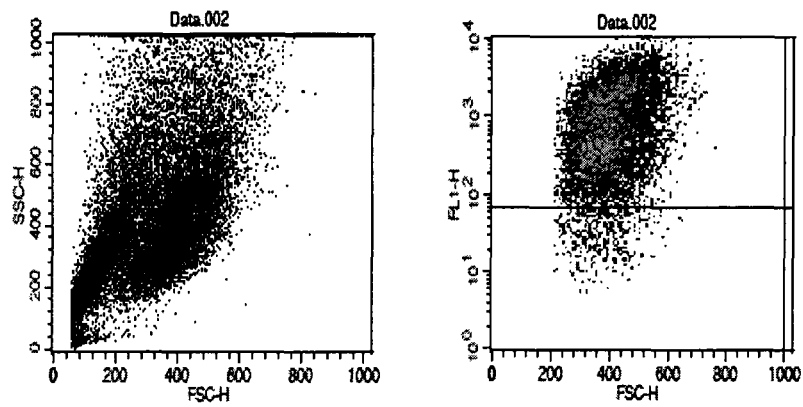
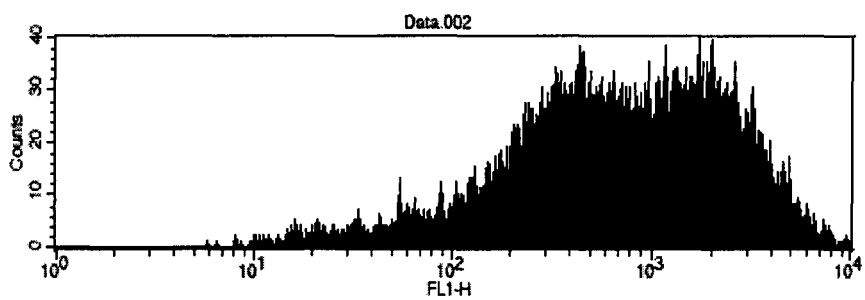
Figure 17B

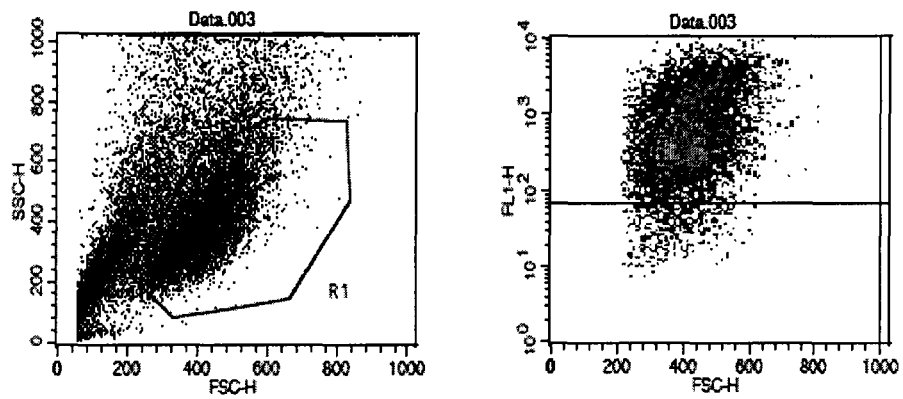
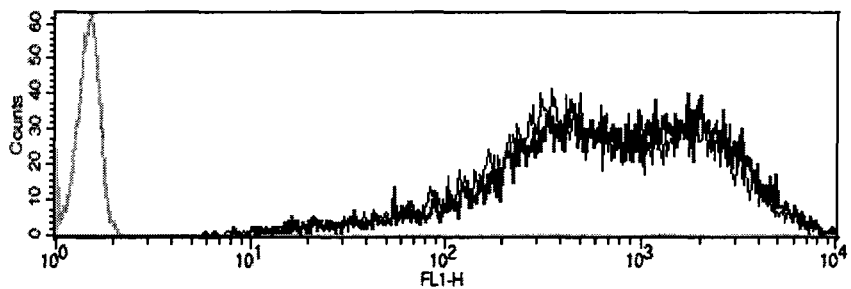
Figure 17C

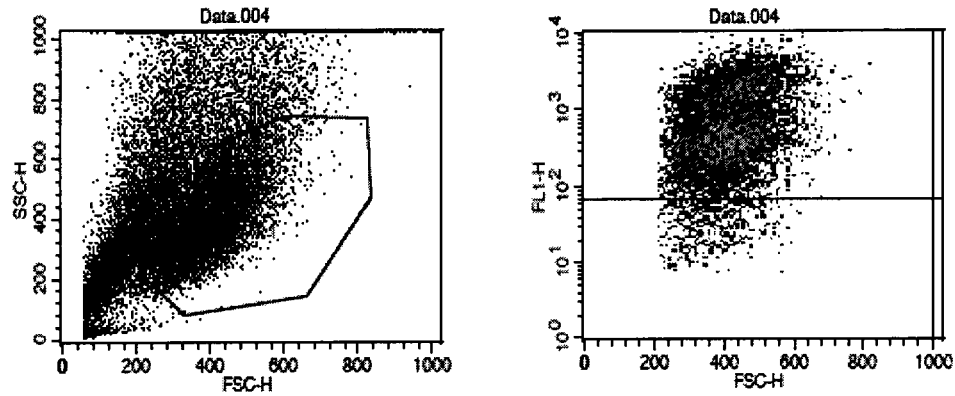
Quadrant Statistics
File: Data.004
Acquisition Date: 24-Jun-10
Gated Events: 9786
X Parameter: FSC-H (Linear)
Quad Location: 1001, 66
Log Data Units: Linear Values
Gate: G1
Total Events: 24430
Y Parameter: FL1-H (Log)
| Quad | Events | % Gated | % Total | X Mean | X Geo Mean | Y Mean | Y Geo Mean |
|---|---|---|---|---|---|---|---|
| UL | 9259 | 94.61 | 37.90 | 405.33 | 396.02 | 1030.56 | 631.19 |
| UR | 0 | 0.00 | 0.00 | *** | *** | *** | *** |
| LL | 527 | 5.39 | 2.16 | 361.20 | 352.19 | 36.92 | 32.53 |
| LR | 0 | 0.00 | 0.00 | *** | *** | *** | *** |
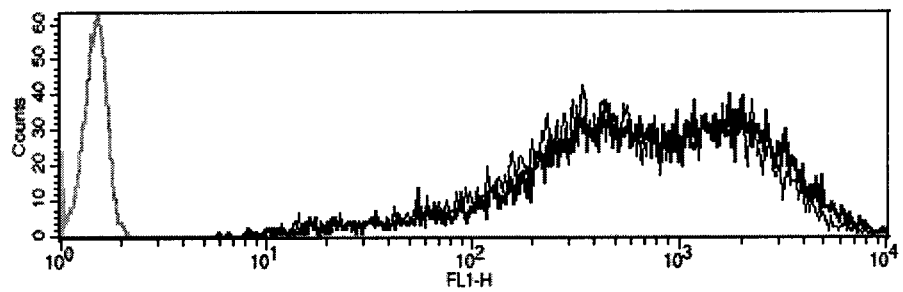
Figure 17D

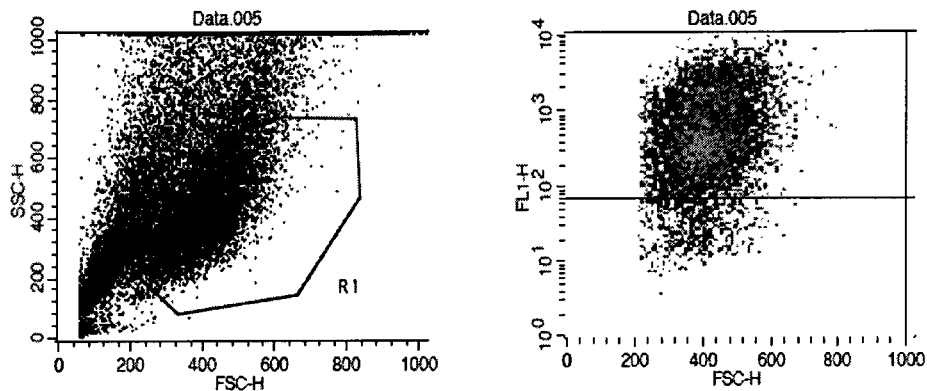
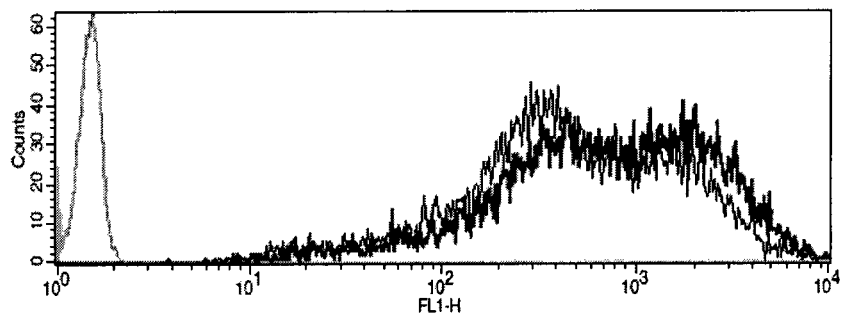
Figure 17E

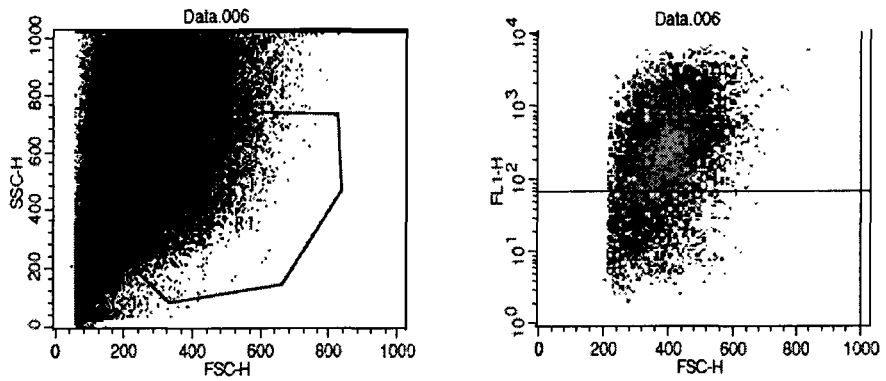
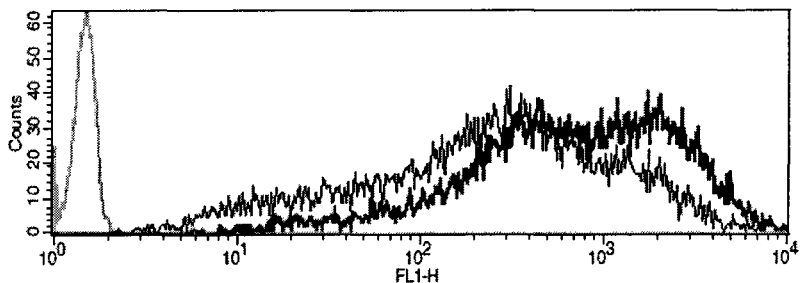
Figure 17F

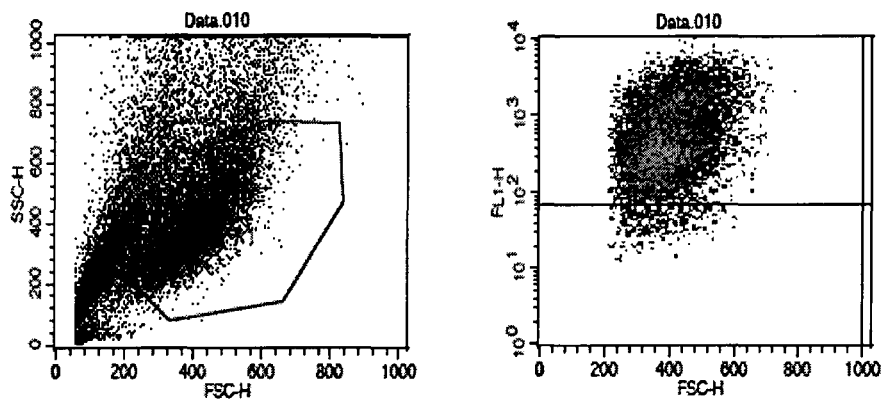
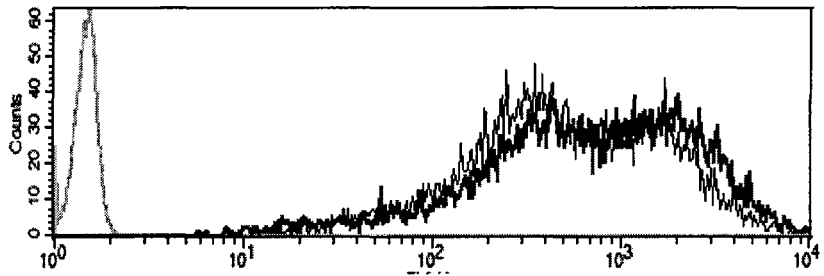
Figure 17G

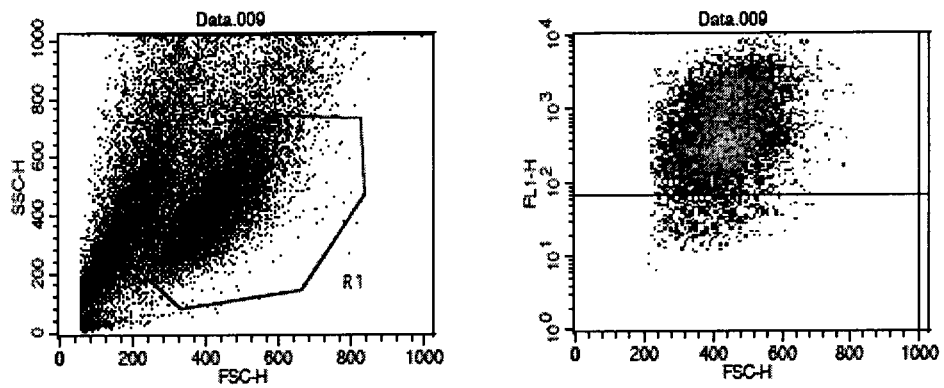
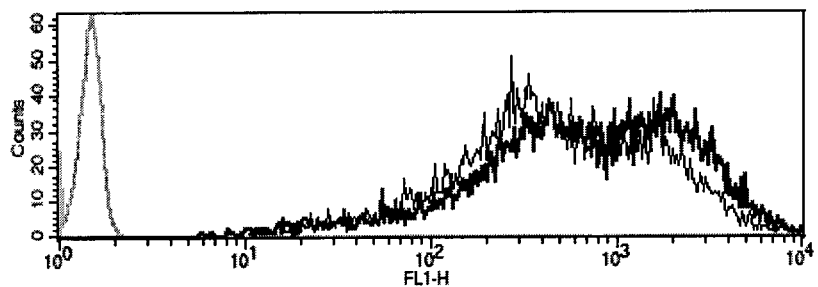
Figure 17H

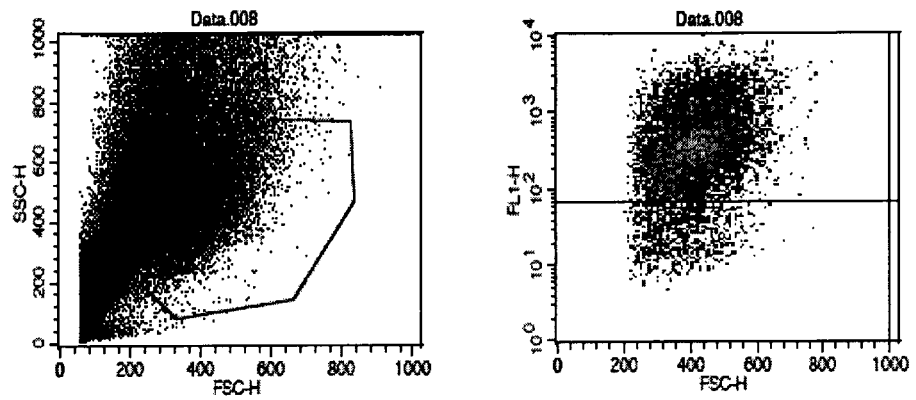
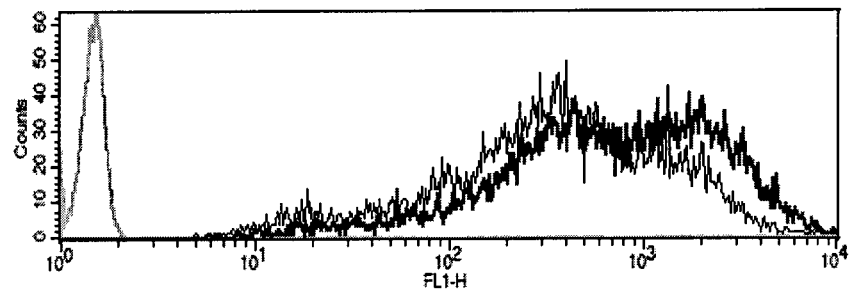
Figure 17I

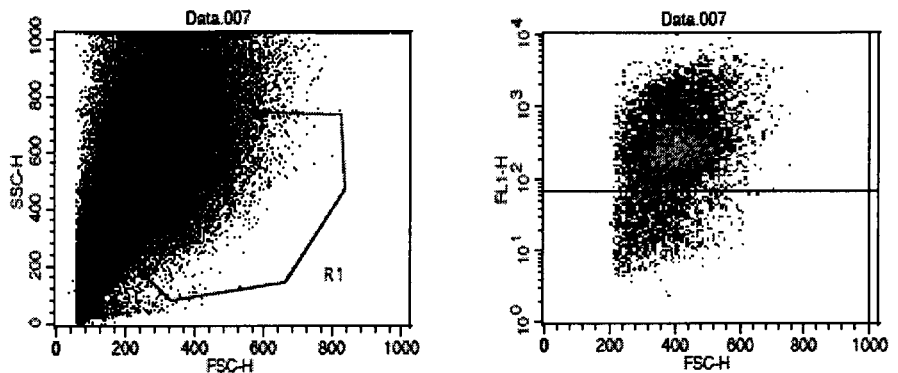
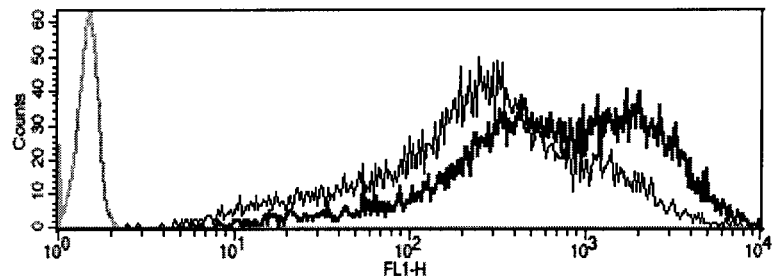
Figure 17J

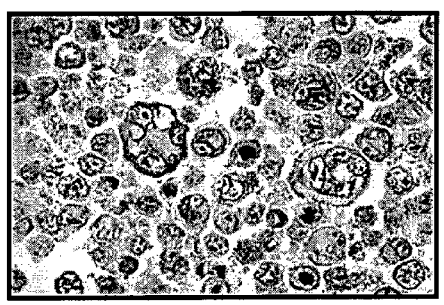
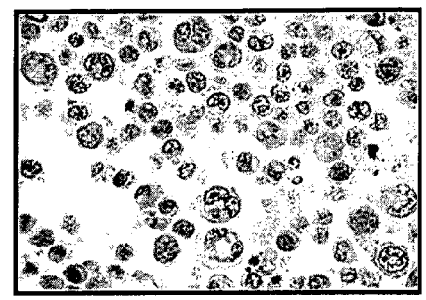
Figure 18A                    Figure 18B
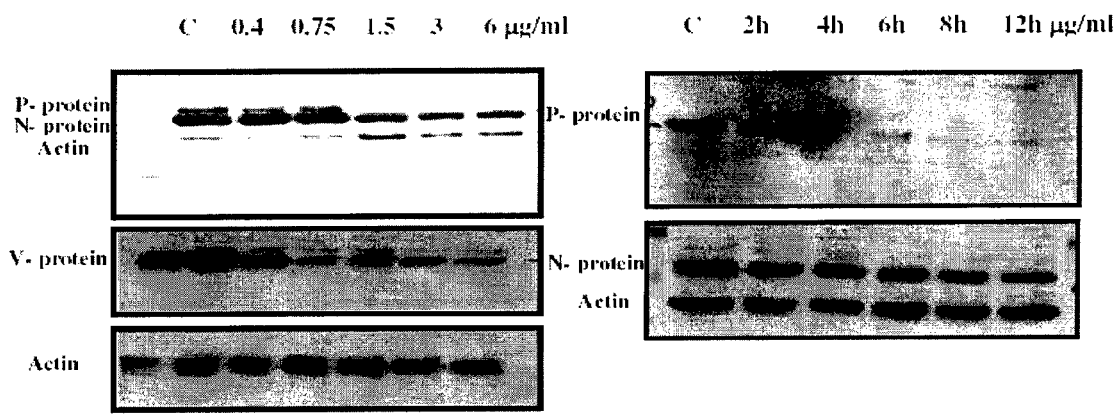
Figure 19A                                Figure 19B
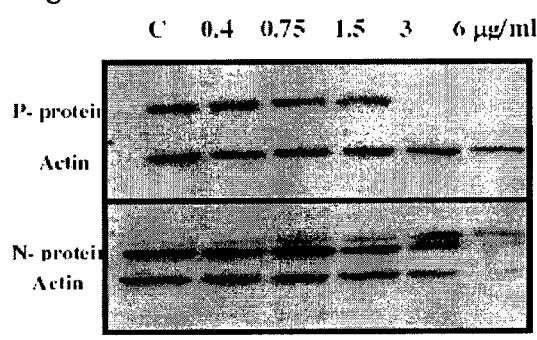
Figure 19C

X40

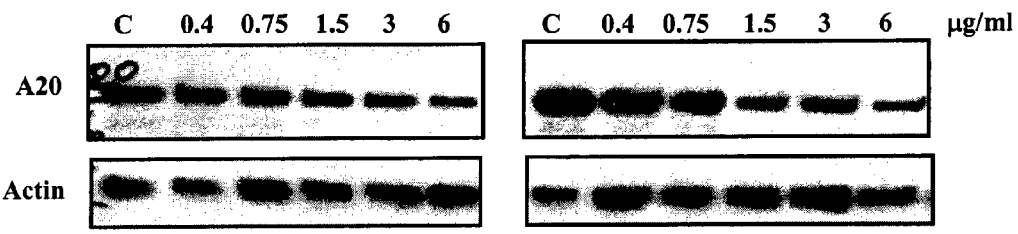
Figure 21A              Figure 21B
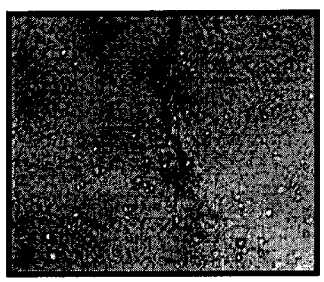 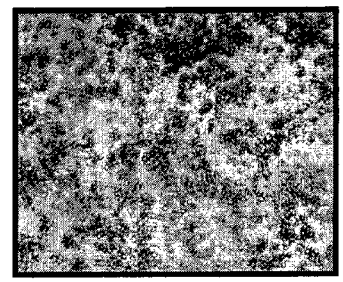 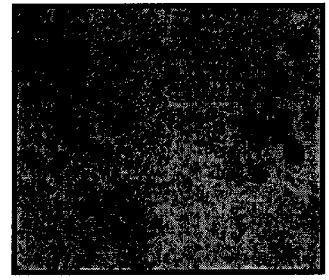
Figure 22A              Figure 22C              Figure 22E
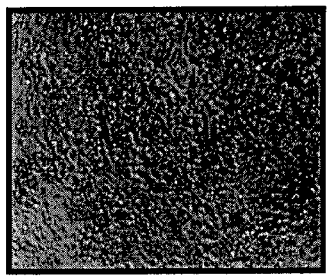 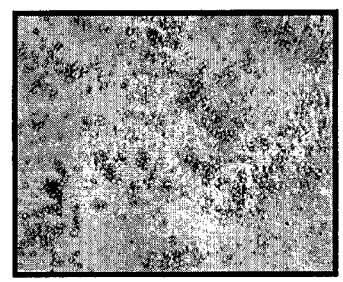 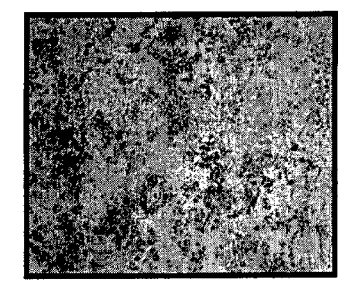
Figure 22B              Figure 22D              Figure 22F

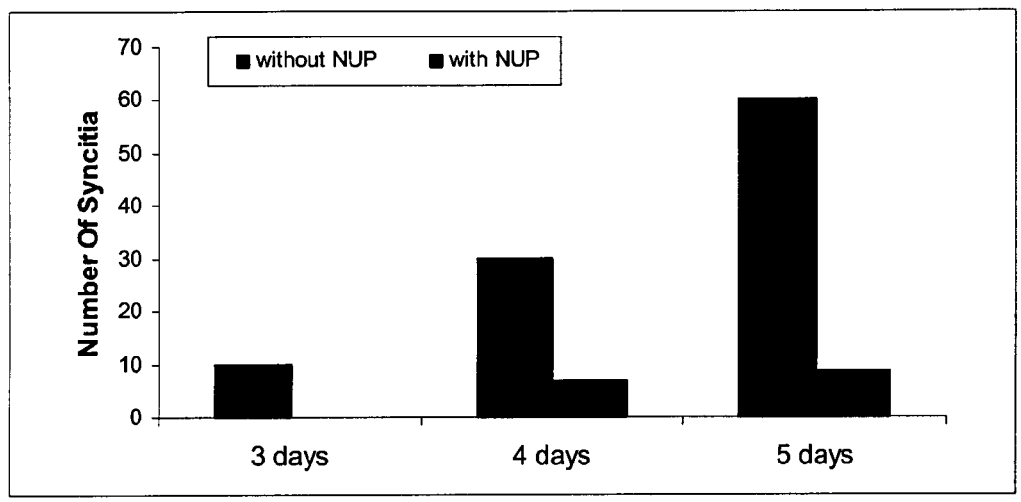
Figure 22G
 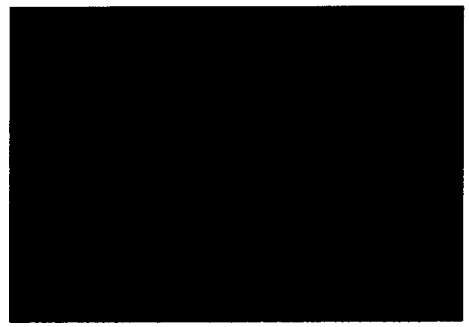
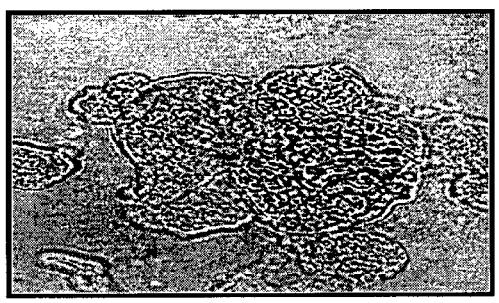 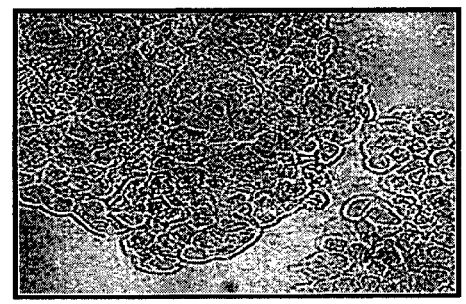
Figure 23A          Figure 23B

US 8,945,632 B2

METHODS AND COMPOSITIONS FOR INHIBITING THE NUCLEAR FACTOR κB PATHWAY

CROSS-REFERENCE TO RELATED APPLICATIONS

This application is a National Phase Application of PCT International Application No. PCT/IL2011/000576, International Filing Date Jul. 19, 2011, entitled "METHODS AND COMPOSITIONS FOR INHIBITING THE NUCLEAR FACTOR KB PATHWAY" published on Jan. 26, 2012, as International Publication No. WO 2012/011103, claiming priority of US Provisional Patent Applications No. 61/365,380, filed Jul. 19, 2010, U.S. Provisional Patent Application No. 61/367,479, filed Jul. 26, 2010, U.S. Provisional Patent Application No. 61/377,988 filed Aug. 30, 2010 and U.S. Provisional Patent Application No. 61/444,806 filed Feb. 21, 2011, which are incorporated herein by reference in their entireties.

FIELD OF INVENTION

The invention is directed to a composition comprising a Nymphaeaceae extract for inhibiting the nuclear factor κb pathway and for treating diseases.

BACKGROUND OF THE INVENTION

The NFκB family of transcription factors plays a pivotal role in inflammation and immune responses, proliferation, apoptosis and expression of certain viral genes. Therefore, the NFκB signaling pathway has also provided a focus for pharmacological intervention, primarily in chronic inflammation or in cancer, where the pathway is often constitutively active and plays a role in the disease.

The two most common pathways are the canonical (or classical) and the non-canonical (or alternative) pathways. A functional NFκB molecule is a heterodimer composed of members of the Rel family of proteins, which includes Rel A (p65), c-Rel, p50 in the classical pathway and Rel B and p52 in the alternative pathway. The major form of NFκB that is rapidly induced after stimulation is the Rel A/p50 complex. NFκB is maintained in an inactive form in the cytoplasm by IκB, which binds to NFκB and masks its nuclear localization signal.

There are several IκB proteins that are differentially regulated and have various affinities for individual NFκB complexes. IκBα is the best characterized. It is phosphorylated by the IκB kinase complex (IKK), resulting in its subsequent degradation by the proteasome and release of NFκB. NFκB is then able to translocate to the nucleus where it stimulates the transcription of a wide variety of genes, including cytokines, cell adhesion molecules and acute phase response proteins, which are involved in proliferation and survival as well as the inflammatory response. In the alternative pathway, activation of IKKα phosphorylates the NFκB precursor (p100) leading to its proteasomal processing and the formation of the active p52/Rel B heterodimer.

SUMMARY OF THE INVENTION

The invention provides a composition comprising NUP, wherein the NUP is a fraction of a Nymphaeaceae extract.

In another embodiment, the invention provides a method for inhibiting a nuclear factor κB pathway in a cell, comprising the step of contacting the cell with a composition comprising NUP. The invention further provides a method for treating a subject afflicted with Hodgkin lymphoma or melanoma or lung melanoma metastases comprising administering to the subject the composition comprising NUP.

In another embodiment, the invention provides a method for enhancing the efficacy of a composition comprising podophyllotoxin drug or a platinum drug, comprising the step of combining the composition comprising the podophyllotoxin drug or the platinum drug with the composition comprising NUP.

In another embodiment, the invention further provides a method for reducing or treating or preventing inflammation in a subject in need thereof, comprising administering to the subject the composition comprising NUP.

In another embodiment, the invention further provides a method for treating a subject afflicted with a paramyxovirus, such as without limitation, Respiratory Syncytial Virus, comprising the step of administering to the subject the composition comprising NUP.

In another embodiment, the invention further provides a method for reducing the contagiousness of a subject infected with or by a paramyxovirus, such as, without limitation, Respiratory Syncytial Virus, comprising the step of administering to the subject the composition comprising NUP.

BRIEF DESCRIPTION OF THE DRAWINGS

FIG. 16 depicts micrographs of cells persistently infected with MV-GFP. The cells were photographed under light (A) and Fluorescent microscope (B). All cells express the fluorescent virus with varying intensities FIG. 17 depicts graphs showing the results of fluorescence activated cell sorter (FACS) analysis (A) Non-infected control L428 cells (background fluorescence). (B) Control L428+MV-GFP without NUP. (C-F) L428+MV-GFP treated with 0.4, 0.75, 1.5 and 3 µg/ml NUP and incubated for 96 h. (G-J) L428+ incubated with 3 µg/ml NUP for 24, 48, 72 and 96 hours. Dark gray line represents the control L428 cells, light gray line represents the control L428+MV-GFP cells, black line—represents the NUP-treated sample.

FIG. 18 depicts immunohistochemical micrographs of L428 cells persistently infected (A) and not infected (B) with MV Edmonston strain and stained with anti protein P antibody.

FIG. 19 depicts gel micrographs of Western blot analysis performed on lysates from L428+MV or UKF (human neuroblastoma)+MV cells. Antibodies were against virus proteins: P-protein, N-protein and V-protein. (A) L428+MV cells were incubated either with different concentrations of NUP for 12 h, (B) with 3 µg/ml NUP for different times (C) UKF+ MV were incubated with different concentrations of NUP.

FIG. 21 depicts gel micrographs of Western blot analysis performed on lysates from L428+MV cells (A) or L428 cells free of MV (B). Antibodies were against host protein A20. Cells were incubated with different concentrations of NUP for 12 h.

FIG. 22A-F are micrographs showing the effect of RSV on Hep-2 cells with or without NUP. Hep-2 cells were infected with RSV strain A (dilution 1:10 from stock) and treated with 1.2 µg/ml NUP at either 2 h before infection, simultaneously or 2 h after infection. After 5 days syncitia was observed mainly in cells that were infected with RSV only. Cells that were treated with NUP either before, simultaneously or after infection did not create cyncitia (B and D); (A) represents cells without NUP or RSV; (C) represents cells with 1.2 mg/ml NUP; (E) represents RSV alone: (F) shows cells with RSV two hours before the administration of NUP. (G) is a bar graph showing the amount of syncitia that were created on day 3, 4 or 5 with or without NUP.

FIG. 23 depicts micrographs (bottom from light microscope; top from fluorescent microscope) showing Hep-2 cells that were persistently infected with RSV-strain A and stained with FITC N-protein antibodies: (A) RSV and (B) control cells.

DETAILED DESCRIPTION OF THE INVENTION

Figure 1:
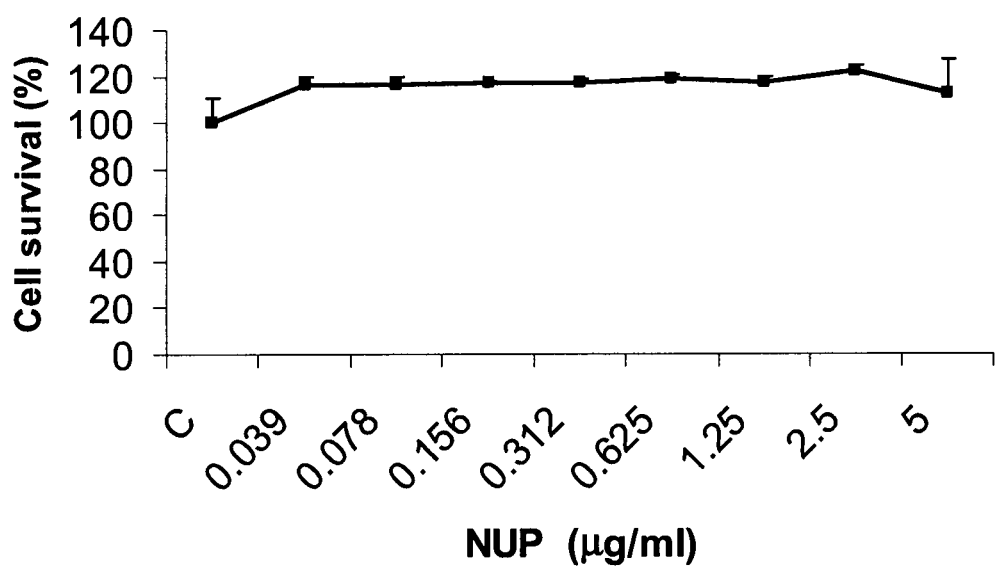
FIG. 1 is a graph showing the cytotoxicity of NUP. Hep-2 cells were incubated with different fractions of NUP) for 48 h to 5 days. Concentrations were diluted in the ratio of 1:2. After 12 to 5 days cell survival was examined with XTT assay. No cytotoxicity was observed at the conditions tested.

This invention provides, in one embodiment, a method of inhibiting a nuclear factor κB (NFκB) pathway in a cell, comprising the step of contacting the cell with a composition comprising NUP. In an embodiment of the invention, NUP comprises a compound represented by formula I:

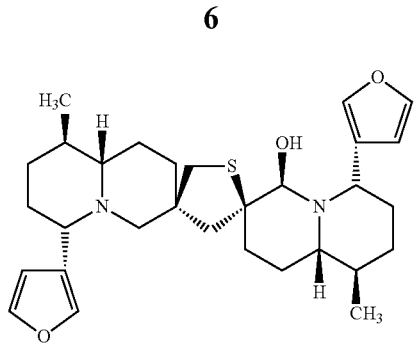

and a compound represented by formula II:

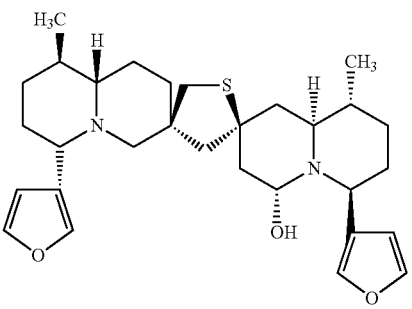

In an embodiment of the invention, the composition comprises a Nymphaeaceae extract. In some embodiments, Nymphaeaceae is a *Nuphar lutea*. In another embodiment, provided herein a method of inhibiting a nuclear factor κB (NFκB) pathway in a cell, comprising the step of contacting the cell with a composition comprising a fraction of Nymphaeaceae extract termed NUP. In an embodiment of the invention, the Nymphaeaceae extract is a *Nuphar lutea* extract. In another embodiment, NUP is a composition that inhibits NFκB in a NFκB luciferase reporter gene assay. In another embodiment, provided herein a method of inhibiting a nuclear factor κB (NFκB) pathway in a cell, comprising the step of contacting the cell with a composition comprising an alkaloid mixture extracted from *Nuphar lutea* which inhibits NF-κB termed NUP. In another embodiment, provided herein a method of inhibiting a nuclear factor κB (NFκB) pathway in a cell, comprising the step of contacting the cell with NUP, wherein NUP comprises at least two active compounds: 6-hydroxythiobinupharidine (formula I) and 6-hydroxythionuphlutine B (formula II).

In some embodiments, NUP and/or the compounds of formulas I and II induce cell arrest and/or apoptosis. In some embodiments, NUP and/or the compounds of formulas I and II induce cell arrest or apoptosis in a cancerous cell. In some embodiments, NUP and/or the compounds of formulas I and II inhibit metastasis. In some embodiments, NUP and/or the compounds of formulas I and II inhibit tumor growth. In some embodiments, NUP and/or the compounds of formulas I and II inhibit angiogenesis. In some embodiments, NUP and/or the compounds of formulas I and II inhibit cell cycle. In some embodiments, NUP and/or the compounds of formulas I and II inhibit aberrant cell cycle.

In some embodiments, inhibiting nuclear factor κB pathway according to the invention is independent of inhibiting IκB degradation. In some embodiments, inhibiting nuclear factor κB pathway according to the invention is by reducing the presence or the abundance of nuclear factor κB in a nucleus of a cell. In some embodiments, inhibiting nuclear factor κB pathway according to the invention occurs without increasing the presence of nuclear factor κB in a cytoplasm of a cell.

The inhibition of nuclear factor κB pathway according to the invention may involve inhibition of the expression of p65, p50, p52, Rel B, or any combination thereof. In some embodiments, inhibiting nuclear factor κB pathway is by inhibiting the canonical pathway, the alternative pathway, or a combination thereof.

In some embodiments, the cell is a neoplastic cell. In some embodiments, the neoplastic cell is a cancerous cell. In some embodiments, the neoplastic cell is a tumor cell. In some embodiments, the neoplastic cell is a metastatic cell. The neoplastic cell may be a neoplastic stem cell, a sarcoma cell, a lymphoma cell a Hodgkin lymphoma, a melanoma cell, a metastatic melanoma cell such as a melanoma cell in the lung, a carcinoma cell, a tumor germ cell, an Ewing's sarcoma cell, a lung cancer cell, a testicular cancer cell, a non-lymphocytic leukemia cell or a glioblastoma multiforme cell. The cell may be a eukaryotic cell, a eukaryotic cell infected with an oncogenic agent, a human cell or a cell is a pre-cancerous cell or any combination thereof.

In another embodiment, provided herein a method of treating a subject afflicted with a disease associated with aberrant activation of NF-κB, by administering to the subject an effective amount of a composition of the invention comprising an effective amount of NUP and/or the active pharmaceutical ingredients provided herein. In some embodiments, the composition of the invention may further comprise any drug intended to treat a disease characterized by aberrant activation of NF-κB.

In another embodiment, a disease characterized by aberrant activation of NF-κB is cancer. In some embodiments, NUP suppresses NF-κB pathways and limit the proliferation of cancer cells. In another embodiment, NUP suppresses NF-κB pathways and limit, prevent or treat an inflammatory response. In another embodiment, NUP and/or a combination of 6-hydroxythiobinupharidine (formula I) and 6-hydroxythionuphlutine B (formula II) suppress NF-κB pathways and is/are effective in the treatment of inflammatory diseases and/or viral diseases.

In another embodiment, provided herein a method of treating a subject afflicted with Hodgkin lymphoma or lung melanoma comprising administering to the subject a composition as described herein, thereby treating a subject afflicted with Hodgkin lymphoma or metastatic melanoma to the lung. In another embodiment, treating a subject afflicted with lung melanoma metastases according to the invention is inhibiting lung metastasis. In another embodiment, treating a subject afflicted with lung melanoma according to the invention is reducing lung metastasis. In another embodiment, provided herein a method of treating a subject afflicted with Hodgkin lymphoma or lung melanoma by inhibiting a nuclear factor κB pathway, comprising administering to the subject a composition as described herein. In another embodiment, provided herein a method of treating a subject afflicted with Hodgkin lymphoma or lung melanoma, comprising administering to the subject a composition as described herein, which comprises a combination of 6-hydroxythiobinupharidine (formula I), 6 hydroxythionuphlutine B (formula II) and a platinum drug and/or podophyllotoxin. In another embodiment, provided herein a method of treating a subject afflicted with Hodgkin lymphoma or lung melanoma, comprising administering to the subject a composition as described herein which comprises a combination of 6-hydroxythiobinupharidine (formula I), 6 hydroxythionuphlutine B (formula II) and cisplatin and/or etoposide.

In another embodiment, a method of treating a subject afflicted with lung melanoma comprises inhibiting metastasis. In another embodiment, a method of treating a subject afflicted with lung melanoma comprises reducing the number of lung metastatic nodules.

In another embodiment, provided herein a method for reducing inflammation in a subject comprising administering to the subject a composition as described herein which comprises a combination of 6-hydroxythiobinupharidine (formula I) and 6-hydroxythionuphlutine B (formula II). In another embodiment, provided herein a method for preventing inflammation in a subject comprising administering to a subject, having a risk of being afflicted with inflammation and/or having a risk associated with inflammation, a composition as described herein which comprises NUP or a combination of 6-hydroxythiobinupharidine (formula I) and 6-hydroxythionuphlutine B (formula II). In another embodiment, a subject having a risk associated with inflammation is a subject having a risk of being afflicted with a septic shock (example 8).

The term "reducing inflammation" refers herein to treating or preventing inflammation or reducing or ameliorating symptoms associated with inflammation. In another embodiment, reducing inflammation in a subject is preconditioning the subject with NUP thus reducing an anti-inflammatory response in two mechanisms: reduction/inhibition of pro-inflammatory agents and induction/elevation of anti-inflammatory agents. The inflammation may be an acute inflammation or a chronic inflammation.

In an embodiment of the invention the amount of NUP required for reducing inflammation and/or preventing inflammation is 1-100 mg/kg NUP per day. In another embodiment, the amount is 1-50 mg/kg NUP per day. In another embodiment, the amount is 1-10 mg/kg NUP per day. In another embodiment, the amount is 5-30 mg/kg NUP per day. In another embodiment, the amount is 7-25 mg/kg NUP per day.

The dosage may be at least once a day for at least one day, at least once a day for at least two days, at least once a day for at least three days, at least once a day for at least four days, at least once a day for at least one week or more.

The reducing of inflammation may include reducing the amount of pro-inflammatory cytokines such as TNF-α, IL-β, IL-6 and Interferon-γ in the blood and/or elevating the amount of anti-inflammatory cytokines, such as, IL-10 in the blood.

In another embodiment, a subject is a mammal. In another embodiment, a subject is a human. In another embodiment, a subject is a human suffering from a disease associated with overly active nuclear factor κB pathway. In another embodiment, a subject is a human suffering from cancer. In another embodiment, a subject is a lab animal, a rodent or a farm animal.

The invention is further related to the treatment of diseases that are associated or augmented by inflammation, bacterial translocation and or gut flora derangement, such as, for example, without being limited, chronic liver diseases and Alzheimer disease, hepatic encephalopathy, ADHD, metabolic syndrome, diabetes both type 1 and type 2, atherosclerosis or chronic fatigue syndrome, NASH, obesity, hepatic encephalopathy and potentially several immune mediated disorders among them Alopecia Areata, Lupus, Anlcylosing Spondylitis, Meniere's Disease, Antiphospholipid Syndrome, Mixed Connective Tissue Disease, Autoimmune Addison's Disease, Multiple Sclerosis, Autoimmune Hemolytic Anemia, Myasthenia Gravis, Autoimmune Hepatitis, Pemphigus Vulgaris, Behcet's Disease, Pernicious Anemia, Bullous Pemphigoid, Polyarthritis Nodosa, Cardiomyopathy, Polychondritis, Celiac Sprue-Dermatitis, Polyglandular Syndromes, Chronic Fatigue Syndrome (CFIDS), Polymyalgia Rheumatica, Chronic Inflammatory Demyelinating, Polymyositis and Dermatomyositis, Chronic Inflammatory Polyneuropathy, Primary Agammaglobulinemia, Churg-Strauss Syndrome, Primary Biliary Cirrhosis, Cicatricial Pemphigoid, Psoriasis, CREST Syndrome, Raynaud's Phenomenon, Cold Agglutinin Disease, Reiter's Syndrome, Crohn's Disease, Rheumatic Fever, Discoid Lupus, Rheumatoid Arthritis, Essential Mixed, Cryoglobulinemia Sarcoidosis, Fibromyalgia, Scleroderma, Grave's Disease, Sjogren's Syndrome, Guillain-Barre, Stiff-Man Syndrome, Hashimoto's Thyroiditis, Takayasu Arteritis, Idiopathic Pulmonary Fibrosis, Temporal Arteritis/Giant Cell Arteritis, Idiopathic Thrombocytopenia Purpura (ITP), Ulcerative Colitis, IgA Nephropathy, Uveitis, Insulin Dependent Diabetes (Type I), Vasculitis, Lichen Planus, and Vitiligo. The compositions described herein can be administered to a subject to treat or prevent disorders associated with an abnormal or unwanted immune response associated with cell, tissue or organ transplantation, e.g., renal, hepatic, and cardiac transplantation, e.g., graft versus host disease (GVHD), or to prevent allograft rejection.

In some embodiments of the invention, as can be seen from Examples, the inflammation is related to gastrointestinal inflammation, such as, inflammatory bowel disease (IBD), ulcerative colitis (UC) or Crohn's disease (CD).

In another embodiment, the phrases "inhibiting nuclear factor κB pathway" and "inhibiting" NFκB are used interchangeably. In another embodiment, inhibiting nuclear factor κB pathway comprises inhibiting the nuclear expression and/or limiting the nuclear presence of p65, p50, p52, Rel B, or any combination thereof. In another embodiment, nuclear factor κB pathway is the canonical pathway, the alternative pathway, or a combination thereof.

In another embodiment, provided herein a method for enhancing the efficacy of a composition comprising an anti-cancer drug such as podophyllotoxin drug such as etoposide or a platinum drug, or proteasome inhibitors such as bortezomib comprising the step of co-administering a composition comprising podophyllotoxin drug or a platinum drug or proteasome inhibitors or any combination thereof with a NUP or composition comprising NUP. The method for enhancing the efficacy yields a synergistic therapeutic, anti-cancer, effect, which require less amount of the podophyllotoxin drug or a platinum drug, or etoposide or bortezomib as shown in the experimental section.

"an anti-cancer drug" or "another anti-cancer drug" is a podophyllotoxin drug, such as, etoposide or teniposide or etopophos. In another embodiment, "an anti-cancer drug" or "another anti-cancer drug" is a platinum drug such as but not limited to: carboplatin, cisplatin, or oxaliplatin or proteasome inhibitor, such as without limitation, bortezomib. In another embodiment, provided herein a method of treating a subject afflicted with cancer comprising administering to the subject a composition comprising: (1) NUP comprising the combination of 6-hydroxythiobinupharidine (formula I) and 6-hydroxythiobinuphlutine B (formula II); and (2) another anti-cancer drug. In another embodiment, provided herein a method of treating a subject afflicted with cancer with a synergistic cancer treatment comprising the administration of: (1) NUP comprising the combination of 6-hydroxythiobinupharidine (formula I) and 6-hydroxythiobinuphlutine B (formula II); and (2) another anti-cancer drug.

In some embodiments, the cancer is Ewing's sarcoma, lung cancer, testicular cancer, lymphoma, non-lymphocytic leukemia, glioblastoma multiforme, sarcomas, carcinomas (such as: small cell lung cancer, and ovarian cancer), lymphomas, or germ cell tumors.

In another embodiment, treating a subject afflicted with cancer comprises inhibiting cancer spread to non-infected tissues. In another embodiment, treating a subject afflicted with cancer comprises ameliorating symptoms associated with cancer. In another embodiment, treating a subject afflicted with cancer comprises delaying the onset of the disease. In another embodiment, treating a subject afflicted with cancer comprises delaying the onset of symptoms associated with the disease.

In another embodiment, provided herein a method for treating a subject afflicted with a virus, such as paramyxovirus, which may be without limitation, measles, comprising the step of administering to the subject a composition comprising NUP as described herein. Further provided herein a method for inhibiting paramyxovirus epidemic, which may be without limitation, measles epidemic, comprising the step of administering to a subject afflicted with measles a composition comprising an effective amount of NUP or a composition comprising the same.

In another embodiment, provided herein a method for inhibiting measles epidemic, comprising the step of administering to all subjects living in proximity to and/or in contact with a subject afflicted with measles a composition comprising an effective amount of NUP or a composition comprising the same. In another embodiment, provided herein a method of preventing a cytotoxic effect of a measles virus in a subject, comprising the step of administering to the subject NUP or a composition comprising the same.

In another embodiment, the subject is at risk of acquiring a measles virus.

In another embodiment, provided herein a method of reducing the contagiousness of a subject infected by a paramyxovirus, which may be without limitation, measles virus, comprising the step of administering to the NUP or a composition comprising the same.

In another embodiment, reducing the contagiousness of a subject infected by a paramyxovirus, which may be without limitation, measles virus, is inhibiting an expression of a measles virus N-protein, V-protein, P-protein, or any combination thereof in a mucus cell, which is for example, in the respiratory system, nose or mouth.

In another embodiment, a subject afflicted with measles is a subject infected with measles virus. In some embodiments, a subject infected with measles virus but free of symptoms associated with measles. In some embodiments, the subject is a subject infected with measles virus and suffering from symptoms associated with measles. In another embodiment, a subject infected with measles virus in the infectivity period. The subject may be a subject that was not immunized against measles virus, an infant, an infant younger than 12 months old, a pregnant woman, a subject afflicted with an immune disease or a subject is a subject afflicted with AIDS and/or HIV.

In another embodiment, treating a subject afflicted with measles comprises inhibiting measles virus spread to non-infected cells. In another embodiment, treating a subject afflicted with measles comprises inhibiting the contagiousness of the subject. In another embodiment, treating a subject afflicted with measles comprises inhibiting measles spread from the subject to other subjects.

In another embodiment, treating a subject afflicted with measles comprises reducing the risk of complications associated with measles. In another embodiment, complications associated with measles include but are not limited to ear infection, Bronchitis, laryngitis or croup, inflammation of the larynx, inflammation of the bronchial tubes, pneumonia, encephalitis, miscarriage, premature labor, thrombocytopenia, or any combination thereof.

In some embodiments, provided herein a method for treating a subject afflicted with Respiratory Syncytial Virus (RSV), comprising the step of administering to the subject an effective amount of NUP or a composition comprising NUP. Further, provided herein a method for inhibiting RSV epidemic, comprising the step of administering to a subject afflicted with RSV an effective amount of NUP or a composition comprising NUP.

In some embodiments, provided herein a method for inhibiting RSV epidemic, comprising the step of administering to all subjects living in proximity to and/or in contact with a subject afflicted with RSV, NUP or a composition comprising NUP. In another embodiment, provided herein a method of preventing a cytotoxic effect of a Respiratory Syncytial Virus in a subject, comprising the step of administering to the subject of NUP or a composition comprising NUP. In some embodiments, the subject is infected by a RSV. In another embodiment, the subject is free of a RSV.

In some embodiments, the subject is at risk of acquiring a RSV. In another embodiment, provided herein a method of reducing the contagiousness of a subject infected with RSV, comprising the step of administering to the subject of NUP or a composition comprising NUP.

In some embodiments, reducing the contagiousness of a subject infected by a RSV is inhibiting an expression of a RSV N-protein, V-protein, P-protein, or any combination thereof in a mucus cell.

In another embodiment, reducing the contagiousness of a subject infected by a RSV is inhibiting lysis in a RSV infected mucus cell that may be in the respiratory system.

In another embodiment, a subject infected with RSV but free of symptoms associated with RSV. In another embodiment, a subject infected with RSV and suffering from symptoms associated with RSV. In another embodiment, a subject infected with RSV in the infectivity period.

In some embodiments, a subject is a subject that was not immunized against RSV. The subject may be an infant, an infant younger than 12 months old, a pregnant woman, a subject is a subject afflicted with an immune disease, a subject suffering from a compromised immune system or a subject is a subject afflicted with AIDS and/or HIV.

In some embodiments, a cell is a cell infected by a RSV. In some embodiments, a cell is a eukaryotic cell and may be a eukaryotic cell infected by a RSV. In another embodiment, a cell is a human cell. In another embodiment, a cell is a human cell infected by a RSV. In another embodiment, a cell is a mucus cell. In another embodiment, a subject infected with RSV is a subject free of symptoms associated with RSV. In another embodiment, a subject afflicted with RSV is a subject infected with RSV and suffering from symptoms associated with RSV. In another embodiment, a subject afflicted with RSV is a subject infected with RSV in the infectivity period.

In another embodiment, treating a subject afflicted with RSV comprises inhibiting RSV spread to non-infected cells. In another embodiment, treating a subject afflicted with RSV comprises inhibiting RSV spread to non-infected mucus cells. In another embodiment, treating a subject afflicted with RSV comprises inhibiting RSV spread to non-infected respiratory mucus cells. In another embodiment, treating a subject afflicted with RSV comprises inhibiting RSV protein assembly within infected cells. In another embodiment, treating a subject afflicted with RSV comprises ameliorating symptoms associated with RSV infection. In another embodiment, treating a subject afflicted with RSV comprises inhibiting the incubation period of the RSV. In another embodiment, treating a subject afflicted with RSV comprises prolonging the incubation period of the RSV.

In another embodiment, treating a subject afflicted with RSV comprises delaying the contagious phase of the disease. In another embodiment, treating a subject afflicted with RSV according to the invention is inhibiting a RSV epidemic. In another embodiment, treating a subject afflicted with RSV according to the invention, is delaying symptoms or complications associated with RSV infection. In another embodiment, treating a subject afflicted with RSV according to the invention, is evading symptoms or complications associated with RSV infection. In another embodiment, treating a subject afflicted with RSV according to the invention, is inhibiting symptoms or complications associated with RSV infection. In another embodiment, treating a subject afflicted with RSV is shortening the infective period. In another embodiment, treating a subject afflicted with RSV is shortening onset of disease/symptoms caused by RSV.

The treatment may facilitate symptoms associated with RSV including but not limited to: lungs infection, breathing passages infection, respiratory illness, common cold, bronchiolitis, pneumonia, stuffy or runny nose, sore throat, mild headache, cough, fever, and a general feeling of being ill.

In another embodiment, treating a subject afflicted with RSV comprises reducing the risk of complications associated with RSV, such as, severe breathing problems that need to be managed in the hospital, bronchiolitis, or pneumonia.

Both measles and RSV exemplified in the application are paramyxoviruses. Paramyxoviruses include mumps, measles, and respiratory syncytial virus (RSV), which is the major cause of bronchiolitis and pneumonia in infants, children and the elderly. The genome of these viruses is (−) RNA.

Accordingly, the invention provides a method of treating a subject afflicted with a disease caused by a paramyxovirus, comprising the step of administering to the subject an effective amount of NUP or a composition comprising NUP.

Composition

In an embodiment of the invention, there is provided a composition comprising NUP which comprises a mixture of a compound represented by formula I and a compound represented by formula II. In another embodiment, NUP is a purified Nymphaeaceae extract, which may be a *Nuphar lutea* (*N. lutea*)) extract. The NUP comprises, in an embodiment of the invention, thioalkaloids. In some embodiments, NUP is a purified plant extract composition comprising the compounds of formula I and formula II and thioalkaloids.

In another embodiment, a composition of the invention is an anti-cancer composition comprising an alkaloid mixture extracted from *Nuphar lutea*.) In another embodiment, a composition of the invention comprises dimeric sesquiterpene thioalkaloids. In another embodiment, a composition of the invention comprises thionupharidines and thionuphlutidines.

In another embodiment, a composition as described herein comprises a platinum drug and NUP. In another embodiment, a composition as described herein comprises a platinum drug and at least 6-hydroxythiobinupharidine (formula I) and 6-hydroxythionuphlutine B (formula II). In another embodiment, a composition as described herein comprises cisplatin and NUP or at least 6-hydroxythiobinupharidine (formula I) and 6-hydroxythionuphlutine B (formula II). In another embodiment, a composition as described herein comprises a podophyllotoxin drug and NUP or at at least 6-hydroxythiobinupharidine (formula I) and 6-hydroxythionuphlutine B (formula II). In another embodiment, a composition as described herein comprises etoposide and NUP or at least 6-hydroxythiobinupharidine (formula I) and 6-hydroxythionuphlutine B (formula II). In another embodiment, a composition as described herein is a synergistic pharmaceutical composition.

In another embodiment, the methods as described herein comprise continuous administration of the composition as described herein to the subject. The methods as described herein comprise administering the composition as described herein to the subject for at least one week, two weeks, a month, six months, a year or more than a year.

The Extract

In another embodiment, NUP is a purified fraction of a Nymphaeaceae extract having a biological activity as described herein. In another embodiment, NUP is a purified fraction of a *Nuphar lutea* L. extract having a biological activity as described herein.

Process of Obtaining NUP

NUP (Step I)

In another embodiment, NUP is prepared from *Nuphar lutea* L. In one embodiment, a plant structure such as a leaf (floating and submerged) of *Nuphar lutea* L. are oven-dried at 60-90° C., and ground. The grinding may be preformed in a mortar and pestle. In another embodiment, the ground oven-dried plant structure such as a leaf is extracted in an alcohol such as but not limited to methanol in a weight (gr) per volume (ml) ratio of 1-4 to 1-20. In another embodiment, 50 grams of dry leaf powder is extracted in 400 ml methanol. The extraction may last two hours or more. In another embodiment, extraction is preformed for at least 4 hours. In another embodiment, extraction is preformed while stirring the mixture. In The extraction typically results in a mixed slurry, which may be separated by centrifugation to obtain a pellet. In another embodiment, the mixed slurry is centrifuged at 5,000-20000 rpm, 1-10° C. for 5-120 minutes. In another embodiment, the pellet is discarded. In another embodiment, the supernatant is filtered thus obtaining a clean or pure extract.

NUP (Step III)

In another embodiment, the NUP containing composition is present within the solvent-alcohol fraction. In another embodiment, the solvent-alcohol is separated from the extract by means known to one of skill in the art, such as, but not limited to, evaporation. In another embodiment, the extract IS evaporated under reduced pressure on a rotary-evaporator at 25-50° C. In another embodiment, the extract is evaporated under reduced pressure on a rotary-evaporator at 40° C.

NUP (Step IV)

In another embodiment, the residue (it is part of the extract obtained after evaporation of the alcohol) is further purified and/or cleaned by dissolving it in a mixture of acid and a non-polar lipophilic organic solvent. In another embodiment, the un-wanted fraction of the residue is soluble in a non-polar lipophilic organic solvent. In another embodiment, this step further purifies the NUP comprising composition/residue by discarding a fraction of the residue which is soluble in a non-polar lipophilic organic solvent such as chloroform. In another embodiment, the residue is further purified and/or cleaned by dissolving it in a mixture of a polar solvent and a non-polar lipophilic organic solvent (1:1, v/v). In another embodiment, the residue contains un-wanted residues that are soluble in a non-polar lipophilic organic solvent such as chloroform. In another embodiment, this step reduces an unwanted fraction of the residue which is soluble in non-a polar lipophilic organic solvent such as chloroform. In another embodiment, the residue is dissolved in at least 50 ml of a mixture containing acid and a non-polar lipophilic organic solvent (1:1, v/v). In another embodiment, the residue is dissolved in a mixture consisting 1N HCl and chloroform (1:1, v/v) and then transferred to a separatory-funnel, mixed well and let stand for approx. 0.5-2 hours. In another embodiment, the residue comprising NUP is present in the polar fraction (acid fraction). NUP (step V)

In another embodiment, NUP is further purified from the acid and NUP comprising fraction by the addition of a base. In another embodiment, NUP is purified by the addition of a weak base. In another embodiment, NUP is purified from the acid and NUP comprising fraction by the addition of 25% NH$_4$OH until pH 8-10 is reached. In another embodiment, NUP is purified from the acid and NUP comprising fraction by the addition of 25% NH$_4$OH until pH 9 is reached. In another embodiment, NUP is further purified by adjusting the pH of NUP and acid comprising fraction to pH 8-10 and results in the formation of a precipitate which comprises NUP. In another embodiment, the precipitate that is formed is harvested by centrifugation. In another embodiment, the precipitate is soluble in alcohol. In another embodiment, the precipitate is soluble in 50% water/methanol (or ethanol) mixture.

NUP (Step VI)

In another embodiment, the precipitate is further purified by dissolving it in 50% water/methanol (or ethanol) mixture. In another embodiment, the composition comprising NUP, alcohol, and water is adjusted to pH 1-3. In another embodiment, the composition comprising NUP, alcohol, and water is adjusted to pH 2 for better solubilization and then to pH 8-10 by the use of a base such as without limitation 25% NH$_4$OH. In another embodiment, the composition comprising NUP, alcohol, and water is adjusted to pH 2 for better solubilization and then adjusted to pH 9.

NUP (Step VII)

In another embodiment, the composition comprising NUP, alcohol, and water is adjusted to pH 8-10 resulting in a further purified precipitate which comprises NUP. In another embodiment, the precipitate is harvested by centrifugation.

NUP (Step VIII)

In another embodiment, the precipitate is further purified by dissolving it. In another embodiment, the precipitate is further purified by dissolving it in an alcohol. In another embodiment, NUP is further purified by dissolving the precipitate in alcohol such as: 50% water/methanol (or ethanol) mixture, and then the solution/composition comprising NUP is adjusted to pH 2-6. In another embodiment, the solution/composition comprising NUP is adjusted to pH 3-5. In another embodiment, the solution/composition comprising NUP is adjusting the pH 4. In another embodiment, adjusting to acidic pH comprises the addition of acid. In another embodiment, adjusting to acidic pH comprises the addition of 1N HCl.

In another embodiment, the solution/composition comprising NUP and having an acidic pH is kept for at least 5 minutes in room temperature. In another embodiment, the solution/composition comprising NUP and having an acidic pH is kept for at least 20 minutes in a temperature below 20° C. but above 1° C. In another embodiment, the solution/composition comprising NUP and having an acidic pH is kept for at least 30 minutes in a temperature below 10° C. but above 1° C. In another embodiment, the solution/composition comprising NUP and having an acidic pH is kept for at least 40 minutes in a temperature below 5° C. but above 1° C.

Then, in another embodiment, the solution/composition comprising NUP is centrifuged and the yellowish supernatant obtained contained dry matter.

In another embodiment, steps I-VII comprise a process for purifying NUP, comprising the following consecutive steps: obtaining a dried and ground Nymphaeaceae such as *Nuphar lutea* L. organ; extracting the dried and ground *Nuphar lutea* L. organ in a solvent such as an alcohol and obtaining a mixed slurry; separating the plant extract present in the solvent such as alcohol from the mixed slurry; discarding the alcohol from the extract and obtaining a residue; dissolving the residue in a dual fraction composition composed of an acid and a non-polar lipophilic organic solvent and discarding the non-polar lipophilic organic solvent fraction; obtaining a precipitate by adjusting the pH of the acid comprising fraction to pH 8-10; isolating the precipitate; dissolving the precipitate in a composition comprising alcohol and having pH 2-6; obtaining a second precipitate by adjusting the pH of the solution to pH 8-10; isolating the second precipitate; dissolving the second precipitate in a composition comprising alcohol and having pH 2-6; separating the supernatant from the solution; and isolating the dry matter present in the supernatant. In another embodiment, the dry matter present in the supernatant is NUP. In another embodiment, the dry matter present in the supernatant is NUP purified from a plant organ. In another embodiment, the dry matter present in the supernatant is NUP having the biological activity as described herein.

The organ derived from the plant is a leaf, a shoot, a stem, a plant tissue or a reproductive organ or a vegetative organ.

In another embodiment, methods for drying a plant organ such as a leaf are known to one of skill in the art and include but are not limited to oven drying.

In another embodiment, methods for obtaining a dual fraction composition composed of an acid and a non-polar lipophilic organic solvent are known to one of skill in the art. In another embodiment, a separatory-funnel is used for obtaining a dual fraction composition composed of an acid and a non-polar lipophilic organic solvent. In another embodiment, methods for isolating or purifying a precipitate such as centrifugation or evaporation are known to one of skill in the art. In another embodiment, methods for separating a solution to at least two fractions or phases including a supernatant fraction or phase are known to one of skill in the art. In another embodiment, methods for separating a solution to at least two fractions or phases including a supernatant fraction or phase include but are not limited to: centrifugation. In another embodiment, discarding the alcohol from the extract and obtaining a residue is preformed by centrifugation and/or evaporation.

In another embodiment, NUP as described herein comprises a fraction of a *Nuphar lutea* L. extract having an unexpected therapeutic activity. In another embodiment, NUP is prepared from a dried *Nuphar*. In another embodiment, a NUP extract is prepared from a dried *Nuphar* rhizome. In another embodiment, dried is oven dried or any other method of drying a plant or a plant organ known to one of skill in the art. In another embodiment, *Nuphar* leaf or rhizome is oven-dried at 70° C. In another embodiment, the dried *Nuphar* rhizome is grinded in a mortar. In another embodiment, the dry plant powder is extracted in a solvent such as but not limited to methanol. In another embodiment, a liquid extract of *Nuphar* leaf or rhizome in a solvent is obtained and the solvent is evaporated under reduced pressure and then dissolved in 100 ml of a mixture of 1N HCl and chloroform (1:1, v/v). In another embodiment, the aqueous phase is separated and adjusted to pH 9 by the addition of 25% $NH_4OH$. In another embodiment, the obtained precipitate is harvested by centrifugation, dissolved in acidic methanol (the process of re-solubilization in acidic aqueous methanol and precipitation in 25% $NH_4OH$ at pH 9 is repeated twice and precipitate is resolubilized in acidic aqueous methanol or ethanol at a concentration of 10 mg/ml (gravimetrically) and used as NUP), and placed on a silica gel column that is developed with a mixture of chloroform/ethyl-acetate/diethylamine (20:1:1, v/v/v). In another embodiment, the fractions are monitored for reducing/inhibiting NFκB activity via the NFκB luciferase reporter gene assay. In another embodiment, the active fractions are combined and evaporated to dryness under reduced pressure. In another embodiment, the residue of the active fractions is dissolved in 50% methanol or ethanol in water and used in the following experiments.

In another embodiment, an effective amount of a compound of NUP is between about 0.2 to 500 mg/kg/day of body weight. In another embodiment, an effective amount of a a compound of NUP as described herein is between about 20 to 500 mg/kg/day of body weight. In another embodiment, an effective amount of NUP as described herein is between about 30 to 250 mg/kg/day of body weight. In another embodiment, an effective amount of NUP as described herein is between about 50 to 150 mg/kg/day of body weight.

In another embodiment, an effective amount of a compound of formula II is between about 0.2 to 500 mg/kg/day of body weight. In another embodiment, an effective amount of a compound of formula II as described herein is between about 20 to 500 mg/kg/day of body weight. In another embodiment, an effective amount of a compound of formula II as described herein is between about 30 to 250 mg/kg/day of body weight. In another embodiment, an effective amount of a compound of formula II as described herein is between about 50 to 150 mg/kg/day of body weight.

In some embodiments, a compound of formula I, a compound of formula II, or both are chemically synthesized such as by using standard techniques. In some embodiments, these chemical methods include exclusive solid phase synthesis, partial solid phase synthesis, fragment condensation, or classical solution synthesis.

The composition as described herein is a "pharmaceutical composition". In another embodiment, a "pharmaceutical composition" refers to a preparation of NUP or one or more of the active ingredients (compounds of formulas I and II) described herein with other chemical components such as physiologically suitable carriers and excipients. The purpose of a pharmaceutical composition is to facilitate administration of NUP or compounds of formulas I and II to a subject.

In one embodiment, "active ingredient" refers to NUP as NUP is accountable for the biological effect as described herein. In one embodiment, "active ingredient" includes the compounds of formulas I and II as described herein and at least one additional anti-cancer agent.

In one embodiment, the phrases "physiologically acceptable carrier" and "pharmaceutically acceptable carrier" which be interchangeably used refer to a carrier or a diluent that does not cause significant irritation to an organism and does not abrogate the biological activity and properties of the administered compound. An adjuvant is included under these phrases. In one embodiment, one of the ingredients included in the pharmaceutically acceptable carrier can be for example polyethylene glycol (PEG), a biocompatible polymer with a wide range of solubility in both organic and aqueous media (Mutter et al. (1979).

In one embodiment, "excipient" refers to an inert substance added to a pharmaceutical composition to further facilitate administration of an active ingredient. In one embodiment, excipients include calcium carbonate, calcium phosphate, various sugars and types of starch, cellulose derivatives, gelatin, vegetable oils and polyethylene glycols.

Techniques for formulation and administration of drugs are found in "Remington's Pharmaceutical Sciences," Mack Publishing Co., Easton, Pa., latest edition, which is incorporated herein by reference.

In one embodiment, suitable routes of administration, for example, include oral, rectal, transmucosal, transnasal, intestinal or parenteral delivery, including intramuscular, subcutaneous and intramedullary injections as well as intrathecal, direct intraventricular, intravenous, inrtaperitoneal, intranasal, or intraocular injections.

Oral administration, in one embodiment, comprises a unit dosage form comprising tablets, capsules, lozenges, chewable tablets, suspensions, emulsions and the like. Such unit dosage forms comprise a safe and effective amount of the desired compound, or compounds, each of which is in one embodiment, from about 0.7 or 3.5 mg to about 280 mg/70 kg, or in another embodiment, about 0.5 or 10 mg to about 210 mg/70 kg. The pharmaceutically-acceptable carriers suitable for the preparation of unit dosage forms for peroral administration are well-known in the art. In some embodiments, tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. In one embodiment, glidants such as silicon dioxide can be used to improve flow characteristics of the powder-mixture. In one embodiment, coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. In some embodiments, the selection of carrier components depends on secondary considerations like taste, cost, and shelf stability, which are not critical for the purposes of this invention, and can be readily made by a person skilled in the art.

In one embodiment, the oral dosage form comprises predefined release profile. In one embodiment, the oral dosage form of the invention comprises an extended release tablets, capsules, lozenges or chewable tablets. In one embodiment, the oral dosage form of the invention comprises a slow release tablets, capsules, lozenges or chewable tablets. In one embodiment, the oral dosage form of the invention comprises an immediate release tablets, capsules, lozenges or chewable tablets. In one embodiment, the oral dosage form is formulated according to the desired release profile of the pharmaceutical active ingredient as known to one skilled in the art.

In some embodiments, compositions for use in the methods of this invention comprise solutions or emulsions, which in some embodiments are aqueous solutions or emulsions comprising a safe and effective amount of the compounds of the invention and optionally, other compounds, intended for topical intranasal administration. In some embodiments, these compositions comprise from about 0.01% to about 10.0% w/v of the compounds of NUP or formulas I and II described herein, more preferably from about 0.1% to about 2.0.

Further, the pharmaceutical compositions may be administered topically to body surfaces, and are thus formulated in a form suitable for topical administration. Suitable topical formulations include gels, ointments, creams, lotions, drops and the like. For topical administration, the compounds of the invention are combined with an additional appropriate therapeutic agent or agents, prepared and applied as solutions, suspensions, or emulsions in a physiologically acceptable diluent with or without a pharmaceutical carrier.

In one embodiment, pharmaceutical compositions for use in accordance with the invention is formulated in conventional manner using one or more physiologically acceptable carriers comprising excipients and auxiliaries, which facilitate processing of the active ingredients into preparations which, can be used pharmaceutically. In one embodiment, formulation is dependent upon the route of administration chosen.

In one embodiment, injectables, of the invention are formulated in aqueous solutions. In one embodiment, injectables, of the invention are formulated in physiologically compatible buffers such as Hank's solution, Ringer's solution, or physiological salt buffer. In some embodiments, for transmucosal administration, penetrants appropriate to the barrier to be permeated are used in the formulation. Such penetrants are generally known in the art.

In one embodiment, the preparations described herein are formulated for parenteral administration, e.g., by bolus injection or continuous infusion. In some embodiments, formulations for injection are presented in unit dosage form, e.g., in ampoules or in multi-dose containers with optionally, an added preservative. In some embodiments, compositions are suspensions, solutions or emulsions in oily or aqueous vehicles, and contain formulatory agents such as suspending, stabilizing and/or dispersing agents.

The compositions also comprise, in some embodiments, preservatives, such as benzalkonium chloride and thimerosal and the like; chelating agents, such as edetate sodium and others; buffers such as phosphate, citrate and acetate; tonicity agents such as sodium chloride, potassium chloride, glycerin, mannitol and others; antioxidants such as ascorbic acid, acetylcystine, sodium metabisulfote and others; aromatic agents; viscosity adjustors, such as polymers, including cellulose and derivatives thereof; and polyvinyl alcohol and acid and bases to adjust the pH of these aqueous compositions as needed. The compositions also comprise, in some embodiments, local anesthetics or other actives. The compositions can be used as sprays, mists, drops, and the like.

In some embodiments, pharmaceutical compositions for parenteral administration include aqueous solutions of the active preparation in water-soluble form. Additionally, suspensions of the active ingredients, in some embodiments, are prepared as appropriate oily or water based injection suspensions. Suitable lipophilic solvents or vehicles include, in some embodiments, fatty oils such as sesame oil, or synthetic fatty acid esters such as ethyl oleate, triglycerides or liposomes. Aqueous injection suspensions contain, in some embodiments, substances, which increase the viscosity of the suspension, such as sodium carboxymethyl cellulose, sorbitol or dextran. In another embodiment, the suspension also contain suitable stabilizers or agents which increase the solubility of the active ingredients to allow for the preparation of highly concentrated solutions.

In another embodiment, the active compound can be delivered in a vesicle, in particular a liposome.

In some embodiments, pharmaceutical compositions suitable for use in context of the invention include compositions wherein NUP or compounds of formulas I and II as described herein are contained in an amount effective to achieve a measurable anti-cancer effect. In some embodiments, a therapeutically effective amount means an amount of NUP or of compounds of formulas I and II as described herein effective to prevent, alleviate or ameliorate symptoms of cancer. In one embodiment, determination of a therapeutically effective amount is well within the capability of those skilled in the art.

In some embodiments, preparation of effective amount or dose can be estimated initially from in vitro assays such as by measurement the inhibition of nuclear factor κb. In one embodiment, a dose can be formulated in animal models and such information can be used to more accurately determine useful doses in humans.

Additional objects, advantages, and novel features of the invention will become apparent to one ordinarily skilled in the art upon examination of the following examples, which are not intended to be limiting. Additionally, each of the various embodiments and aspects of the invention as delineated hereinabove and as claimed in the claims section below finds experimental support in the following examples.

EXAMPLES

Materials and Methods

Materials:

Antibodies against p65, Rel B, p50 and p52 were obtained from Santa Cruz Biotechnology, caspase 9 and PARP antibodies were purchased from Calbiochem and from Cell Signaling respectively. Anti-mouse and anti-rabbit IgG peroxidase was obtained from Jackson ImmunoResearch and the anti-β-actin monoclonal antibody was purchased from MP Biomedicals.

Collection of Plant Extracts:

Plants were collected in the botanical garden of Tel Aviv University and in a *Nuphar Lutea* L. pond constructed in the Negev desert at the Blaustein Institutes for Desert Research. Immediately after harvesting, the plant material was submerged in liquid nitrogen and brought to the laboratory for storage at −80° C. until extracted or oven dried as described above and the powder was used to extract the active fraction.

Preparation of Plant Extracts for Screening Assay:

Samples containing one g of frozen plant material were ground in a pre-chilled mortar containing liquid nitrogen. Two ml of 50% methanol/water (v/v) were added, and the slurry was mixed and kept on ice for 15 minutes. The mixture was then centrifuged at 11,000 rpm for five minutes at room temperature using a Hermle Z160M microfuge. The supernatant was stored at −80° C. for further analysis.

Partial Purification of the Active Fraction:

*Nuphar lutea* L. organs were oven-dried at 40-70° C., and ground in a mortar. 10 g of dry rhizome powder was extracted in 100 ml methanol. The mixed slurry was centrifuged (4,000 rpm, 4° C., 30 minutes). The supernatant was evaporated under reduced pressure. The residue was dissolved in 100 ml of a mixture of 1N HCl and chloroform (1:1, v/v). The mixture was separated on a separatory funnel. The aqueous phase was collected and adjusted to pH 9 by the addition of 25% NH$_4$OH. Precipitate was harvested by centrifugation and dissolved in acidic methanol. The solution was placed on a silica gel column that was developed with a mixture of chloroform/ethyl-acetate/diethylamine (20:1:1, v/v/v). Fractions were monitored using the NFκB luciferase reporter gene assay. They were then combined and evaporated to dryness under reduced pressure. The residue was dissolved in 50% methanol in water and used in the following experiments.

Figure 9:
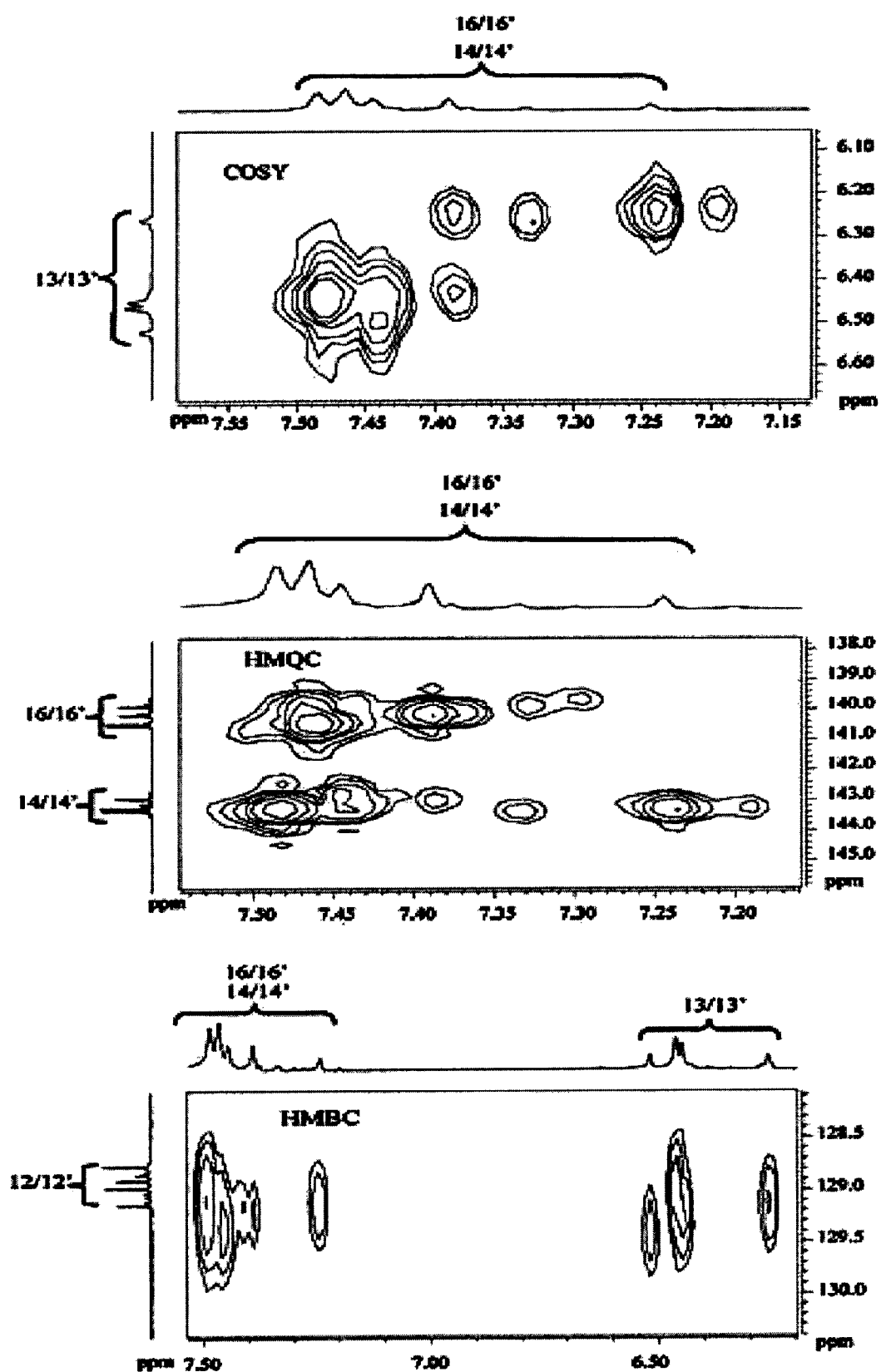
FIG. 9 depicts 1H-1H spin systems analyses comprising signals at 7.5-7.2 ppm and 6.6-6.2 ppm were identified by COSY experiments.

NMR spectra of the NUP mixture was recorded at 27° C. using a DRX 500 or Avance 500 spectrometer (Bruker Instruments, Karlsruhe, Germany). $^1$H and $^{13}$C NMR spectra were measured at 500 MHz and 125 MHz, respectively. The solvent was CD3OD. Two-dimensional COSY, HMQC and HMBC experiments were measured using standard Bruker software and parameter settings (Top Spin) (FIG. 9).

Preparation of the Active Fraction (NUP) of *Nuphar lutea* L.

Leaves (floating and submerged) of *Nuphar lutea* L. were oven-dried at 40-70° C., and ground in a mortar and pestle. Fifty gram of dry leaf powder was extracted in 400 ml methanol overnight by magnetic stirring of the mixture. The mixed slurry was centrifuged (10,000 rpm, 4° C., 30 min on a Sorvall centrifuged in a SS-34 rotor). The pellet was discarded and the filtered supernatant was evaporated under reduced pressure on a rotary-evaporator at 40° C. The residue was dissolved in 400 ml of a mixture of 1N HCl and chloroform (1:1, v/v), transferred to a separatory-funnel, mixed well and let stand for approx. 1 hour. The lower chloroform layer was separated and discarded and the upper aqueous layer was collected and adjusted to approx. pH 9 by the addition of 25% NH$_4$OH. The precipitate that was formed was harvested by centrifugation and dissolved in 50% water/methanol (or ethanol) mixture, and the pH adjusted to approx. 2 for better solubilization. The pH of the solution was adjusted again to approx. 9 by the addition of 25% NH$_4$OH. The precipitate that was formed was harvested by centrifugation and dissolved in 50% water/methanol (or ethanol) mixture and the pH was adjusted to approx. 4 by addition of 1N HCl. The solution was let stand at 4° C. for at least 1 hour, then centrifuged and the yellowish supernatant obtained contained 5 to 10 mg/ml dry matter. This was labeled NUP and used for the biological tests.

Cell Culture:

Hodgkin's lymphoma (HL)-derived L428 and breast carcinoma derived MCF7 cell lines were maintained in RPMI 1640 and DMEM medium, respectively. The medium was supplemented with 10% heat-inactivated fetal bovine serum, 1% L-glutamine, and 1% Pen-Strep (Beit-Haemek, Israel). MCF7 cells were passaged by trypsinization. The absence of IκB in L428 cells was confirmed by western blot (not shown).

Cell Viability:

Cell survival was measured by a tetrazolium-formazan XTT assay kit (Beit Haemek) in 96-well plates. 3×10$^4$ L428 cells/well in 100 μl medium were treated with different concentrations of NUP, cisplatin (Pharmachemie B.V., Holland) and etoposide (EBEWE Pharma, Austria) for 48 h at 37° C. XTT solution (25 μl) was added, and the plates were again incubated for 4 h at 37° C. Absorbance was read at 450 nm by an ELISA reader.

The cytotoxic effect of NUP in combination with other chemotherapeutic drugs was performed in pairs by simultaneous addition of low concentrations of each individual compound (5-20% cytotoxicity) and measured by XTT as described above.

Generation of Stable Luciferase-NFκB Reporter Gene Transfectants:

L428 cells stable transfectants were generated by electroporation of the luciferase, NFκB-Luc reporter gene contained the consensus sequence derived from the human IL-2 promoter. This reporter gene was provided by M. Aboud, Department of Microbiology and Immunology, Ben Gurion University of the Negev. Stable transfectants were selected by the addition of 1,000) μg/ml of G418 (Gibco) and maintained in 500 μg/ml of G418.

Luciferase-NFKB Reporter Gene Assay:

L428 cells (10$^6$ per well) expressing the luciferase-NFKB reporter gene were incubated in 1 ml of medium containing 10 μl of methanolic plant extracts with different concentrations of NUP for 2 h. A time dependent experiment was also performed by incubating cells with 6 μg/ml of NUP for up to 3 hrs. Cells were then harvested, lysed and monitored by a luciferase reporter assay kit (Promega) according to the manufacturer's instructions. Measurements were carried out using a luminometer at 300 nm. Data were normalized to the protein concentration in each lysate as measured by the Bradford method (BioRad).

Western Blot Analysis:

Nuclear and cytoplasmatic protein lysates ($6\times10^6$ cells per sample) were prepared using the NucBuster kit (Novagen). Protein concentrations were estimated using the Bradford method (BioRad). Protein extracts (30-100 µg) were separated in 10% SDS-polyacrylamide gel and were then blotted onto nitrocellulose membranes. The membranes were incubated with the primary antibodies and subsequently with peroxidase-linked anti-mouse or anti-rabbit IgG. Protein bands were detected by chemiluminescence with ECL (Amersham). Recombinant human TNFα from R&D systems was used to induce NFκB activation in MCF7 cells prior to lysis.

Electrophoretic Mobility Shift Assay (EMSA):

Assays were performed essentially as described by the Pierce, Lightshift Chemiluminescent EMSA kit protocol with Tris-borate as the buffering system. Both complementary oligonucleotides (NFκB 5-AGT TGA GGG GAC TTT CCC AGG C-3', 5-GCC TGG GAA AGT CCC CTC AAC T-3) were 3' end-labeled with biotin and annealed. Binding reactions, (20 µl final volume) contained 7 µg of nuclear extract. Unlabeled oligonucleotides were added at a 100-fold molar excess as negative control. The complexes formed were visualized by electrophoresis through nondenaturing polyacrylamide gels, transferred to positively charged nylon membranes and detected with a strep-avidin-peroxidase linked antibody and chemiluminescence.

Immunocytochemistry:

Cellular localization of NFκB sub-Cellular localization of NFκB subunits in treated L428 cells was done in experiments where the cells were incubated for 2 h at 37° C. with NUP. After incubation the cells were cytocentrifuged (Shandon Cytospin 4) at 900 rpm for 5 min and fixed in 10% formalin overnight. Samples of these cells were incubated separately with antibodies against p65, Rel B, p50 and p52, then with their respective anti-mouse or anti-rabbit IgG-peroxidase-linked secondary antibody, and detected by the ABC-Vectastin immunoperoxidase method (Vector laboratories) (brown). The nuclei were counterstained with Hematoxilin (blue).

Annexin V Assay:

An early indicator of apoptosis is the rapid translocation and accumulation of the membrane phospholipid phosphatidylserine from the cell's cytoplasmic interface to the extracellular surface. This loss of membrane asymmetry can be detected using the binding properties of Annexin V. Cells were pretreated with different concentrations of NUP for 2 hrs. An Annexin V/FITC Kit (Bender MedSystems) was used to detect early apoptosis according to the manufacturers protocol. Fluorescence analysis was determined with a flow cytometer (FACSCalibur).

Example 1

*Nuphar Lutea* Extracts Contain a Potent NFκB Inhibitor

Figure 2A:
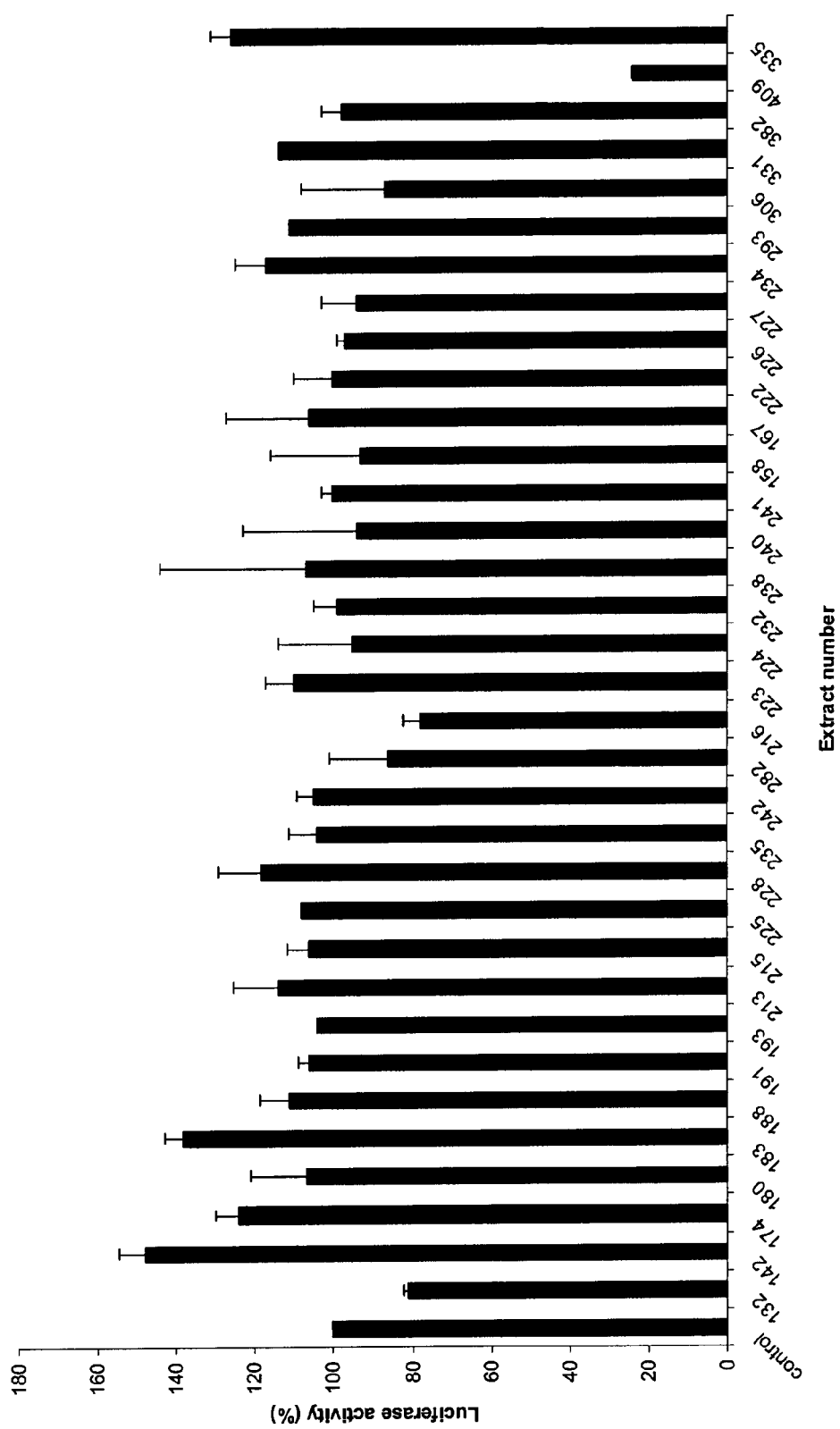
FIG. 2 demonstrates the NFκB inhibition by different methanolic plant extracts. (A) a bar graph showing the results of triplicate wells of L428 cells expressing the luciferase-NFκB reporter gene that were incubated with methanolic plant extracts (40 μg/ml) or with solvent only (control) for 2 h. The cells were then harvested and lysed; cell extracts were monitored by a luciferase reporter assay kit. NFκB-luciferase activity in control cells was taken as 100%. The average and standard deviation of three independent experiments is shown. (B) A bar graph showing the effect of methanolic extracts from various organs of extract 409 (*Nuphar lutea*) on NFκB. NFκB inhibition was determined by a NFκB luciferase reporter gene assay as described in (A). Flower, F; fruit, FR; flower petiole, FS; submerged leaf, LS; leaf petiole, LP; floating leaf, LF; fine root, RI; rhizome, RH; oven dried leaf, S. (C) Structures of major NUP components. (A) 6-hydroxythiobinupharidine. (B) 6-hydroxythionuphlutine B. (D) A bar graph showing the dose response inhibition of NFκB by NUP. Several concentrations of NUP were tested by the NFκB luciferase reporter gene as described in (a).
Figure 2B:
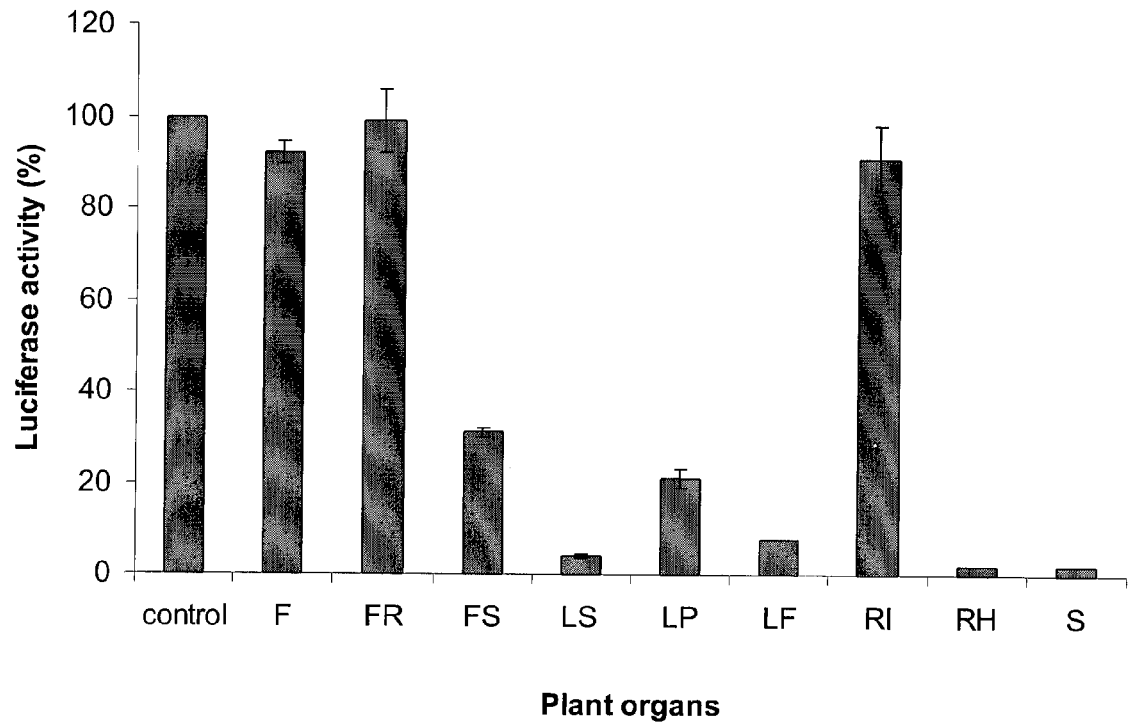

A collection of over 400 plant species mainly from arid lands, traditional Bedouin medicine and the Tel-Aviv Botanical Garden was obtained and solvent extracts of different plants and plant products were prepared. In order to detect potential anticancer and anti-viral and anti-inflammatory activity, 34 methanol extracts were screened from this collection (Table 1). Inhibition of NFκB constitutive activity was detected by a luciferase-NFκB reporter gene (FIG. 2A). The extract of the aquatic plant *Nuphar lutea* L. (extract 409) showed the most significant inhibition of NFκB. The activity concentrated mainly in leaves and rhizome of the plant (FIG. 2B). The partially purified methanolic extract of *Nuphar lutea*) L. (NUP) (see below), exhibited cytotoxicity against several human cell lines, after incubation for 24 h: L428 (LD50 0.25 µg/ml), KMH-2 (Hodgkin lymphoma, LD 50 0.25 µg/ml), U937 (monocytic, LD 50 0.01 µg/ml), Jurkat (T-cell, LD 50 0.01 µg/ml), BG, (melanoma LD 50 0.125 µg/ml). These results suggest that cells with constitutive NFκB activity are more resistant to NUP.

TABLE 1

| Ext. No. | Family | Plant name | Plant parts |
|---|---|---|---|
| 213 | Anacardiaceae | *Pistacia atlantica* Desf. | inforescence male |
| 226 | Caesalpiniaceae | *Ceratonia siliqua* L. | leaf |
| 225 | Cistaceae | *Fumana thymifolia* (L.) Webb | leaf & fruit |
| 382 | Compositae | *Eupatorium cannabinum* L. | leaf |
| 193 | Compositae | *Phagnalon rupestre* (L.) DC. | leaf & fruit |
| 191 | Compositae | *Urospermum picroides* (L.) F. W. Schmidt | leaf & fruit |
| 232 | Ericaceae | *Arbutus andrachne* L. | leaf & flower |
| 188 | Geraniaceae | *Erodium gruinum* (L.) L'Her. | leaf & fruit |
| 158 | Geraniaceae | *Erodium malacoides* (L.) L'Her. | leaf |
| 174 | Geraniaceae | *Geranium molle* L. | leaf, flower & fruit |
| 183 | Gramineae | *Hyparrhenia hirta* (L.) Stapf | leaf & flower |
| 215 | Labiatae | *Majorana syriaca* (L.) Rafin. | leaf |
| 216 | Labiatae | *Salvia fruticosa* Miller | leaf & flower |
| 224 | Labiatae | *Thymbra spicata* L. | leaf |
| 234 | Liliaceae | *Asphodelus ramosus* Miller | fruit |
| 235 | Liliaceae | *Asphodelus ramosus* Miller | leaf |
| 222 | Liliaceae | *Fritillaria persica* L. | leaf |
| 241 | Liliaceae | *Ornithogalum* spp. | leaf |
| 242 | Liliaceae | *Ornithogalum* spp. | flower |
| 306 | Loranthaceae | *Loranthus cruciatum* Boiss. | leaf |
| 331 | Malvaceae | *Alcea setosa* (Boiss.) Alef. | leaf & flower |
| 227 | Mimosaceae | *Acacia gerrardii* Bentham subsp. *negevensis* Zohary | leaf |
| 228 | Mimosaceae | *Acacia gerrardii* Bentham subsp. *negevensis* Zohary | Bark |
| 409 | Nymphaeaceae | *Nuphar lutea* (L.) Sm. | leaf & flower |
| 240 | Papilionaceae | *Trifolium clypeatum* L. | leaf & flower |
| 167 | Polygonaceae | *Polygonum equisetiforme* Sm. | leaf |

TABLE 1-continued

| Ext. No. | Family | Plant name | Plant parts |
|---|---|---|---|
| 132 | Pteridaceae | *Pteris vittata* L. | leaf |
| 335 | Ranunculaceae | *Ranunculus asiaticus* L. | leaf |
| 282 | Rhamnaceae | *Paliurus spina-christi* Miller | leaf |
| 142 | Rhamnaceae | *Ziziphus spina-christi* (L.) Desf. | leaf & flower |
| 238 | Rosaceae | *Crataegus aronia* (L.) DC. | leaf |
| 223 | Rosaceae | *Sarcopoterium spinosum* (L.) Spach | leaf & flower |
| 180 | Thymelaeaceae | *Thymelaea hirsuta* (L.) Endl. | leaf & flower |
| 293 | Umbellifrae | *Smyrnium olusatrum* L. | leaf |

Example 2

Partial Purification of the Active Principle and NMR Analysis

The extract of *N. lutea* was fractionated on silica gel as described under materials and methods. Fractions were monitored by the NFκB luciferase reporter gene assay. A fraction exhibiting strong cytotoxicity was analysed by one- and two-dimensional NMR spectroscopy. The $^1$H and $^{13}$C NMR spectra indicated the presence of several dimeric thioalkaloids. More specifically, typical 1H-1H spin systems comprising signals at 7.5-7.2 ppm and 6.6-6.2 ppm were identified by COSY experiments (FIG. 9).

Figure 2C:
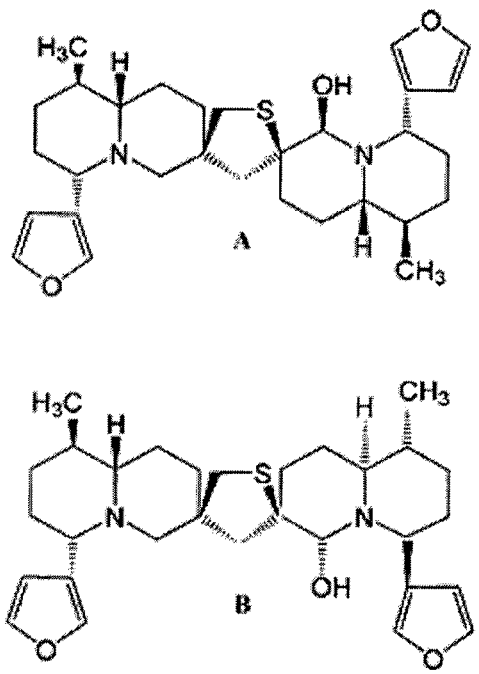

Earlier, H-14 and H-13 of the furan ring systems in thionupharidines and thionuphlutines have been shown to display this characteristic signal pattern. The tentative assignments were further confirmed by HMQC and HMBC experiments which displayed the expected patterns due to direct or long-range 1H-13C couplings, respectively (Table 2). From the number of signals detected at specific regions for given atoms of the compound family it can be concluded that the mixture contained at least four members of the thioalkaloid family, such as 6-hydroxythiobinupharidine and 6-hydroxythionuphlutine B (FIG. 2C).

TABLE 2

| Position | Chemical shift, ppm $^1$H | COSY | HMQC | HMBC |
|---|---|---|---|---|
| 1 | 1.18-1.27* | | | |
| 2α | 1.64-1.66* | | | |
| 2β | 1.09-1.11* | | | |
| 3-H$_2$ | 1.67-1.69* | 4 | | |
| 4 | 3.65-3.67* | 3 | 4 | |
| 6α | 3.79(s) | | 6α | 4, 7, 10 |
| 6β | | | 6β | |
| 8α | 1.30-1.31* | | | |
| 8β | 1.84-1.86* | | | |
| 9α | 1.19-1.28* | | | |
| 9β | 1.43-1.80* | | | |
| 10 | 2.30-2.32* | | | |
| 11-H$_3$ | 0.89-0.93* (d, J = 6.4 Hz) | | | 1, 2, 10 |
| 12 | — | | | 13, 14, 16 |
| 13 | 6.45-6.52* (d, J = 1.1 Hz) | 14, 16 | 13 | 12, 14, 16 |
| 14 | 7.43-7.45* (t, J = 1.5 Hz) | 13, 16 | 14 | 13, 16 |
| 16 | 7.39-7.47* (br s) | 13, 14 | 16 | 13, 14 |
| 17α | 1.67-1.87* (d, J = 14.8 Hz) | | 17 | 7, 8 |
| 17β | 2.09 (d, J = 13.8 Hz) | | | 7, 8 |
| 1' | 1.50 (d, J = 2.9 Hz) | | | |
| 2'α | 1.61-1.74* | | | |
| 2'β | 1.09-1.16* | | | |
| 3'-H$_2$ | 1.61-1.66* | 4' | | |
| 4' | 2.96, 3.65* (dd, J = 2.8, 11.5 Hz) | 3' | 4' | |
| 6'α | 2.93 (d, J = 12.3 Hz) | | 6'α | 4', 7', 10' |
| 6'β | 1.57 (d, J = 11.7 Hz) | | 6'β | |
| 8'α | 1.55* | | | |
| 8'β | 1.14* | | | |
| 9'α | 1.30* | | | |
| 9'β | 1.85-1.91* | | | |
| 10' | 1.55* | | | |
| 11'-H$_3$ | 0.96 (d, J = 6.4 Hz) | | | 1', 2', 10' |
| 12' | — | | | 13', 14', 16' |
| 13' | 6.26 (d, J = 1.1 Hz) | 14', 16' | 13' | 14', 16' |
| | 6.28 (d, J = 1.7 Hz) | | | |
| | 6.34 (d, J = 1.7 Hz) | | | |
| | 6.39 (d, J = 1.4 Hz) | | | |
| 14' | 7.39 (t, J = 1.2 Hz) | 13', 16' | 14' | 13', 16' |
| | 7.43 (t, J = 1.4 Hz) | | | |
| | 7.45 (t, J = 1.4 Hz) | | | |
| 16' | 7.39* (br s) | 14', 13' | 16' | 13', 14' |
| 17'α | 2.23 (d, J = 12.0 Hz) | | 17' | 7' |
| 17'β | 2.30 (d, J = 11.9 Hz) | | | 7' |

Example 3

Dose Dependent Inhibition of NFκB by NUP

Figure 2D:
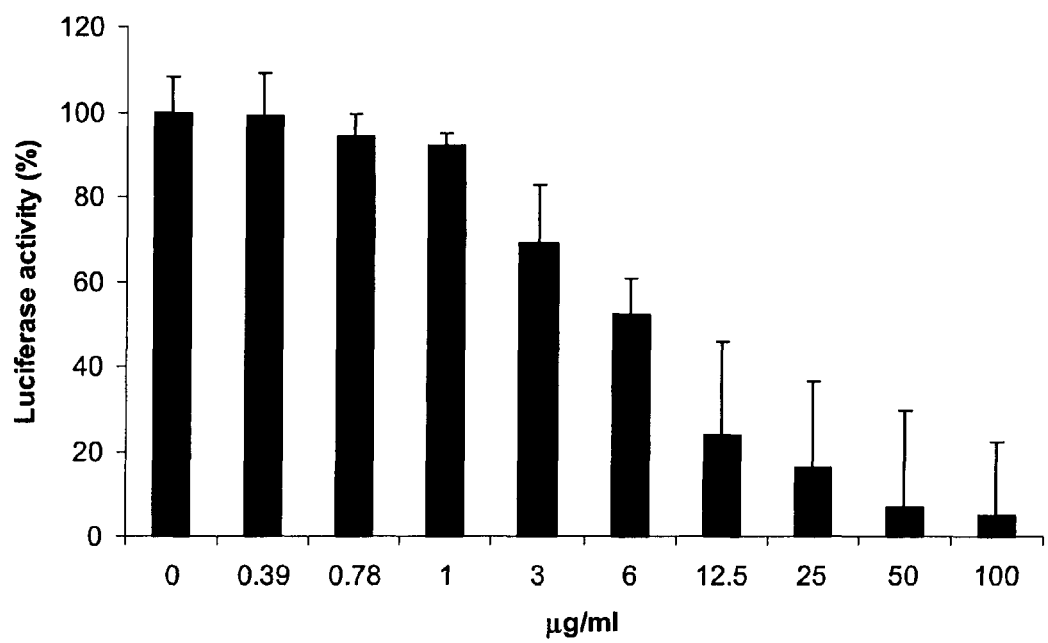
Figure 3A:
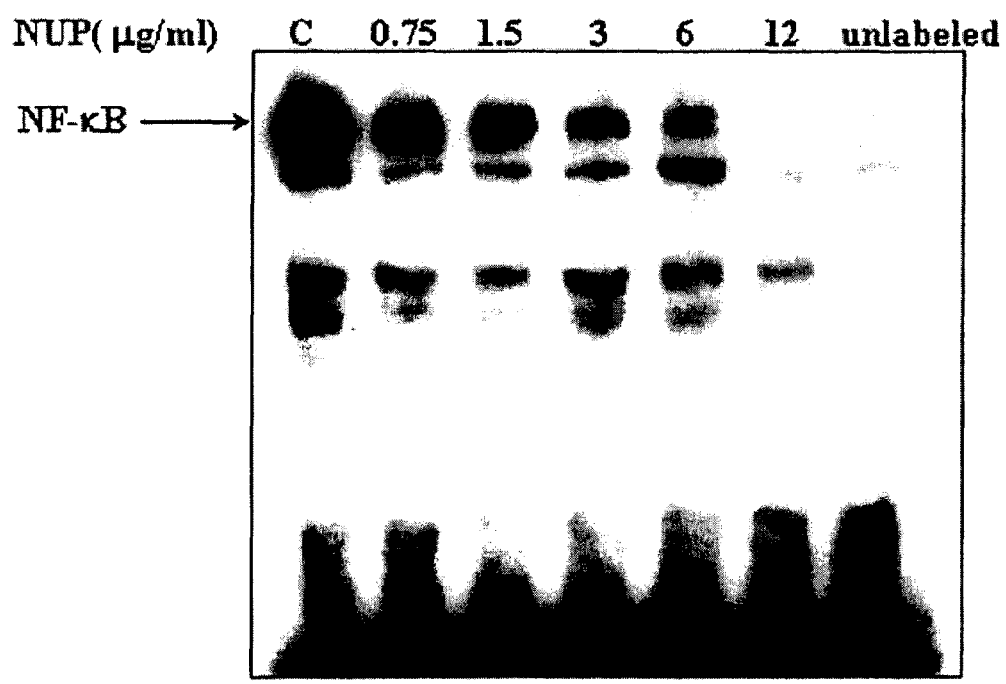
FIG. 3 demonstrates gel micrographs showing the inhibition of NFκB binding to DNA by NUP. (A) nuclear extracts from treated and control (50% methanol) L428 cells, were tested by electrophoretic mobility shift assay (EMSA) with a biotin labeled NFκB DNA probe as described in herein below. Unlabeled DNA was added in 100-fold molar excess as a specific competitor. (B) nuclear extracts of methanol or NUP (6 μg/ml for 2 hours) treated L428 cells were prepared. Supershift of NFκB p50 and p65 subunits was demonstrated by incubation of extracts from methanol treated cells with the corresponding antibodies prior to the addition of the labeled DNA (Representative of three independent experiments).

A dose dependent inhibition of NFκB luciferase reporter gene activity was obtained by incubation of L428 cells with NUP (FIG. 2D). This result was confirmed by EMSA and supershift experiments of nuclear lysates. Incubation of the cells with increased concentrations of NUP decreased the binding of p50 and p65 to DNA (FIGS. 3A and B).

Example 4

NUP Treatment Decreases the Amounts of Nuclear NFκB Subunits

Figure 4A:
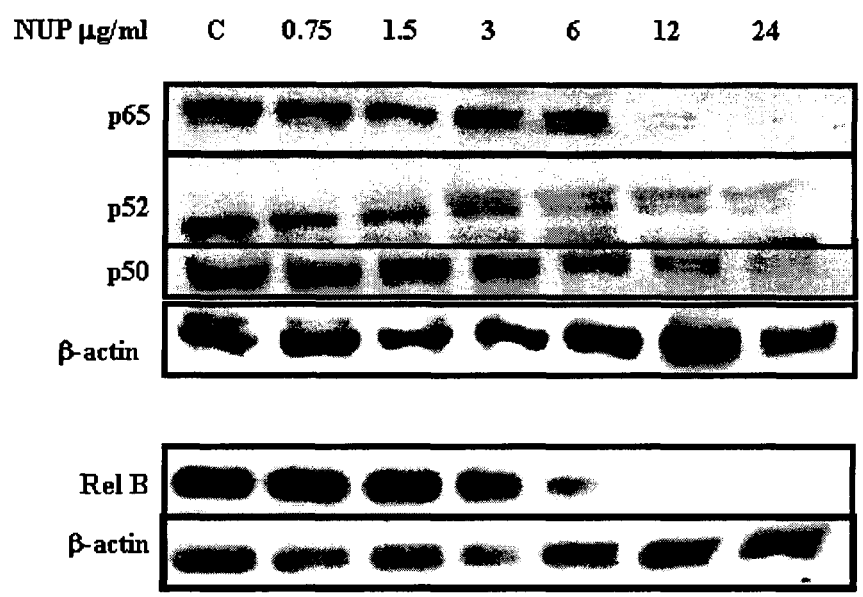
FIG. 4 shows NUP dose dependent downregulation of NFκB subunits in the nucleus. (A) Gel micrograph of the NFκB units in L428 cells that were incubated with NUP at different concentrations or with vehicle (methanol) (C) for 2 h. Nuclear extracts were prepared and western blots were run with antibodies against p50, p65, Rel B and p52. anti-β-actin was used as loading control. (B) Cytoimmunochemistry micrographs showing detection of NFκB subunits by immunohistochemistry. L428 cells were treated with vehicle (Control) or NUP. The cells were cytocentrifuged, fixed with formalin and immunostained with antibodies against p65, p50, p52 or Rel B followed by anti-mouse or anti-rabbit peroxidase-linked IgG and counterstained with hematoxilin. arrows point to stained (top) and unstained (bottom) nuclei.
Figure 4B:
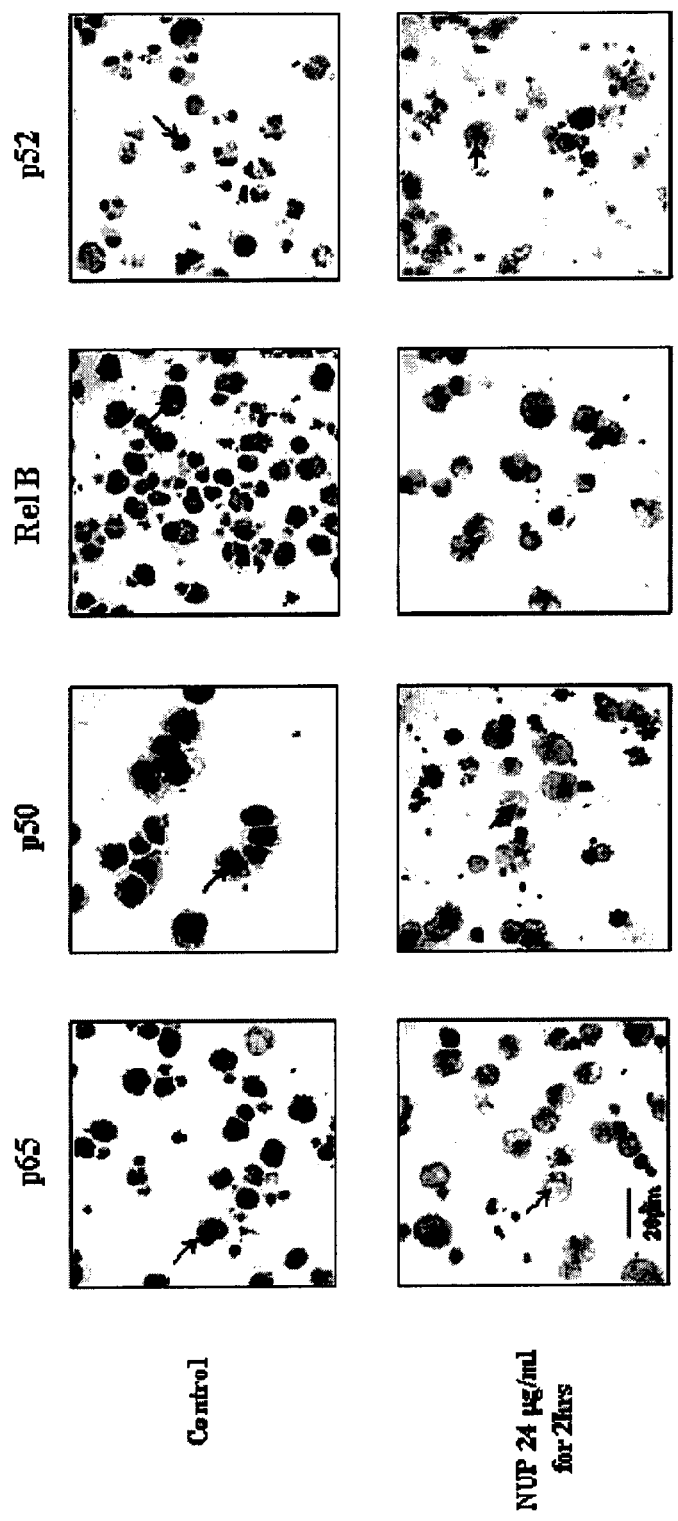

The amounts of p65, p50, Rel B and p52 in nuclear extracts of NUP-treated and untreated L428 cells were determined by western blot. The results in FIG. 4A show that all NFκB subunits tested were diminished upon treatment. Further support to the western blot results was obtained by immunohistochemical comparison of treated and untreated L428 cells (FIG. 4B), which showed the depletion of constitutive NFκB subunits from the nuclei in treated cells.

Example 5

NUP Inhibits Inducible NFκB Activation and Its Effect is Not Cell Type Specific

Figure 5:
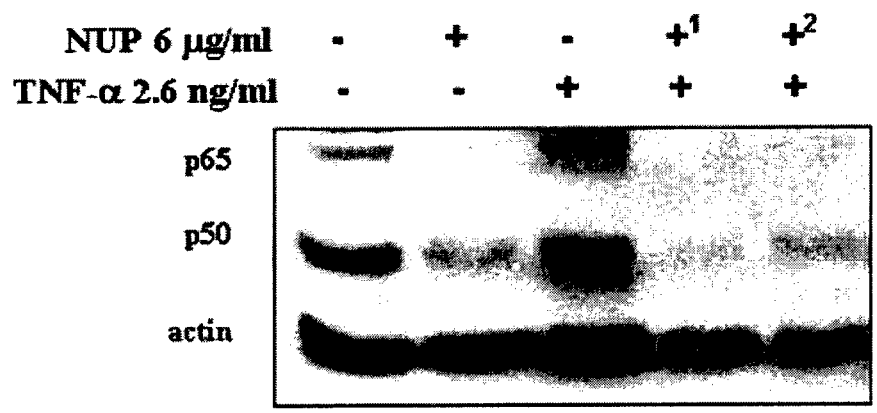
FIG. 5 is a gel micrograph showing the inhibition of inducible NFκB by NUP. MCF-7 cells were treated with vehicle (−) or NUP, 2 h before (+1) or after (+2) incubation with TNFα. Nuclear extracts were analyzed by western blot with antibodies against p65 and p50. anti-β-actin was used as loading control.

The signal transduction pathway mediated by NFκB is often distinctly different across different cell types. Here NUP ability to inhibit NFκB in MCF-7 cells where NFκB is inducible, was determined. The results in FIG. 5 show that NUP significantly inhibited NFκB activation when added both 2 h prior or 2 h following incubation with TNFα. Thus, NUP induced suppression of NFκB is not cell type specific, it prevents TNFα activation and inhibits NFκB following treatment with TNFα.

Example 6

NUP is Synergistic with Conventional Chemotherapy Drugs

Figure 6:
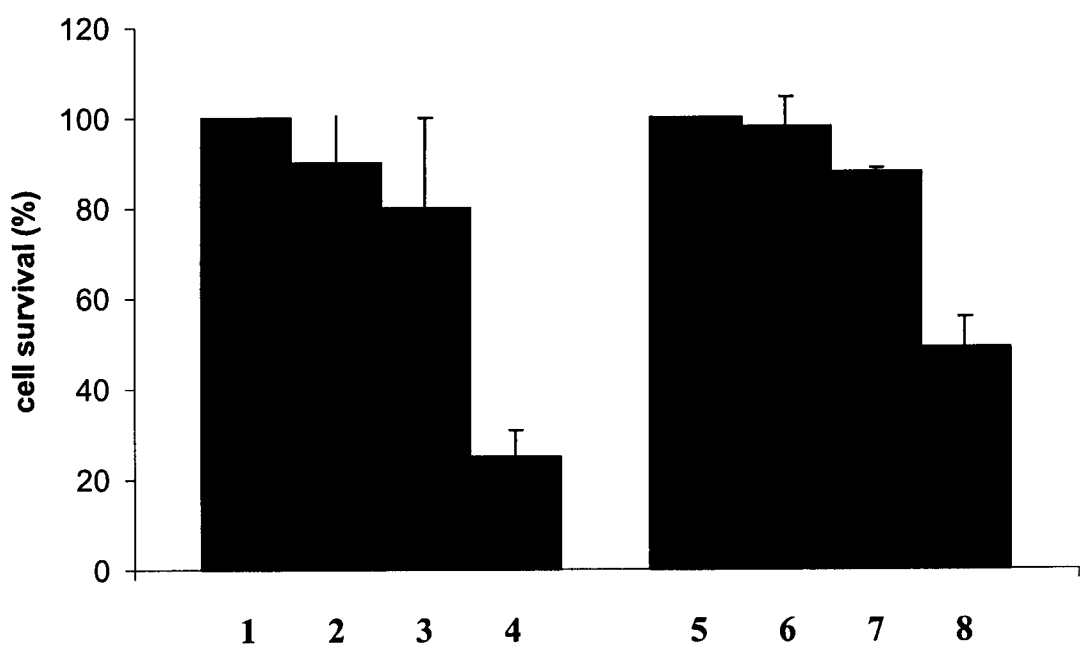
FIG. 6 is a bar graph showing the synergistic cytotoxic effect of NUP 0.1 µg/ml with cisplatin (bars 1-4) and etoposide (bars 5-8). L428 cells were incubated for 48 h in triplicate with 0.26 µM cisplatin (bars 3 and 4) or 0.5)µM etoposide (bars 7 and 8) in the presence (bars 2, 4, 6 and 8) or absence (bars 1, 3, 5 and 7) of NUP. Cell survival was measured by a tetrazolium-formazan XTT assay kit. Control cells treated with vehicle represent 100% survival. The average and standard deviation of three independent experiments is shown.
Figure 7A:
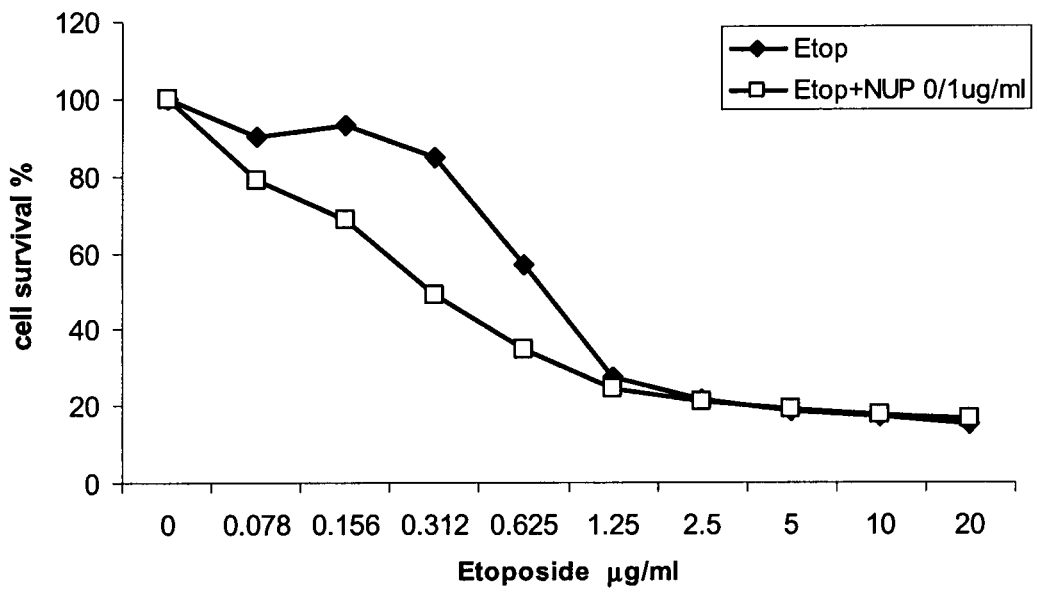
FIG. 7 depicts graphs showing the synergistic effect NUP has with the anti-cancer agents etoposide (a) and cisplatin (b).
Figure 7B:
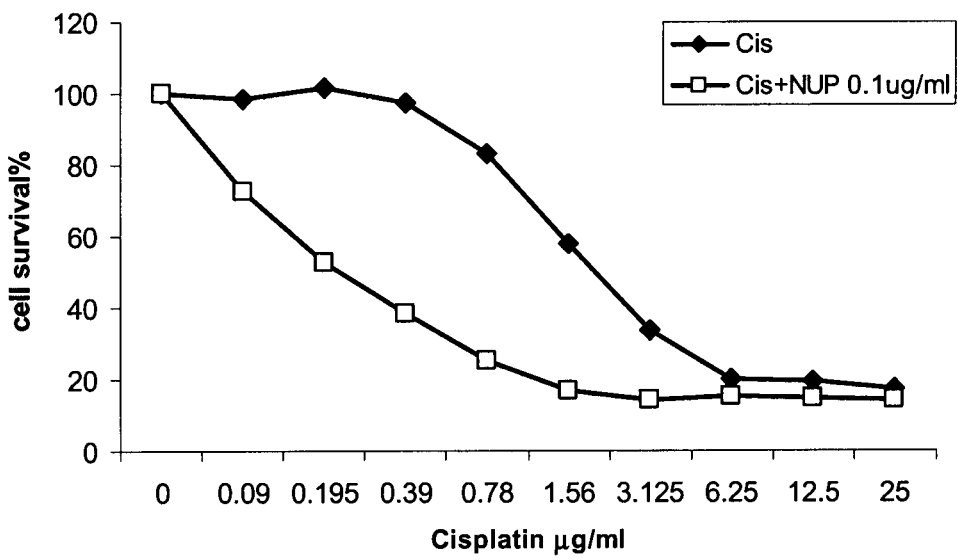

In this experiment the possibility that inactivation of NFκB may induce the sensitivity of cancerous cells to a chemotherapeutic agent was assessed. The cells were treated with suboptimal concentrations of cisplatin or etoposide in the absence or presence of NUP. Cell survival was determined after 48 h. As shown in FIGS. 6 and 7, NUP acted synergistically with both drugs and still lowered their cytotoxic effect at lower concentrations. Here it was unexpectedly demonstrated that treating L428 with a combination of a chemotherapeutical drug and NUP resulted in a synergistic effect. This combination is both synergistic and less toxic and therefore should be used in cancer treatment. Thus, this effect has a major impact in administering smaller quantities of harmful anticancer agents and thus reducing devastating, inherent, unwanted side effects. Bortezomib (0.9 ng/ml) was also tested under the same conditions. However, its effect on cell survival was additive to NUP and not synergistic. Data not shown.

Example 7

NUP Induces Apoptotic Cell Death

Figure 8A:
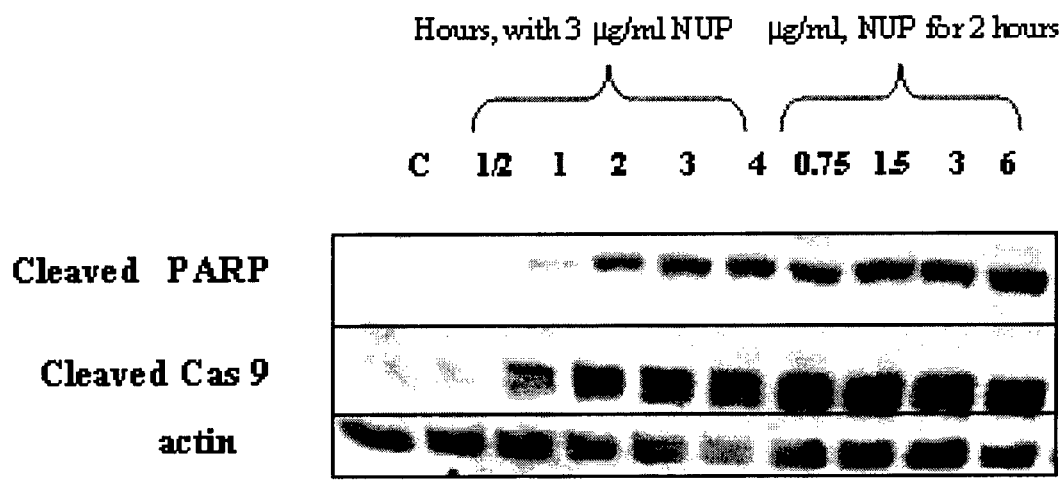
FIG. 8 shows induction of apoptosis by NUP. (A) A gel microgrqaph showing apoptosis markers in L428 cells that were incubated with solvent only (C) or NUP 3 µg/ml for several times and concentrations (for 2 h). Whole-cell lysates were prepared and western blots were performed to detect cleaved caspase 9 and cleaved PARP. (B) A bar graph showing time dependent inhibition of NFκB by NUP. L428 cells were incubated with 6 µg/ml NUP for different times. NFκB inhibition was determined by the NFκB luciferase reporter gene assay as described in FIG. 1a. The average and standard deviation of three independent experiments is shown. (C) A bar graph showing parallel determination of NFκB inhibition and annexin V/PI expression. L428 cells were pretreated with different concentrations of NUP for 2 h and tested for NFκB activity by the luciferase reporter gene assay (luciferase activity) as well as for early apoptosis (annexin V) and necrosis (PI) by an FITC-Annexin V/PI kit. Fluorescence analysis was determined with a flow cytometer (FaCsCalibur). annexin V and pI results were expressed as % of stained cells as compared to cells treated with 50% methanol.
Figure 8B:
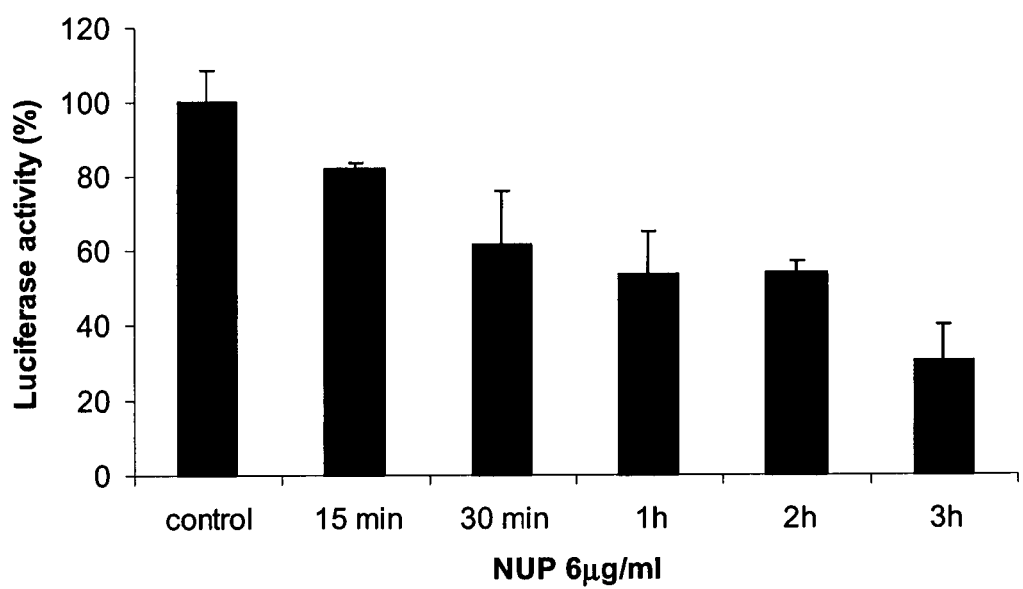
Figure 8C:
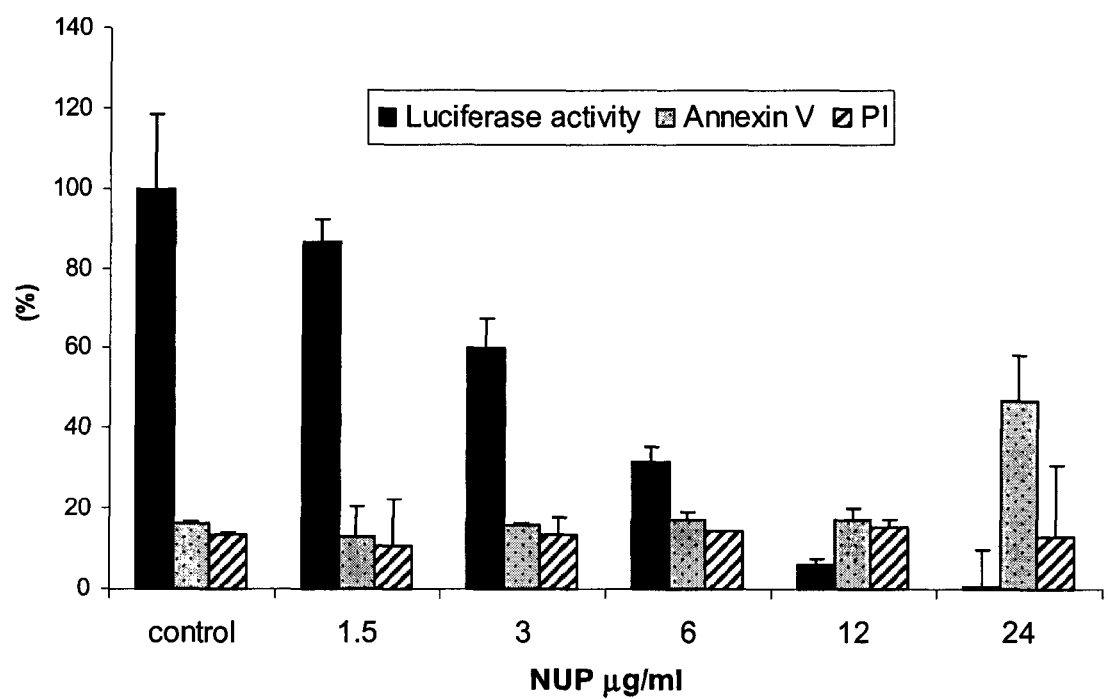

L428 cells were incubated for different time periods and concentrations of NUP. Cell lysates were prepared and activation of the apoptotic markers Caspase 9 and PARP were determined by western blot. Cleavage of both Caspase 9 and PARP was observed after one hour of incubation (FIG. 8A), indicating the ability of NUP to induce apoptosis. Inhibition of NFκB, as determined by the luciferase reporter gene assay, was detected before the detection of Annexin V, an early apoptosis marker (FIGS. 8B and C). These results, suggest that NFκB inhibition precedes apoptosis to some degree.

In these experiments the active principles detected in Nuphar lutea were partially purified by pH-dependent precipitation and silica gel chromatography. One- and two-dimensional NMR experiments identified thioalkaloids of the Nupharidine and/or nuphlutine family as major components in the inhibitory fraction (NUP).

NUP inhibited in a dose and time dependent fashion the constitutive activation of NFκB, it decreased the nuclear expression of p65, p50, p52 and Rel B, therefore affecting both the canonical and alternative pathways. In addition, a similar effect was observed following the activation of NFκB by TNFα in another cell line where the classical pathway is intact.

Figure 3B:
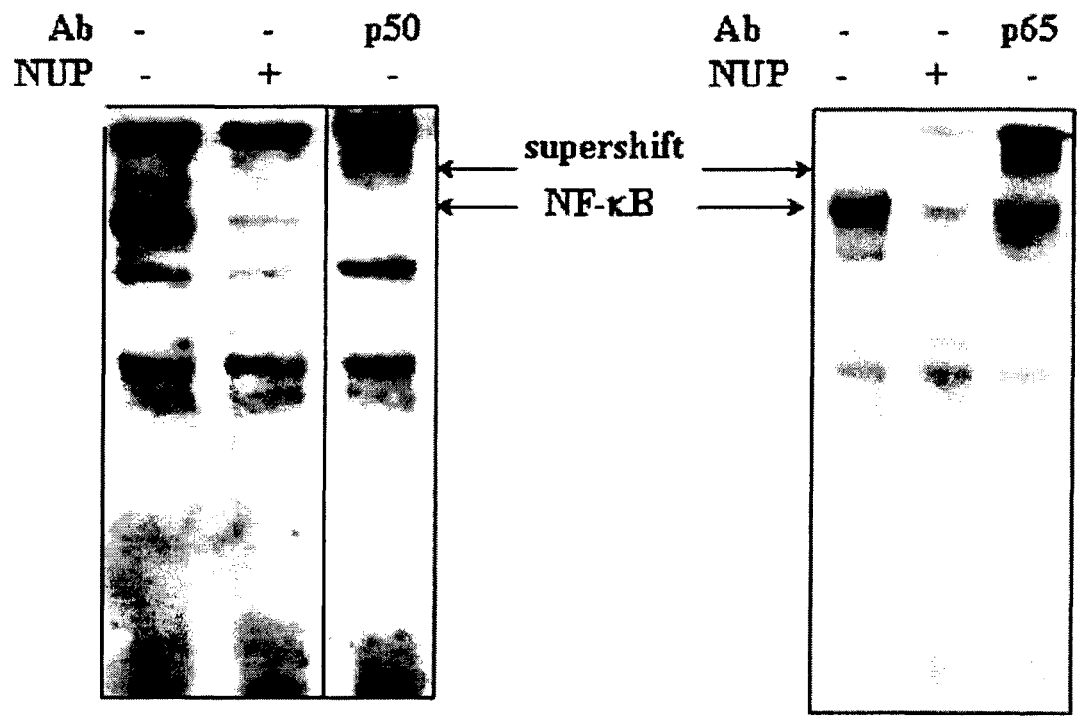

Here, it was discovered that NUP induced a marked reduction in nuclear NFκB without a significant increase in cytoplasmic NFκB (FIG. 3B). These results are corroborated by the western blot analysis results. The disappearance of NFκB from the nucleus without a concomitant increase in the cytoplasm is consistent with its degradation in the nucleus and not as a result of its export to the cytoplasm.

Post-induction repression of NFκB activity depends on NFκB regulated resynthesis of IκBα, which dissociates NFκB from DNA and exports it to the cytosol. Since IκBα is absent in L428 cells, export to the cytosol cannot occur by this mechanism. Degradation of promoter bound p65 is essential for the fast termination of the NFκB response. NUP seems to inhibit binding of NFκB to DNA and induce nuclear degradation of NFκB subunits. Nuclear proteosomal degradation of p65 does not merely regulate its stability and abundance, but also actively promotes transcriptional termination. The active NUP fraction downregulated NFκB subunits of both the canonical and the alternative pathways, and may directly inhibit the binding of NFκB to DNA. These results suggest a pleiotropic mode of action.

Cleavage of caspase 9 and PARP was detected within one-hour of incubation with 3 μg/ml NUP, confirming the ability of NUP to induce apoptosis. NFκB inhibition seems to precede apoptosis since reduction in luciferase activity was detected slightly before than caspase activation. Annexin V expression was observed only after incubation with high NUP concentrations. Compounds belonging to the nupharidine family have also been reported to show potent antitumor activity.

In these studies, NUP synergistically increased the cytotoxic effect of anti-cancer agents. Taken together the current results indicate that the thioalkaloids mixture obtained from N. lutea) (NUP) induced apoptosis and cytotoxic activity involving downregulation of the NFκB pathway.

Example 8

Pretreatment of Mice with NUP Protects from LPS-Induced Lethal Toxic Shock

Figure 10:
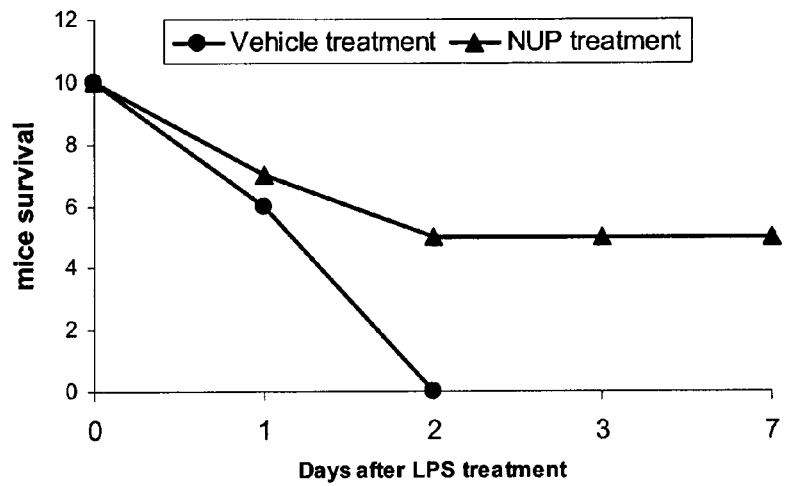
FIG. 10 is a graph showing the septic shock protective effect of a NUP composition. Ten Balb/C mice were i.p treated with 10 mg/kg of NUP or with vehicle for two days prior to the i.p. injection of LPS (50 mg/kg). Following LPS injection all untreated mice died after 48 hrs. 50% of NUP treated mice were unexpectedly protected and overcame LPS-induced septic shock.
Figure 11A:
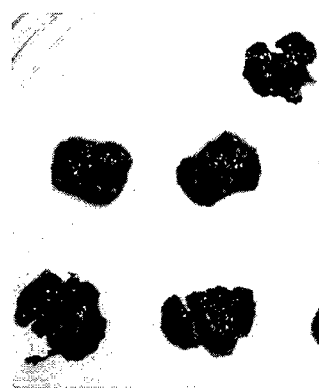
FIG. 11 is a photograph showing the anti-metastatic activity of NUP, cisplatin or both. C57BL/6 mice were given an intravenous injection of B16 melanoma cells (3*10$^5$ cells/200 µl PBS). NUP (20 mg/kg) (B), cisplatin (4 mg/kg) (C) or both (D) in PBS were given every other from day 0 to day 14. Control animals received only vehicle (A). Lungs were excised on day 18. Metastatic nodules are black.
Figure 11B:
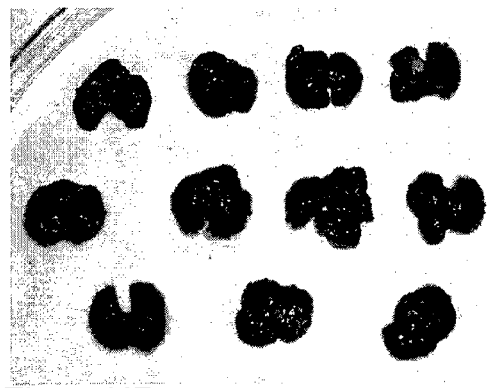
Figure 11C:
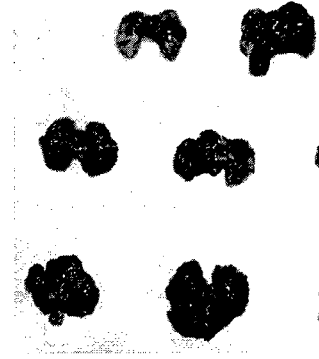
Figure 11D:
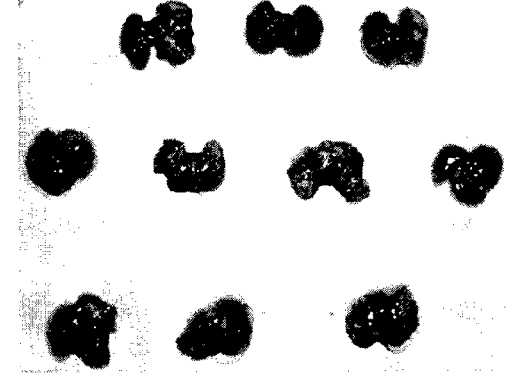

In this set of experiments, pretreatment of mice with NUP protects from LPS-induced lethal toxic shock. Ten Balb/C mice were treated i.p. with 10 mg/kg of NUP or with vehicle (methanol) for two days prior to the i.p. injection of LPS (50 mg/kg). Following LPS injection all untreated mice died after 48 hrs. 50% of NUP treated mice overcame LPS-induced septic shock. (FIG. 10).

Determination of cytokines from sera of treated mice. In order to determine if NUP affects the balance of cytokine expression in mice, Balb/c mice were treated with NUP or vehicle before treatment with LPS as described above. Four or six hours after LPS treatment the mice were sacrificed and blood was collected. The presence of cytokines in sera as determined by ELISA or by Quansis. The results are summarized in table 3. The following pro-inflammatory cytokines were significantly reduced: interferon-γ (IFNγ), interleukin-1β (IL-1β), tumor necrosis factor-α (TNF-α) and interleukin-6 (IL-6). The anti-inflammatory cytokine IL-10 was significantly elevated. Thus unexpectedly NUP activity encompasses both the induction of anti-inflammatory cytokine and the inhibition or reduction of pro-inflammatory cytokines.

Determination of Cytokines in Supernatants of Treated Macrophages

Since macrophages are major producers of cytokines during inflammation the effect of NUP treatment was tested, directly on thioglycolate-induced peritoneal macrophages from Balb/c mice. Macrophages were obtained and treated in vitro with different combinations of LPS and/or NUP: LPS only (for 2, 4, and 6 hrs.) or pretreatment with 0.75 μg/ml of NUP for 24 h before LPS treatment. Supernatants were collected and cytokines were measured (table 3). The following cytokines tested were reduced following NUP treatment: TNF-α, IL-1β, IL-6, and IL-12. IL-10 was reduced upon treatment.

TABLE 3

Determination of cytokines from sera of treated mice or supernatants of treated macrophages.

| Serum | Macrophage supernatant | Serum | Macrophage supernatant | Serum | Macrophage supernatant |
|---|---|---|---|---|---|
| IL-10 | | IL-6 | | TNF-□ | |
| 165 (4 h) | 291 (6 h) | 87 (4 h) | 56 (6 h) | 80 (4 h) | 56 (6 h) |
| 101 (4 h) | 164 (6 h) | | 63 (6 h) | 78 (4 h) | 65 (6 h) |
| 103 (4 h) | | | | | |
| 301 (6 h) | | | | | |
| 147 (6 h) | | | | | |
| IL-1β | | IL-1α | | IL-12 | |
| 95 (4 h) | NT | NT | 19 (6 h) | NT | 15 (6 h) |
| 62 (6 h) | | | 36 (6 h) | | 41 (6 h) |
| 29 (6 h) | | | | | |

The results of table 3 are expressed as % from control (100%)-(mice or macrophages treated with vehicle only). Each cell represents an independent experiment. Supernatants were done in triplicates and the in vivo results are an average value of sera from 8-10 mice. Standard deviation is indicated in the original experiment. Sera or supernatants were collected 4 or 6 hours after LPS treatment as indicated in parenthesis. Single experiments were not included such as Interferon-γ in sera-32 (6 h). NT—not tested These results indicate that preconditioning mice and macrophages with NUP reduces an anti-inflammatory response in two mechanisms: reduction/inhibition of pro-inflammatory agents and induction of ant-inflammatory agents.

Example 9

Dextran Sulphate (DSS) Induced Colitis

To further test the anti-inflammatory properties of NUP, a model of dextran sulphate (DSS) induced colitis (inflammatory bowel disease) was established. Six-week-old female C57-B1 mice were used for this study. Five mice per experimental group. A 3% DSS solution (molecular weight of 5000) in tap water was prepared. Mice were allowed free access to the DSS solution in drinking water for 7 days. NUP dissolved in water (20 mg/kg, 300 µl final volume) was administered on day 0 and day 3 of DSS exposure. A) intraperitoneal (IP) treatment or B) by oral administration (PO).

Each animal was weighed and blood in feces was determined daily with a commercial kit. Feces consistency was also determined. The disease activity index (DAI) score was determined according to Murthy et al 1993:

TABLE 4

Disease activity index score

| Score | Weight loss (%) | Stool consistency | Occult/gross bleeding |
|---|---|---|---|
| 0 | (—) | Normal | Normal |
| 1 | 1-5 | | |
| 2 | 6-10 | Loose | Guiac (+) |
| 3 | 11-15 | | |
| 4 | >15 | Diarrhea | Gross bleeding |

The disease activity index = combined score of weight loss, stool consistency and bleeding.
Normal stools = well formed pellets;
Loose = pasty stool which do not stick to the anus;
Diarrhea = liquid stools that sticks to the anus.

The results show that IP treatment with NUP was effective. Oral treatment (FIG. 24B) showed some effect (not significant) using the same IP concentration of NUP.

Figure 24A:
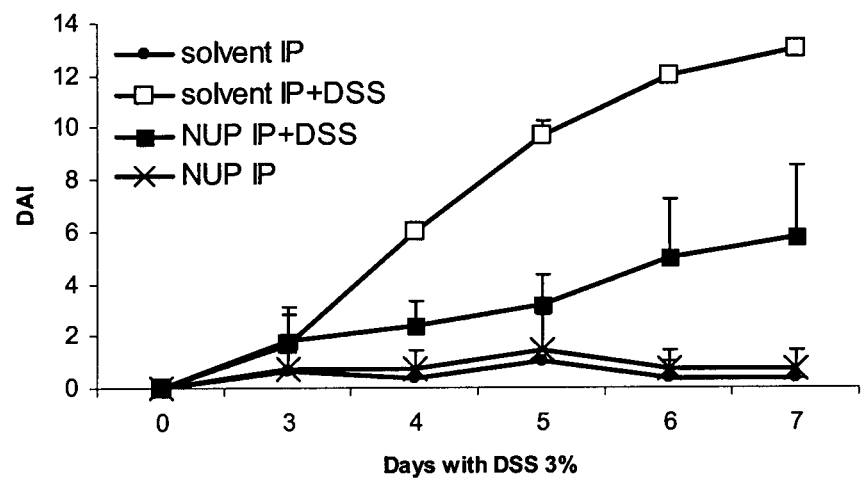
FIG. 24 shows the effect of NUP (A) intraperitoneal (IP) and (B) by oral administration (PO) on diminishing the Disease Activity Index (DAI) in DSS induced experimental colitis.
Figure 24B:
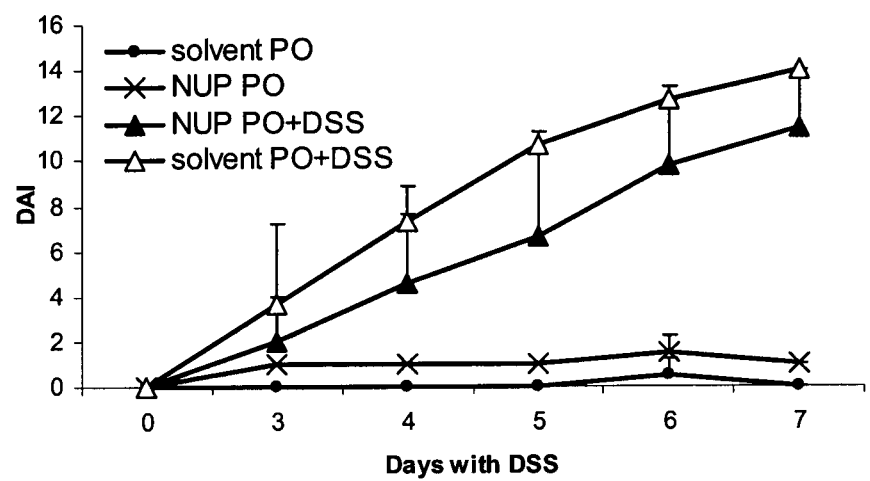

FIG. 24 shows the effect of NUP on diminishing the Disease Activity Index (DAI) in DSS induced experimental colitis. As can be seen from FIG. 24A, the DAI of IP treated mice was significantly lower than that of mice treated with vehicle and showed almost normal length.

Figure 25A:
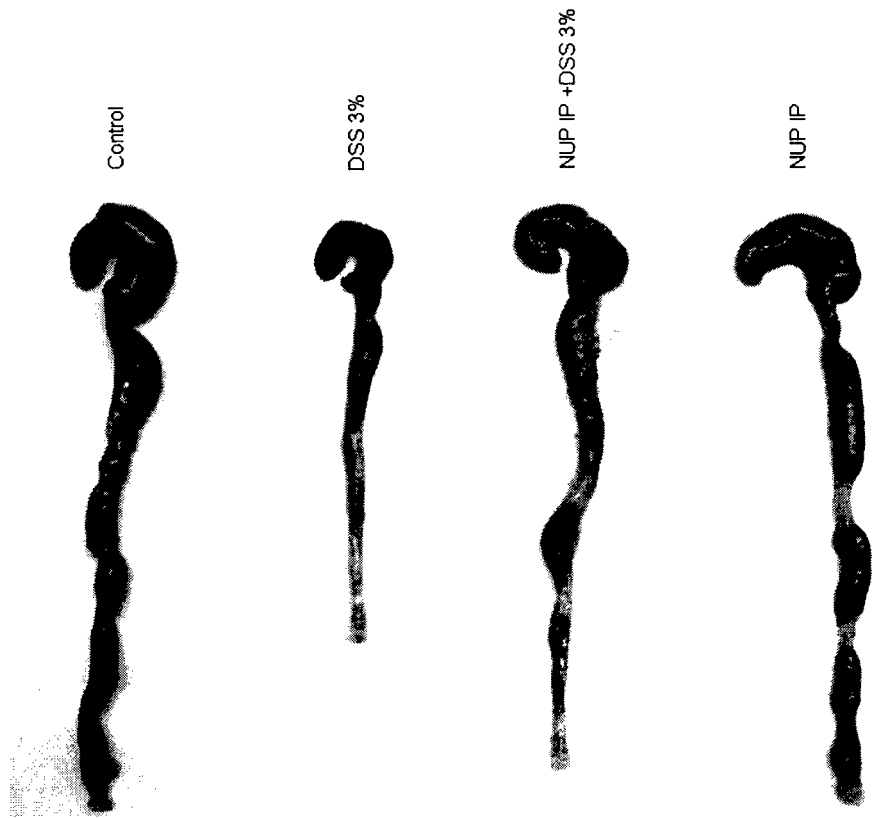
FIG. 25 shows comparison of colon length in DSS induced colitis in NUP treated or untreated mice. All mice in the experiment were sacrificed at day 7 and the large intestine was immediately removed for measurement: (A) a photograph of the intestine length and (B) a graph showing intestine length in cm. Shortening of the intestine was significantly prevented by IP treatment with NUP.
Figure 25B:
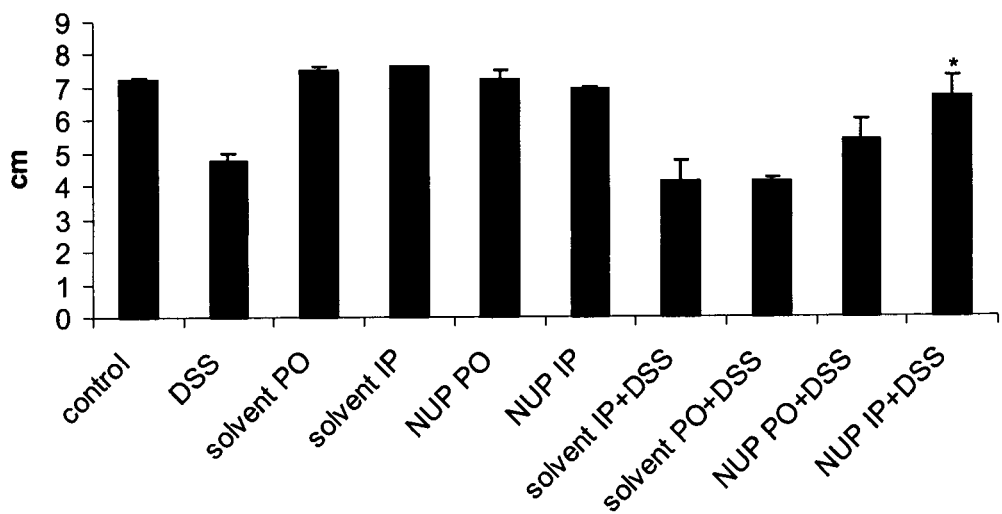

FIGS. 25A and B provides a comparison of colon length in DSS induced colitis in NUP treated or untreated mice.

All mice in the experiment were sacrificed at day 7 and the large intestine was immediately removed for measurement A) Picture of intestine length and B) intestine length. Shortening of the intestine was significantly prevented by IP treatment with NUP.

Figure 26:
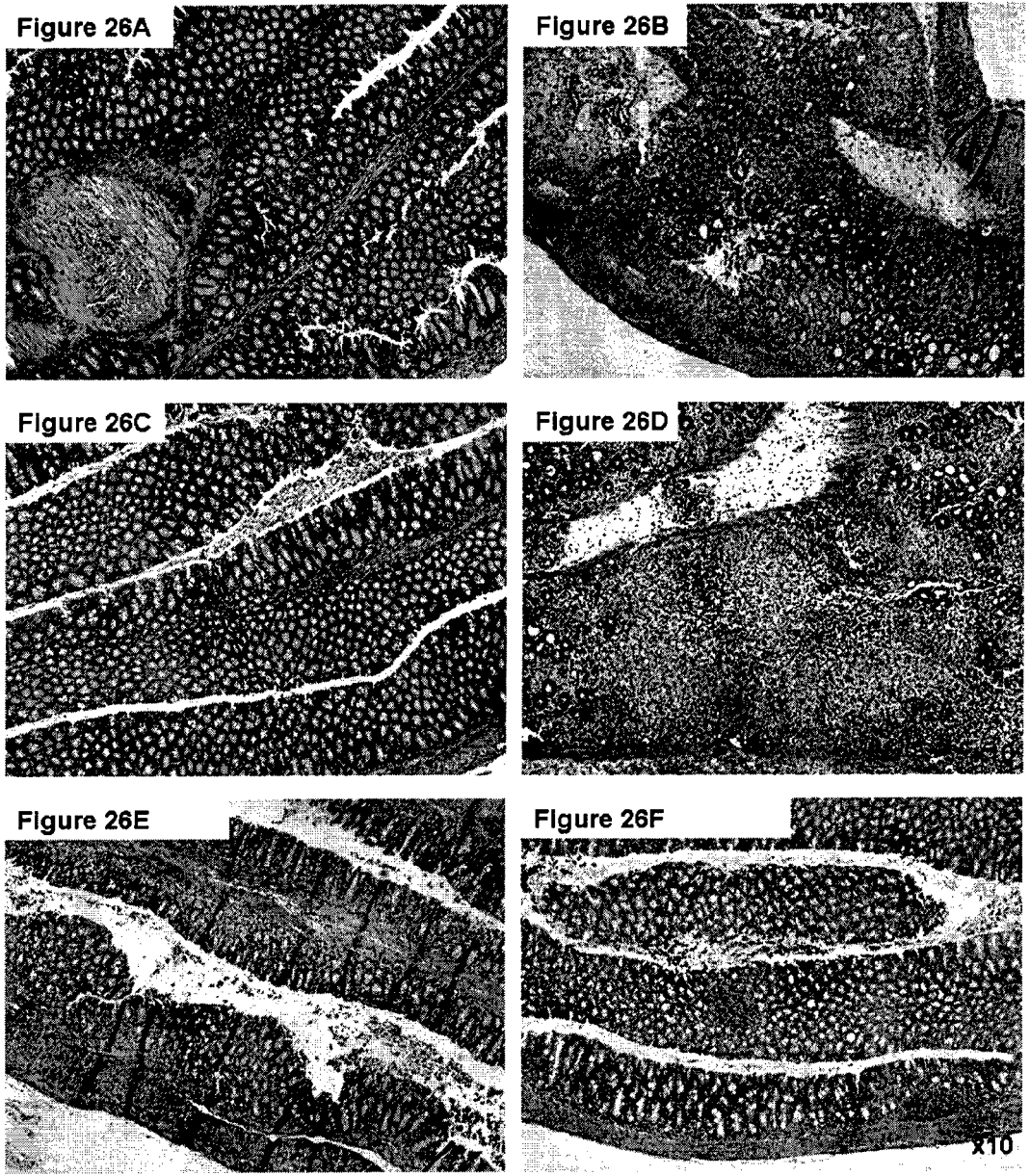
FIG. 26 shows histological finding of distal colon in mouse in DSS induced experimental colitis (A) control; (B) DSS 3%; (C) and (E) IP NUP in DSS injected mice; and (D) and (F) PO NUP in DSS 3% injected mice.

FIG. 26 shows the histological findings of distal colon in mouse. Intestines of representative mice were fixed in 4% formalin, paraffin blocks were prepared and cut by standard methods and stained with hematoxilin Eosine (H&E). Compared to the normal group (control-FIG. 26A), the DSS 3% group (FIG. 26B) exhibited marked erosion of the lamina propria mucosa, disappearance of glandular epithelium, inflammatory cell infiltration, and other related findings. In the NUP IP+DSS 3%-treated group (FIG. 26C and FIG. 26E) the findings of evaluation of inflammation did not differ markedly from the control group. In the NUP PO+DSS 3%-treated group (FIG. 26D and FIG. 26F) erosion, disappearance of glandular epithelium, inflammatory cell infiltration, and other abnormalities tended to be less severe than those in the DSS 3% group, but not normal.

Example 10

Induction of Colitis with DNBS

Colitis was induced with 1 mg DNBS per mouse (20 g). Mice were anesthetized by ketalar/xylazine. DNBS (1 mg in 100 µl of 50% ethanol) was injected into the rectum through a catheter inserted 3.5 cm proximally to the anus. Carrier alone (100 µl of 50% ethanol) was administered in control experiments. Thereafter, the animals were kept for 2 minutes vertically to avoid reflux. Mice were kept fasting (able to drink ad libidum) 14 hours prior to induction of colitis. After colitis and sham-colitis induction, the animals were observed for 7 days.

Experimental Design

Animals were randomly divided into groups: 1) Control n=3; 2) Sham n=4; 3) 2,4-dinitrobenzene sulfonic acid (DNBS) n=5; 4) Drug vehicle PO+Sham n=2; 5) Drug vehicle IP+Sham n=2; 6) NUP PO 60 mg/kg+Sham n=2; 7) NUP IP 20 mg/kg+Sham n=2; 8) Drug vehicle PO+DNBS n=3; 9) Drug vehicle IP+DNBS n=3; 10) NUP PO 60 mg/kg+DNBS n=5; 11) NUP IP 20 mg/kg+DNBS n=5; 12) azathioprine (AZA) PO 2.5 mg/kg+DNBS n=5; 13) 6-tioguanine (6-TG) PO 2 mg/kg+DNBS n=5.

NUP and drug vehicle were administrated on Day 0 and Day 3, AZA and 6-TG were administered daily starting at 4 h after the DNBS challenge.

Analysis of DAI (Disease Activity Index) score of colitis, evaluation of intestinal shortening, and histological evaluation.

On each day of the experiment, each animal will be weighed to check for weight loss. Appearance of feces and severity of bloody stool will be also checked, followed by calculation of the disease activity index (DAI) score according to the method reported by Murthy et al 1993 (Table 4). Each mouse will be then sacrificed at day 7 by $CO_2$ suffocation and the large intestine will be immediately removed for measurement of intestinal length and evaluation of intestinal shortening. Furthermore, the histological score of HE-stained specimens of the distal segment of the colon will be determined in accordance with the method for scoring reported by Coopers et al 1993 (Table 5).

TABLE 2

Histological disease score

| Grade 0 | Normal colonic mucosa |
| --- | --- |
| Grade 1 | Loss of one-third of the crypts |
| Grade 2 | Loss of two-third of the crypts |
| Grade 3 | The lamina propria is covered with a single layer of epithelium and mild inflammatory cell infiltration is present |
| Grade 4 | Erosions and marked inflammatory cell infiltration are present |

Example 11

Treatment with NUP, Cisplatin or Both Treats Melanoma and Reduces Lung Metastasis In this experiment it was shown that NUP significantly and unexpectedly reduces experimental lung metastasis of murine B16 melanoma cells. C57BL/6 mice were treated with an intravenous injection of B16 melanoma cells ($3*10^5$ cells/200 ml PBS). NUP (20 mg/kg) and cisplatin (4 mg/kg) in PBS were given every other from day 0 to day 14. Control animals received only vehicle. Lungs were excised on day 18. Metastatic nodules are black (FIG. 11). NUP or cisplatin treatments reduced the number of lung metastatic nodules. Treatment with both agents reduced metastasis better than NUP or cisplatin alone.

Figures 12A, 12B:
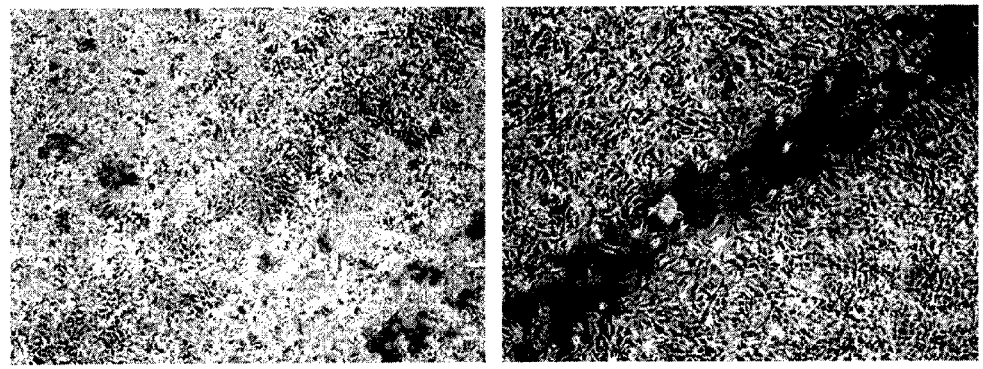
FIG. 12 is a micrograph of Wound-Scratch assay. B16 melanoma cell monolayers were "scratched" and were grown in the absence (A) (vehicle) or presence (B) of NUP (1.6 µg/ml) for 36 hrs. NUP prevented the cells from closing the wound.

The ability of NUP to inhibit metastasis was demonstrated by a cell migration assay. In this experiment it was shown that NUP inhibits cell migration. NUP inhibitory effect on cell migration was measured by the "wound-scratch assay". B16 melanoma cell monolayers were "scratched" with a plastic tip and were grown in the absence (vehicle) or presence of NUP (1.6 mg/ml) for 36 hrs. As shown in FIG. 12, NUP prevented the cells from closing the wound-inhibited migration-metastasis of these violent cancer cells.

Example 12

NUP Inhibits B16 Melanoma Cells Adhesion in Vitro

This experiment shows that NUP inhibits B16 melanoma cell adhesion in vitro, which consistent with its ant-metastatic properties in vivo.

Figure 27:
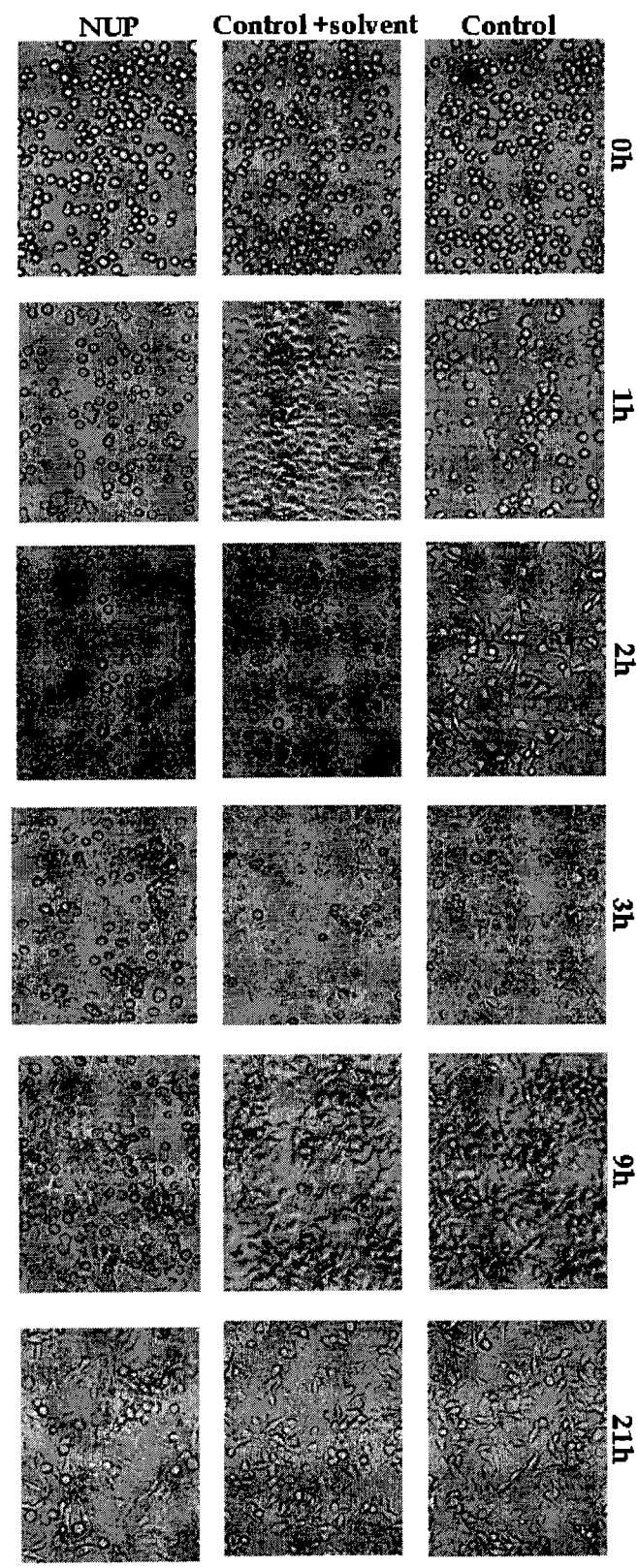
FIG. 27 shows that NUP inhibits B16 melanoma cells adhesion in vitro. B16 cells (5×10$^5$) were seeded on 6 well plates with or without NUP treatment (3.2 µg/ml). The adhesion to the wells was monitoring at indicated times. Round cells are non-adherent, flat cells are adherent. NUP inhibits cell adhesion.

B16 cells ($5\times10^5$) were seeded on six well plates (not coated) with or without NUP (3.2 µg/ml). The adhesion to the wells was monitoring at indicated times (0, 1 h, 2 h, 3 h, 9 h and 21 h. Round cells indicate non-adherent cells, flat cells indicate adherent cells. As can be seen from FIG. 27, NUP inhibited cell adhesion (top row-control, middle row-control with solvent (1:1 methanol:water) bottom row-NUP).

Measles Virus

Materials and Methods
Antibodies

Monoclonal: Anti-P-protein MV and Anti-N-protein MV were obtained from Argene, Verniolle, France. Anti-V protein was obtained from Dr. Kaoru Takeuchi, Department of Infection Biology, Graduate School of Comprehensive Human Sciences and Institute of Basic Medical Sciences, University of Tsukuba Japan. Anti-A20 MV was obtained from Santa Cruz, Santa Cruz, Calif. Anti-actin was obtained from MP Biomedical, Aurora, Ohio. Polyclonal: Anti-phospho-STAT-2 was obtained from Upstate, Peroxidase linked Donkey anti rabbit IgG was obtained from Jackson ImmunoResearch, West Grove, Pa. Peroxidase linked rabbit anti mouse IgG was obtained from Jackson ImmunoResearch, West Grove, Pa.

Growth Medium

The growth medium utilized are RPMI 1640 and DMEM-Beit Haemek, Israel. 10% fetal bovine serum (FCS)—Beit Haemek, Israel, 1% L-glutamine-Beit Haemek, Israel, 1% pen-strep-Beit Haemek, Israel, Trypsin EDTA-Beit Haemek, Israel, Cell Lines and Viruses L428 cells: Parental L428 cells were derived from Hodgkin's lymphoma patient (Purchased from the DSMZ-German Collection of Microorganisms and Cell Cultures, Braunschweig, Germany). The cells were maintained in RPMI 1640 medium, FCS 10%, 1% L-glutamine and 1% pen-strep.

MV Persistently infected L428 cells: A. L428 cells persistently infected with the MV Edmonston strain (L428+MV). These cells were obtained from Dr. Jindrich Cinatl, Institute of Medical and Experimental Virology Germany.

Figure 13:
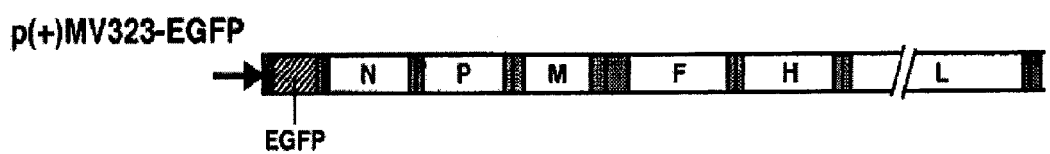
FIG. 13 is an illustration showing the six MV genes (N, P, M, F, H, and L) and the GFP gene are indicated. The shaded areas indicate untranslated regions, and the vertical lines within untranslated regions indicate the positions of intergenic trinucleotides.

L428 cells were also persistently infected with wild type MV strain containing the GFP gene (IC323-GFP). The virus was obtained from Dr. Yusuke Yanagi, Department of Virology, Faculty of Medicine, Kyushu University Japan (FIG. 13). IC323-GFP is recognized by the MV receptor CD150 but not by CD46.

UKF-NB cell line was derived from a human neuroblastoma. Both the parental and the UKF-NB Edmonston-MV persistently infected cells were obtained from Dr. Jindrich Cinatl, Institute of Medical and Experimental Virology, Frankfurt Germany. Cells were maintained in RPMI 1640, 10% FCS, 1% L-glutamine, 1% pen-strep and were passage with trypsin EDTA.

Vero cell line was derived from green monkey kidney cells, and is used as host to the MV (obtained from Dr. Yonat Shemer-Avni laboratory, Department of Virology and Developmental Genetics, Ben Gurion University). Cells were maintained in DMEM, 10% FCS, 1% L-glutamine, 1% pen-strep and were passage with trypsin EDTA.

Nupharidine Extracts

Semi-purified NUP extract was prepared. *Nuphar lutea* L was used in this work. Nuphar rhizome was oven-dried at 70° C., and ground in a mortar. 10 g of dry rhizome powder was extracted in 100 ml methanol. The mixed slurry was centrifuged (4,000 rpm, 4° C., 30 min). The supernatant was evaporated under reduced pressure. The residue was dissolved in 100 ml of a mixture of 1N HCl and chloroform (1:1, v/v). The mixture was separated on a separatory funnel. The aqueous phase was collected and adjusted to pH 9 by the addition of 25% NH4OH. Precipitate was harvested by centrifugation and dissolved in acidic methanol. The solution was placed on a silica gel column that was developed with a mixture of chloroform/ethyl-acetate/diethylamine (20:1:1, v/v/v). Fractions were monitored to reduce/inhibit NFκB using the NFκB luciferase reporter gene assay. They were then combined and evaporated to dryness under reduced pressure. The residue was dissolved in 50% methanol in water (named henceforth NUP) and used in the following experiments. An NMR spectrum of the NUP mixture was recorded at 27° C. using a DRX 500 or Avance 500 spectrometer (Bruker Instruments, Karlsruhe, Germany). 1H and 13C NMR spectra were measured at 500 MHz and 125 MHz, respectively. The solvent was CD3OD. Two-dimensional COSY, HMQC and HMBC experiments were measured using standard Bruker software and parameter settings (TopSpin).

Cell Viability

Cell viability was measured by the XTT assay (Beit Haemek). The assay is based on the fact that mitochondria of living cells reduce tetrazolium salts into colored formazan compounds. Cells ($3\times10^4$ cells in suspension or $1\times10^4$ attached cells) were incubated in 96-well plates in triplicate and treated with different concentrations of nupharidine for 12-120 hrs. Thereafter 25 µl of XTT solution was added. After 4 h of incubation at 37° C., absorbance was read in ELISA at 450-500 nm. Cell viability was calculated in compared with control cells without NUP.

Acute Infection

Acute infection with MV (obtained from Dr. Yonat Shemer-Avni's laboratory, Department of Virology and Developmental Genetics, Ben Gurion University)—$8\times10^3$/well Vero cells were seeded in a 96 well plate. Cells were infected with MV (diluted 1:2), $1.7\times10^7$ PFU/ml and treated with NUP (non toxic concentration) either 24 h before infection, simultaneously or 24 h after infection in triplicate. After 96 h after seeding the cells XTT was preformed to examine cell survival.

Persistent Infection

L428 cells were infected with the MV IC323-GFP strain at a MOI=0.001-0.1 PFU/cell, in RPMI 1640, and 2% FCS. After 72 hours post infection, dead cells were removed, and the surviving cells were carried in RPMI 1640, 10% FCS, 1% L-glutamine and 1% pen-strep. The attached cells that remained were shown to be persistently infected by fluorescence microscopy and were called L428+MV-GFP.

FACS Analysis $1.5\times10^6$ L428+GFP-MV cells were incubated for 96 h with different concentrations of NUP and at different times from 24 h-96 h with 3 µg/ml of NUP. After incubation the cells were washed once with PBS for 5 minutes, at 1,000 RPM, at 4° C. Samples were fixed in 1% formalin for 1 h at 4° C. GFP intensity which reflects the presence of the virus was determined.

Western Blot Analysis

Cells were treated overnight with different concentrations of NUP, or at the same concentration at different times. They were seeded in 6 well plates with $6\times10^6$ cells per treatment. After incubation cells were washed three times with PBS. Cells were lysed with 150 µl of RIPA lysis buffer (Tris base pH=8.8 1M, NaCl 5M, EGTA pH=8 250 mM, Beta mercaptoethanol, NAF 1M, SDS 10%) containing protease and phosphatase inhibitors (Roche Diagnostics and Santa Cruz Biotechnology, respectively). The cells were left in ice for 30 min, and centrifuged for 30 min at 13,000 RPM at 4° C.; supernatants were collected and kept at –70° C. until examination. Quantification of protein was made using the Bradford method (Bio-Rad) and was measured by ELISA at 590 nm.

Protein extracts (30-50 µg) were separated in 10% SDS PAGE, transferred and blotted onto a nitrocellulose membrane (Scleicher & Schuel). After transfer the membrane was blocked for an hour, with 3% milk powder and TBS-T (Tris base—2.4 gr/L, NaCl—8 gr/L and TWEEN at pH=7.6). Protein bands were detected by primary antibodies that were incubated for overnight, washed three times with TBS-T and incubated for an hour with a secondary peroxidase-linked anti-IgG antibody, washed three times with TBS-T and developed with EZ-ECL (Beit-Haemek, Ill.).

Immunohistochemistry

L428+MV cells were treated with different concentrations of NUP and incubated for 12 h or 24 h respectively, at 37° C. The cells were cytocentrifuged at 900 rpm for 5 min and fixed in 10% formalin overnight. Samples were stained with anti-P-protein and N-protein primary antibodies (the same antibodies used in the western blot analysis) then with an anti-mouse IgG-peroxidase-linked secondary antibody, and detected by the ABC-Vectastin immunoperoxidase method (Vector laboratories) (positive staying is brown), the nuclei were counterstained with hematoxilin blue.

Example 13

Determination of NUP Non-Toxic Concentration

Figure 14A:
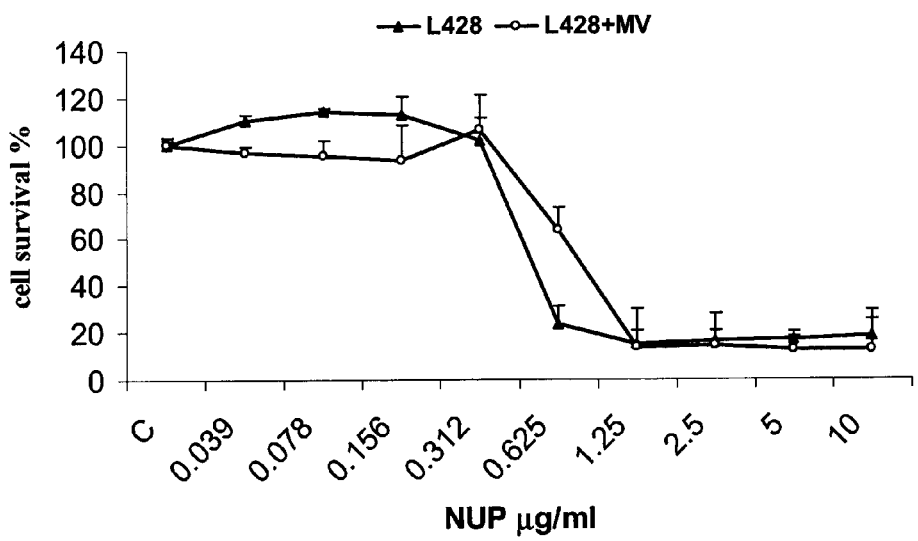
FIG. 14 depicts two survival graphs of cell incubated with double dilutions of NUP for 2 or 5 days. L428 cells in (A) and Vero cells in (B). Cell survival was examined by XTT. No significant difference in NUP cytotoxicity was observed between L428 cells and L428+MV.
Figure 14B:
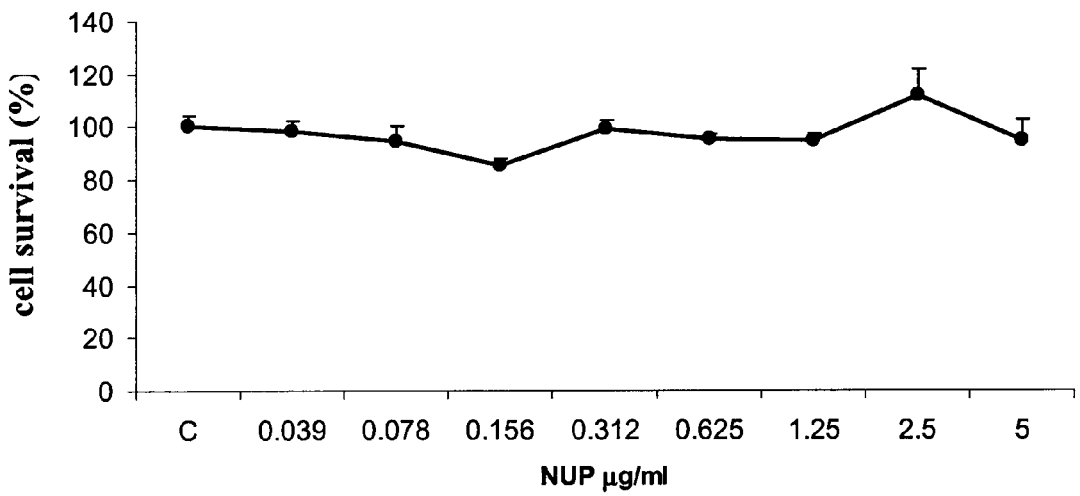

In this study the antiviral properties of NUP were examined. Cytotoxicity was tested on L428, L428-MV (FIG. 14A) both cells show similar sensitivity to NUP. Non cytotoxic concentrations of NUP were determined on VERO cells to treat these cells upon acute MV infection. (FIG. 14B). Toxicity was determined by XTT. No significant difference in NUP cytotoxicity was observed between L428 cells and L428+MV. The significance of these results is that cells can be exposed to effective anti-viral concentrations of NUP, without potentially toxic effects.

Example 14

The Effect of NUP on MV Acute Infection

Figure 15A:
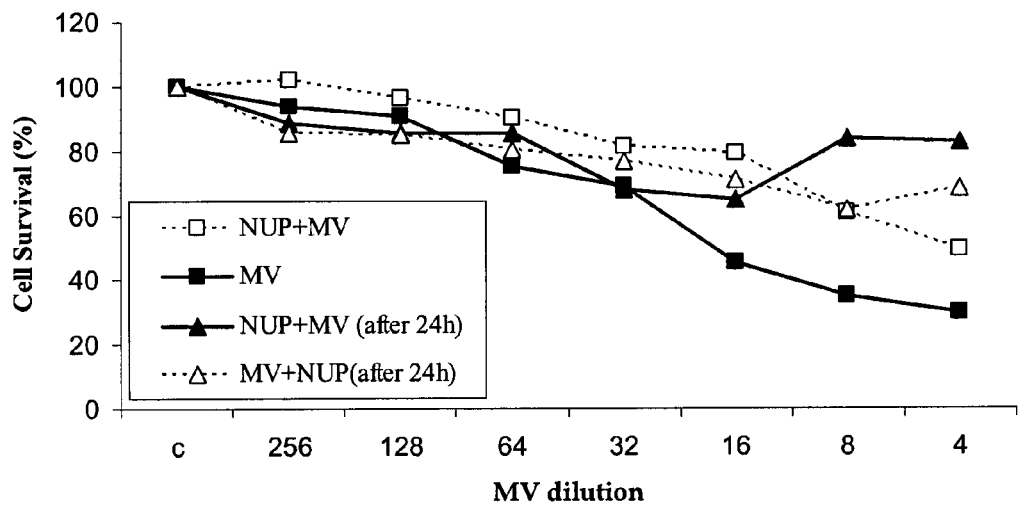
FIG. 15 depicts two graphs. (A) Vero cells were infected with double dilutions of MV. Stock: 1.7×10$^7$ PFU/ml and treated with NUP at 0.3 µg/ml, either 24 h before infection, simultaneously or 24 h after infection. After 72 h the cytopatic effect was observed, and cell survival determined by XTT 96 h after the cells were seeded as shown. (B) is a bar graph of the controls used in this experiment: Vero cells incubated only with medium (1); methanol 50% (vehicle) (2); or 0.3 µg/ml NUP (3); or with 1:1 Measles Virus (MV) dilution and 50% methanol (4).
Figure 20A:
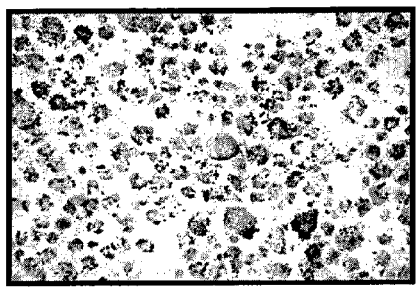
FIG. 20 depicts immunohistochemical micrographs of L428+MV cells. The cells were incubated for 12 h without NUP as control positive staining with the anti-P antibody (A-B, magnification of 400× and 100×, respectively) or treated with 12 mg/ml NUP (AG911 fraction) (C, D magnification of 400× and 100×, respectively). The same cells were incubated with anti-N antibodies (400×): Untreated cells (E), cells treated with 0.75 mg/ml NUP (F) or 1.5 mg/ml NUP (G)
Figure 20B:
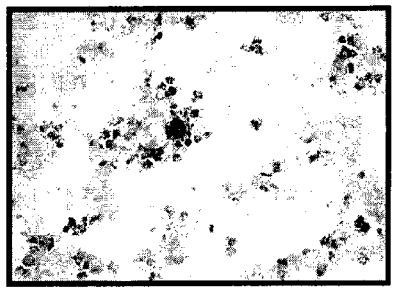
Figure 20C:
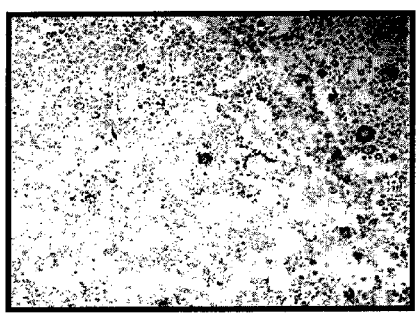
Figure 20D:
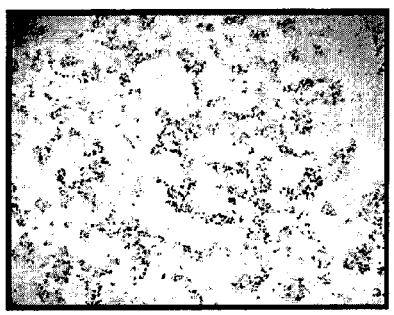
Figure 20E:
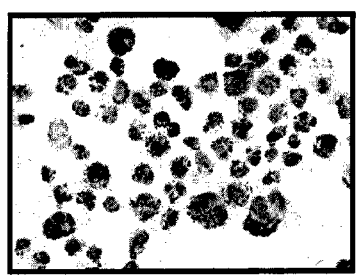
Figure 20F:
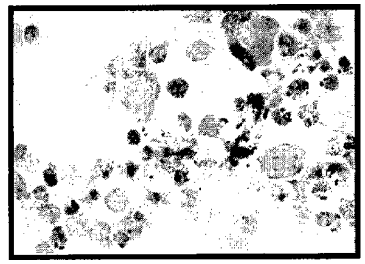
Figure 20G:
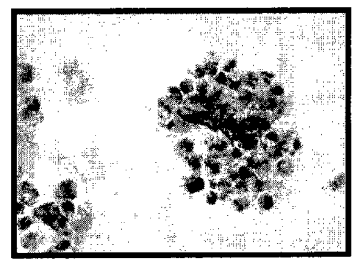

To determine whether NUP can protect cells from MV acute infection, cells were treated (non toxic concentration) either before infection, simultaneously or after infection. Since MV induces a cytopatic effect that kills cells, cell survival was examined by XTT. The results demonstrated that NUP protects cells from MV cytotoxicity as compared with cells that were infected with MV alone (FIG. 15A) and not exposed to NUP. The most significant effect was observed when cells were pretreated with Nupharidine followed by MV infection after 24 h. For controls, Vero cells were incubated only with medium, methanol 50% (vehicle), or only with NUP, all control cells show 100% survival (FIG. 15B). Thus, NUP is effective both in: (1) protecting cells not infected by MV against MV infection for at least 24 hours by dramatically reducing/inhibiting cytotoxicity induced by MV; and (2) against cell cytotoxicity in cells already infected by MV. These results demonstrate that treatment with NUP can limit and/or protect cells from damage by the virus, suggesting a therapeutic effect in cases where patients are already infected or as a preventive agent in epidemics or in populations that are not vaccinated.

Example 15

NUP Treatment Reduces the Amount of MV in Persistently Infected Cells

As shown above, NUP has an impressive protective effect on MV acutely infected cells. To examine the ability of NUP to reduce the amount of viral particles, the effect of NUP on the L428+MV-GFP cells (FIG. 16) was examined by FACS analysis (FIG. 17). Cells were incubated either with different concentrations of NUP for 96 h, or at different time points with 3 µg/ml NUP. A dose dependent and time dependent reduction in GFP intensity was observed (FIG. 17). These results demonstrate that NUP can be effective not only in cases of acute infection but also in rare but fatal cases were the virus persists long after the acute infection has been resolved. In addition it was demonstrated that in the experimental system where cells are persistently infected with the virus it is very useful in dissecting the mechanism of NUP action.

Example 16

The Effect of NUP on an Anti-Viral Protein

The next step was to examine whether NUP affects the expression of viral proteins. To examine this effect a persistently MV infected cell culture was created (FIG. 18). The expression of proteins involved in viral transcription, replication and pathogenesis, the N-protein, P-protein and the V-protein were examined by western blot and immunohistochemistry. A decrease in N-protein and V-protein expression was observed. Moreover, P-protein expression was completely inhibited (FIG. 19 and FIG. 20). To determine whether the antiviral effect of NUP is specific to L428, its effect on the UKF+MV was also examined (FIG. 19C). These results show that NUP acts differentially against different viral proteins. It abrogates the expression of P and diminishes the expression of N and V. The results are the basis of the understanding of NUP's mode of action.

Example 17

The Effect of NUP on the Host Cell Proteins

One of the mechanisms by which the MV suppresses inflammation is by the activation of the Ubiquitin modifying enzyme-A20 by the viral P-protein. The P-protein indirectly interacts with the ELIE motif of A20, and releases the repression of A20 transcription. Following the present results that NUP completely inhibits P-protein expression, the effect of NUP on A20 was also examined. A strong decrease in A20 expression was observed in the L428+MV cells that were incubated with different NUP concentrations (FIG. 21). Non-infected L428 express less A20 basal levels than the infected cells. Thus, NUP contradicts the anti-inflammatory mechanism induced by MV via Ubiquitin modifying enzyme-A20. This phenomenon is apparent 12 h after incubation in concentration of 0.4-6 µg/ml NUP. The effect of NUP was tested on a host protein (A20) which can be modulated by the MV. Viral infection and its successful resolution depend on the host/parasite interaction of viral and host proteins. NUP modulates not only the expression of viral proteins but also the expression of host (cellular) proteins which may directly or indirectly interact with the virus. The anti-viral effect of NUP depends on the modulation of both interdependent arms for the benefit of the host.

Thus the results presented herein demonstrate that NUP protects MV acutely infected cells from cytopatic effect, most significantly by NUP pretreatment 24 hours before infection but also when treated simultaneously with the virus or 24 hours after infection. GFP-MV fluorescence as measured by FACS was also diminished in L428-GFP-MV persistently infected cells suggesting a decrease in the number of viral particles inside the cells. Western blots demonstrated an almost complete elimination of the MV P-protein and the decrease of N-protein and V-protein upon treatment in L428-MV cells and P-protein elimination and N-protein reduction in UKF-NB-MV cells, indicating the effect of NUP is not cell-type restricted.

NUP affected also host proteins which are modulated by MV. A20 is downregulated in treated cells. MV-infected cells express more A20 than non-infected cells.

Example 18

Anti-Viral Effect of NUP

Figure 30A:
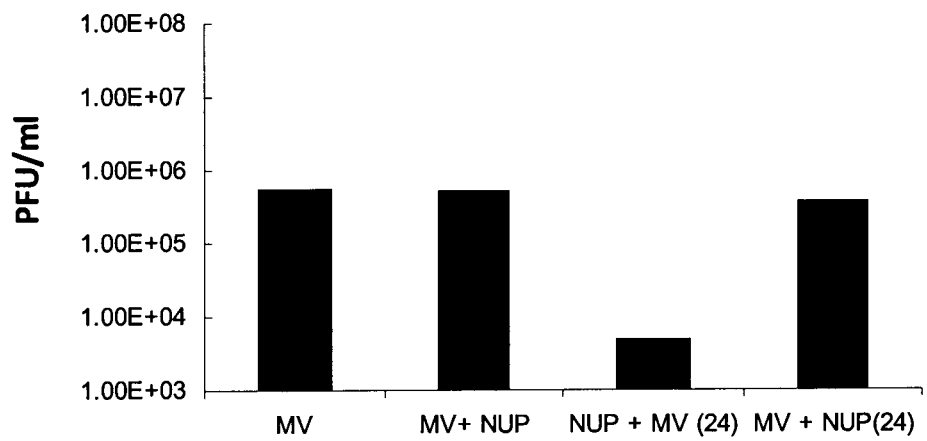
FIG. 30 describes the determination of infective virus (PFU/ml) released from NUP treated cells, NUP reduced significantly the amount of infective particles released in the supernatant (A) and in cells (B).
Figure 30B:
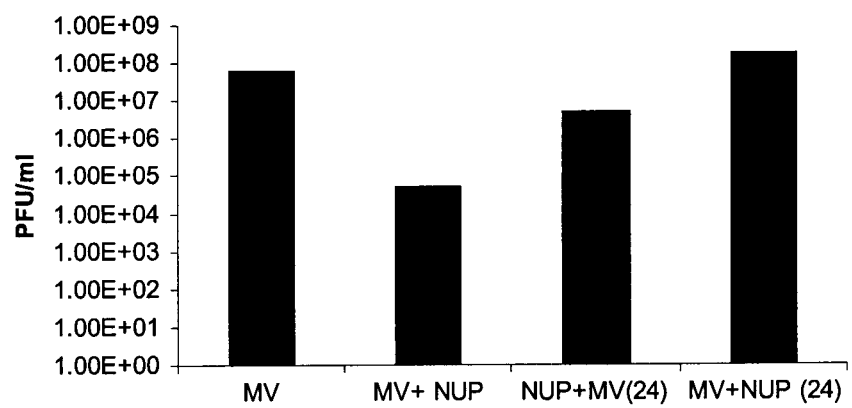
Figure 31A:
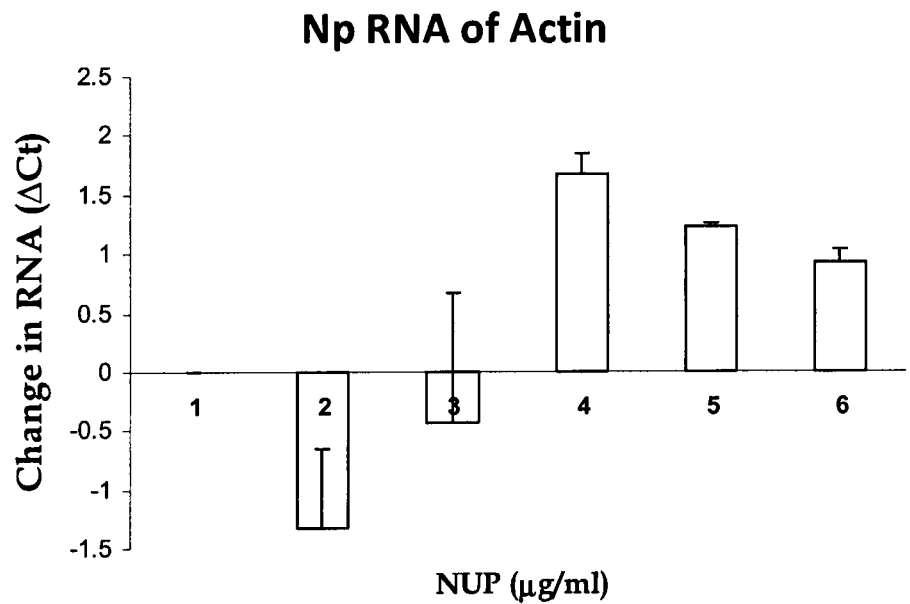
FIG. 31 shows MV RNA determination by Real-Time RT-PCR (qRT-PCR). Actin RNA (31A and 31B) was used to compare and measure changes in the expression of the N and P RNA's (31C and 31D respectively) following treatment with NUP. No significant differences were observed in the expression of N or P in treated cells as compared to controls.
Figure 31B:
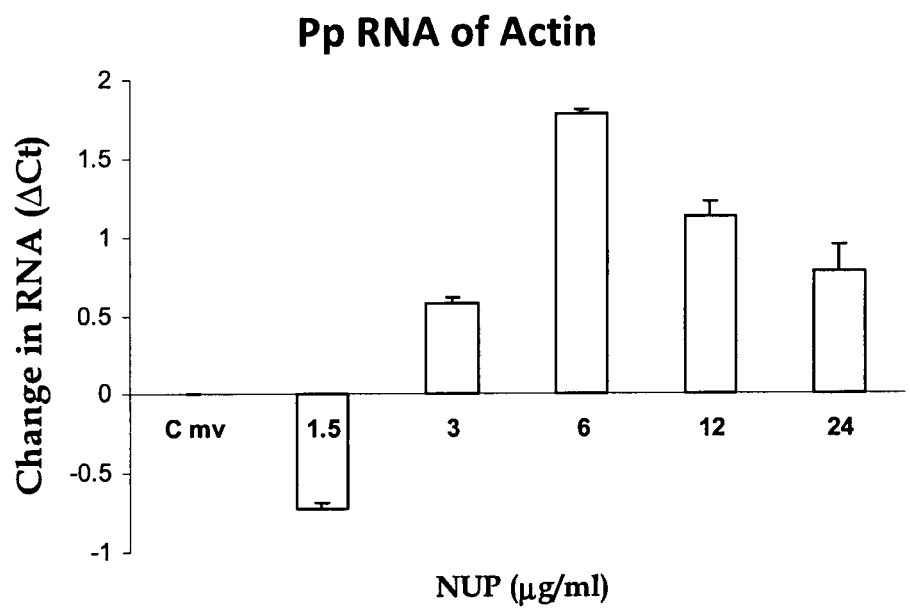
Figure 31C:
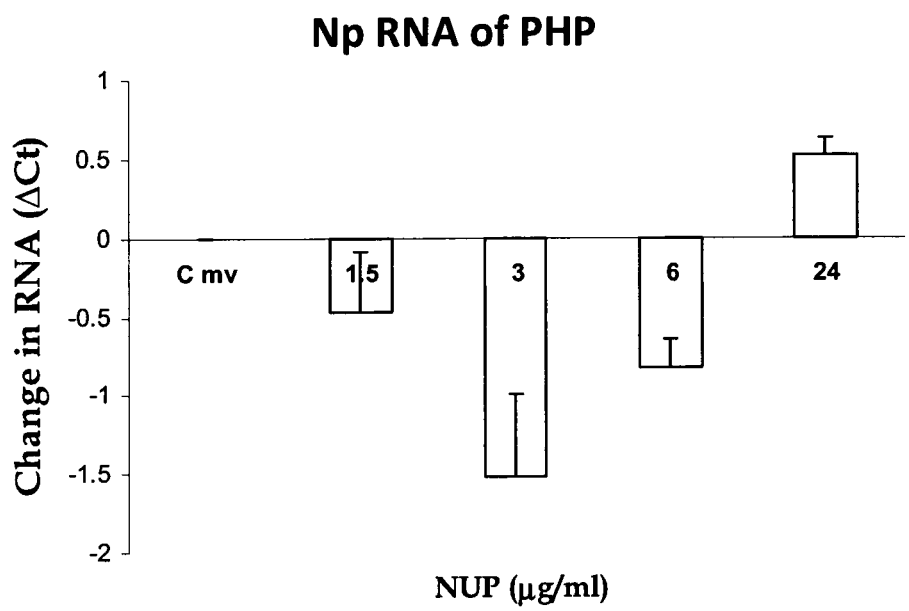
Figure 31D:
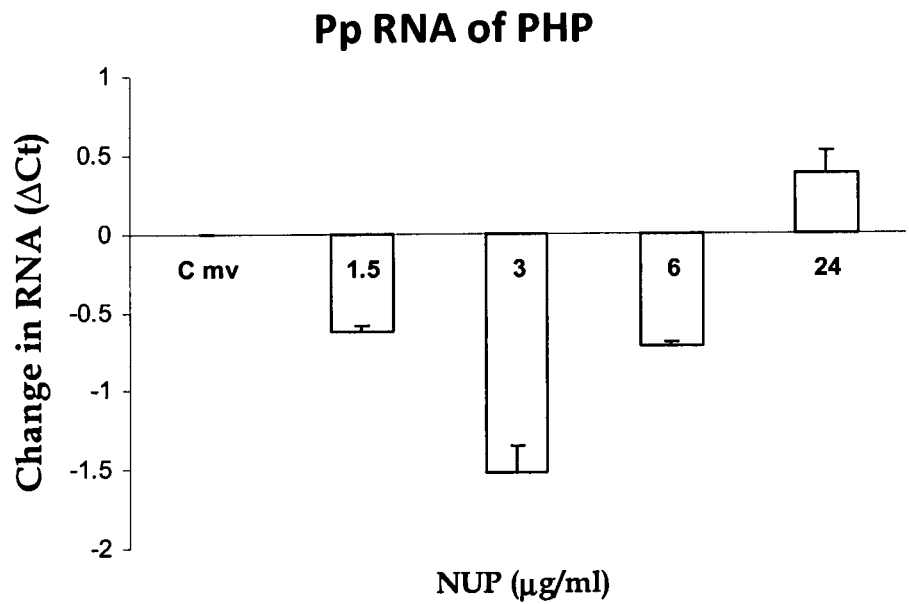

The amount of infective virus released to the medium (PFU/ml) in NUP treated or untreated cells was titrated. VERO-SLAM cells (expressing the SLAM receptor necessary for infection by wild type measles) were infected with the MV wild type GFP labeled IC323-GFP strain obtained by Dr. Yanagi, Japan. 96 h post infection, supernatants and cell lysates were collected and ten-fold dilutions were applied to uninfected VERO-SLAM cells. Fluorescence (virus presence) was scored through a fluorescence microscope after 96 h. PFU/ml was determined as described in materials and methods:

$5*10^4$ VERO SLAM cells per ml were seeded in triplicate, in 24-well plates. Four different NUP treatment combinations were tested: a. The cells were infected with $1.7*10^6$ PFU/ml of the wild type MV IC323-GFP strain and vehicle but without NUP b. Infection with the virus and 24 h later NUP (non-toxic concentration) c. Simultaneous addition of NUP with the virus d. 24 h pretreatment with NUP followed by viral infection. The cells were incubated at 37° C. and supernatants or frozen and thawed cell lysates were collected for 4 days post-infection. Ten fold dilutions of the supernatants or lysates were added to Vero-SLAM cells seeded in 96 wells ($8*10^4$/well), six wells per treatment (one individual plate). Viral infection in each well was determined by GFP fluorescence under a fluorescent microscope. The virus quantification was determined by TCID50. Positive viral presence was defined as detection of GFP viral fluorescence in the highest dilution of sup/lysate in 50% of the duplicate wells (at least 3 out of 6 wells) The calculation was performed according to the method of Reed and Muench as follows:

1. $\dfrac{(\% \text{ positive above } 50\%) - 50\%}{(\% \text{ positive above } 50\%) - (\% \text{ positive below } 50\%)} =$ proportionate distance 2. (log dilution above 50%) + (proportionate distance $X$ log dilution factor) = log $ID_{50}$ 3. $\dfrac{10^{ID50}}{\text{Infection volume}} = \dfrac{PFU}{ml}$ As can be seen from FIG. 30, which describes the determination of infective virus (PFU/ml) released from NUP treated cells, NUP reduced significantly the amount of infective particles released in the supernatant (FIG. 30A) and in cells (FIG. 30B).

Example 19

MV RNA Determination by Real-Time RT-PCR (qRT-PCR)

This experiment tested whether NUP reduces N and P RNA. qRT-PCR was performed. L428+MV cells were incubated with different concentration of NUP for 12 hrs. After incubation, total RNA isolation and qRT-PCR were preformed. MV primers and probes were against N and P protein, human β-actin and PHP genes were used for normalization. After normalization of N or P cycles with either β-actin or PHP, the control values were subtracted from the values of the normalized NUP-treated samples (ΔCt).

Total RNA was isolated from 6*10⁶ L428+MV and control L428 cells incubated with different concentration of Nup for 12 hrs. RNA was obtained with the EZ-RNA 2 kit (Beit-Haemek, Israel). RNA concentration and purity were determined by Nano Drop spectrometry 260/280 nm.

Real-time RT-PCR was performed with the AgPath-ID™ one-step kit (Applied Biosystems-AB, USA), which contains the reverse transcriptase and the Taq-man polymerase enzymes.

Primers and probes were against the N and P cDNA of MV.

Primers against the N (Metabion, Germany), stock concentration used was 10 µM:

Forward-    5'- TCA GTA GAG CGG TTG GAC CC-3' final concentration per sample 125 nM.

Reverse-    5'- GGC CCG GTT TCT CTG TAG CT -3' final concentration per sample 250 nM.

Primers against the P (Metabion, Germany), stock concentration used was 10)µM:

Forward-    5'- AGC TCA GCC GTC GGG TTT-3' final concentration per sample 125 nM.

Reverse-    5'- CCT CTA GCC GGC TGG ATT TT-3' final concentration per sample 250 nM.

Probe against N (IDT—Integrated DNA Technologies, Germany), stock concentration used was 5 µM:

5'- 56-ROX- CAA ACA GAG TCG AGG AGA AGC

CAG GGA- 3BHQ_2-3' final concentration per sample 75 nM.

Probe against P (from Applied Biosystems, USA), stock concentration used was 5 µM:

5'-VIC- CCGGCCCTGCATC-3' final concentration per sample 75 nM.

For normalization we used the primers and probes of both β-actin and PHP (Panhypopituitarism) genes.

For β-actin we used Taq-Man Gene Expression Master Mix kit (Applied Biosystems, USA), final concentration of primers—900 nM, and probe—250 nM.

PHP primers were obtained from TIB Molbiol, Germany:

Forward-  5'- CAT GGG AAG CAA GGG AAC TAA TG-3' final concentration per sample 900 nM.

Reverse-  5'- CCC AGC GAG CAA TAC AGA ATT T-3' final concentration per sample 900 nM.

Probe-
5'-Cy5 TCT TCC CTC GAA CCT GCA CCA TCA AT-3' final concentration per sample 225 nM.

The final concentration of samples was 50 ng/µl (stock). Samples were diluted 1:100 in DEPC water, from this dilution 2 µl of RNA were used for qRT-PCR analysis; the final volume of sample was 20 µl.

Real-Time-RT-PCR Program

Step 1—30 min in 50° C.→10 min in 95° C.→15 sec in 95° C.

Step 2—32 sec in 55° C. for every cycle, for a total of 40 cycles.

The results were normalized to β-actin and PHP of control untreated L428+MV cells.

The experiment was repeated two times.

This experiment was designed to determine whether or not NUP reduces the amounts of virus by inhibiting the expression of viral RNA. The results show (FIG. 31A-D) that no significant difference was detected in the levels of viral RNA tested between treated and untreated persistently infected cells. The conclusion thus, is that NUP does not regulate the expression of the measles viral protein tested at the transcriptional level, therefore the decrease in viral proteins (mainly P) is not due to the decrease in its RNA but most likely due to induction of protein degradation or reduced translation.

RSV

Materials and Methods

Antibodies: Monoclonal antibodies: Anti-N protein RSV (ABM, Richmond, Canada), Anti-actin (MP Biomedical, Aurora, Ohio), Polyclonal antibodies: Peroxidase linked Donkey anti rabbit IgG (Jackson ImmunoResearch, West Grove, Pa.), Peroxidase linked rabbit anti mouse IgG (Jackson ImmunoResearch, West Grove, Pa.)

Growth Medium

RPMI 1640 and DMEM (Beit Haemek, Israel), 10% fetal bovine serum (FCS) (Beit Haemek, Israel), 1% L-glutamine (Beit Haemek, Israel), 1% pen-strep (Beit Haemek, Israel), Trypsin EDTA (Beit Haemek, Israel), Cell Lines, and Viruses Hep-2 Cells The Hep-2 cell line was derived from human transformed laryngeal carcinoma, and is used as hosts to RSV. The cells were maintained in DMEM, 10% FCS, 1% L-glutamine, 1% pen-strep and were passage with trypsin EDTA. These cells were persistently infected with the RSV strain A.

Nupharidine Extracts

Semi-purified NUP extract was prepared. *Nuphar lutea* L. was used in this work. *Nuphar* rhizome was oven-dried at 70° C., and ground in a mortar. 10 g of dry rhizome powder was extracted in 100 ml methanol. The mixed slurry was centrifuged (4,000 rpm, 4° C., 30 min). The supernatant was evaporated under reduced pressure. The residue was dissolved in 100 ml of a mixture of 1N HCl and chloroform (1:1, v/v). The mixture was separated on a separatory funnel. The aqueous phase was collected and adjusted to pH 9 by the addition of 25% NH4OH. Precipitate was harvested by centrifugation and dissolved in acidic methanol. The solution was placed on a silica gel column that was developed with a mixture of chloroform/ethyl-acetate/diethylamine (20:1:1, v/v/v). Fractions were monitored to reduce/inhibit NFκB using the NFκB luciferase reporter gene assay. They were then combined and evaporated to dryness under reduced pressure. The residue was dissolved in 50% methanol in water (named henceforth NUP) and used in the following experiments. An NMR spectrum of the NUP mixture was recorded at 27° C. using a DRX 500 or Avance 500 spectrometer (Bruker Instruments, Karlsruhe, Germany). 1H and 13C NMR spectra were measured at 500 MHz and 125 MHz, respectively. The solvent was CD3OD. Two-dimensional COSY, HMQC and HMBC experiments were measured using standard Bruker software and parameter settings (TopSpin).

Cell Viability-XTT

Cell cytotoxicity was measured by the XTT assay (Beit Haemek) described above in the example related to measles.

Acute Infection

Acute infection with RSV (obtained from Dr. Yonat Shemer-Avni Virology and Developmental Genetics laboratory, Faculty of Health Sciences, Ben Gurion University, Beer Sheva, Israel)—$8\times10^3$ Hep-2 cells were seeded in a 96 well plate. Cells were infected with RSV (diluted 1:10 from stock) $4.7\times10^8$ PFU/ml and treated with nupharidine (non toxic concentration) either 2 h before infection, simultaneously or 2 h after infection. The presence or absence of cyncitia was scored for 3-5 days with light microscope and photos were taken.

Persistent Infection

Hep-2 cell were infected with RSV strain A at a multiplicity of infection MOI=1 PFU/cell in DMEM and 2% FCS. After 72 hrs post-infection dead cells were removed, and the surviving cells were carried in DMEM medium and 10% FCS. Cells that remained attached were shown to be persistently infected by immuno-fluorescence (the kit) in confocal microscopy and were termed Hep-2+RSV.

Western Blot Analysis

Cell Lysates

Cells were treated with different concentrations of NUP for overnight, or at the same concentration at different time. They were seeded in 6 well plates with $6\times10^6$ cells per treatment. After incubation cells were washed three times with PBS. Cells were lysed with 150 µl of RIPA lysis buffer (Tris base pH=8.8 1M, NaCl 5M, EGTA pH=8 250 mM, Beta mercaptoethanol, NAF 1M, SDS 10%) containing protease and phosphatase inhibitors (Roche Diagnostics and Santa Cruz Biotechnology, respectively). The cells were left at ice for 30 min, and centrifuged for 30 min at 13,000 RPM at 4° C., the supernatant was collected and kept at −70° C. until examination. Quantification of protein was made using the Bradford method (Bio-Rad) and was measured by ELISA at 590 nm.

SDS PAGE: Western Blot Analysis

Protein extracts (30-50 µg) were separated in 10% SDS PAGE, transferred and blotted onto a nitrocellulose membrane (Scleicher & Schuel). After transfer the membrane was blocked for an hour, with 3% milk powder and TBS-T (Tris base—2.4 gr/L, NaCl—8 gr/L and TWEEN at pH=7.6). Protein bands were detected by primary antibodies that were incubated for overnight, washed three times with TBS-T and incubated for an hour with a secondary peroxidase-linked anti-IgG antibody, washed three times with TBS-T and developed with EZ-ECL (Beit-Haemek).

Immunohistochemistry

Hep-2+RSV cells were treated with different concentrations of NUP and incubated for 12 h or 24 h respectively, at 37° C. The cells were cytocentrifuged at 900 rpm for 5 min and fixed in 10% formalin overnight. Slides were stained with anti-N-protein primary antibody then followed by anti-mouse IgG-peroxidase-linked secondary antibody, and detected by the ABC-Vectastin immunoperoxidase method (Vector laboratories) (positive staying is brown), the nuclei were counterstained with hematoxilin (blue).

Example 20

Determination of NUP Non-Toxic Concentration

In this study the antiviral properties of NUP were examined. Cytotoxicity was tested on Hep-2 cells which were used for acute and persistent infections (FIG. 1). Toxicity was examined through XTT analysis and cell survival was expressed as the proportion of cells alive compared to cells incubated with vehicle only (50% methanol).

Example 21

The Effect of NUP on RSV Acute Infection

To see if NUP can protect cells from acute infection by the viruses, the cells were treated with NUP (non toxic concentration) either before infection, simultaneously or after infection. The effect of NUP on RSV infection was observed by the presences of cyncitia. 5 days after infection, syncitia was observed mainly in cells infected with RSV and untreated by NUP. In contrast, in cells treated with NUP the amount of cyncitia was low and almost undetectable (FIG. 22). Thus, NUP unexpectedly protects cells from infection and at the same time inhibits contagiousness of a subject exposed to RSV. Therefore, NUP treatment is effective in inhibiting RSV epidemics.

Example 22

The Effect of NUP on Anti-Viral Proteins

The next step was to examine how NUP affects the virus proteins. To examine this effect persistently infected cells with RSV were created (FIG. 23). Proteins involved in viral transcription, replication and pathogenesis, the N-protein, P-protein and the V-protein were examined by western blot and immunohistochemistry analysis.

This work demonstrates that NUP exert unexpected anti-RSV effect on Hep-2 cells both acutely and persistently infected. NUP is effective for actual treatment as the concentrations and incubation times utilized were not cytotoxic. Treatment with NUP effectively inhibited the formation of syncitia in acutely infected cells. It is shown that NUP acts differentially against different viral proteins. Moreover, these results demonstrate that treatment with NUP can limit and/or protect cells from damage by the virus, suggesting a therapeutic effect in cases where patients are already infected or as a preventive agent in epidemics or in populations that are not vaccinated. These results also demonstrate that NUP can be effective not only in cases of acute infection but also in rare but fatal cases were the virus persists long after the acute infection has been resolved. In addition it was demonstrated that in the experimental system where cells are persistently infected with the virus it is very useful in dissecting the mechanism of NUP action.

Thus these results show that NUP is effective in: (1) treating a subject infected with RSV by inhibiting the spread of the virus to nearby cells; and (2) a preventive measure against RSV infection and epidemics particularly in populations susceptible to RSV complications such as infants.

Example 23

The mechanism of action of NUP was investigated in by western blot with antibodies against ERK and IKK. L428 cells were incubated with NUP: NUP inhibits NF-kB activity but also influences other pathways such as ERK. In addition, treatment with NUP diminishes the expression of IKK, which phosphorylates IkB and induces its ubiquitinization and release of NF-kB from the cytoplasm to the nucleus.

Figure 28A:
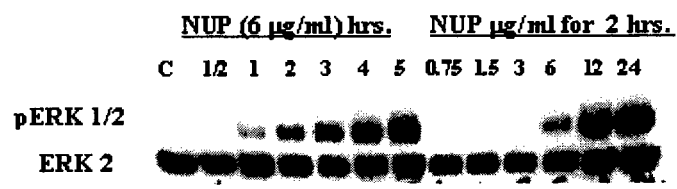
FIG. 28 (A) shows that NUP induces ERK phosphorylation (dose and time dependency); and (B) reduces the expression of IKKabeta but not IKKalphain 1428 cells.
Figure 28B:
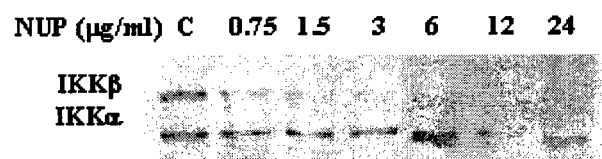
Figure 29:
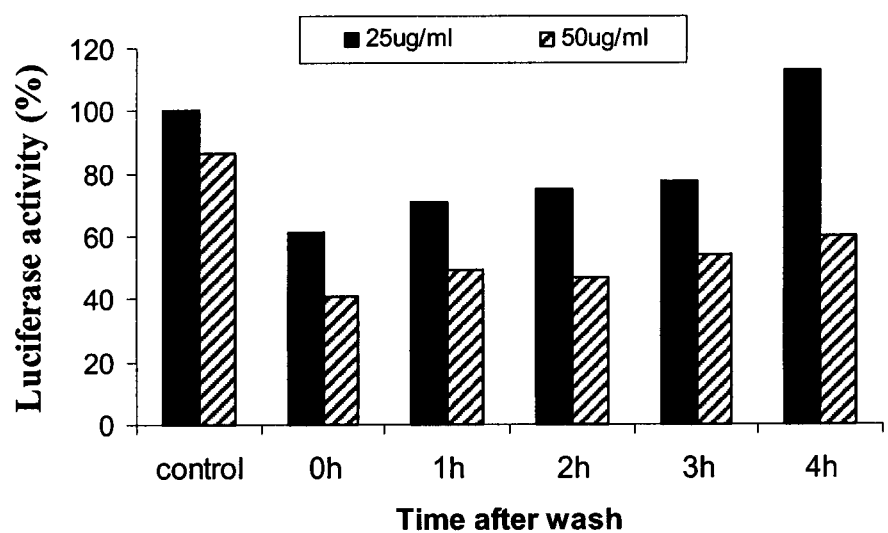
FIG. 29 shows the results of a NF-kB luciferase reporter gene assay. L428 cells expressing stable NFkB-luc plasmid were treated with different NUP concentrations. Luciferase activity was measured at several time points. At lower NUP concentration 25 µg/ml, the full recovery of luciferace activity was seen after 4 h (grey bars). At higher NUP concentration, 50 µg/ml (black bars) the recovery was much slower and not complete at the tested time points.

As can be seen from FIG. 28A. NUP induces ERK phosphorylation (dose and time dependency). FIG. 28B demonstrates that NUP reduces the expression of IKKabeta but not IKKalphain 1428 cells In order to determine whether or not the downregulation of NF-κB by NUP is reversible, a NF-κB luciferase reporter gene assay was preformed. L428 cells expressing stable NFκB-luc plasmid were treated with different NUP concentrations (25 and 50 μg/ml). After 2 h incubation with NUP the cells were washed with PBS and the medium was replaced. Luciferase activity was measured at several time points. As can be seen from FIG. 29, at lower NUP concentration the full recovery of luciferace activity was seen after 4 h (grey bars). At higher NUP concentration (black bars) the recovery was much slower and not complete at tested time points. These results indicate that NUP effect is dose dependent and transient. In order to achieve long term inhibition of NF-κB the treatment should be given continuously.

What is claimed is:

1. A method for treating a subject afflicted with Hodgkin lymphoma, melanoma, or lung melanoma, comprising administering to said subject a) a compound of Formula (I) or (II), a composition comprising a fraction of a Nymphaeaceae extract comprising a compound of Formula (I) and a compound of Formula (II); or a combination of the compound of Formula (I) and the compound of Formula (II)

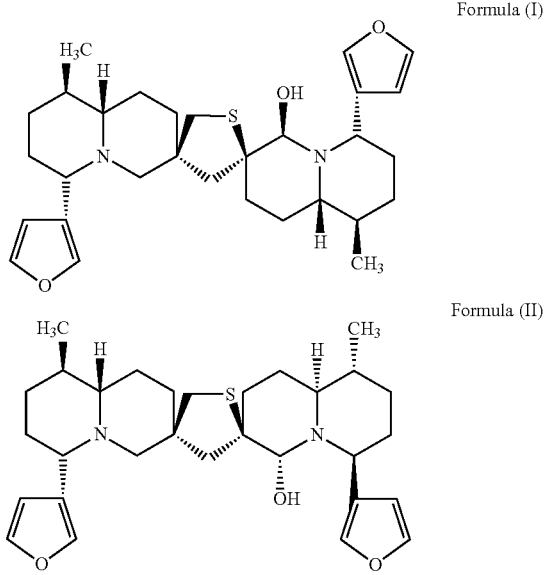

and; b) a composition comprising podophyllotoxin drug or platinum drug.

2. The method of claim 1, wherein said podophyllotoxin drug is etoposide.

3. The method of claim 1, wherein said platinum drug is cisplatin.

4. The method of claim 1, wherein said Nymphaeaceae is Nuphar lutea.

5. A method for treating cancer in a subject in need thereof, comprising administering to said subject a) a compound of Formula (I) or (II), a composition comprising a fraction of a Nymphaeaceae extract, comprising a compound of Formula (I) and a compound of Formula (II); or a combination of the compound of Formula (I) and the compound of Formula (II)

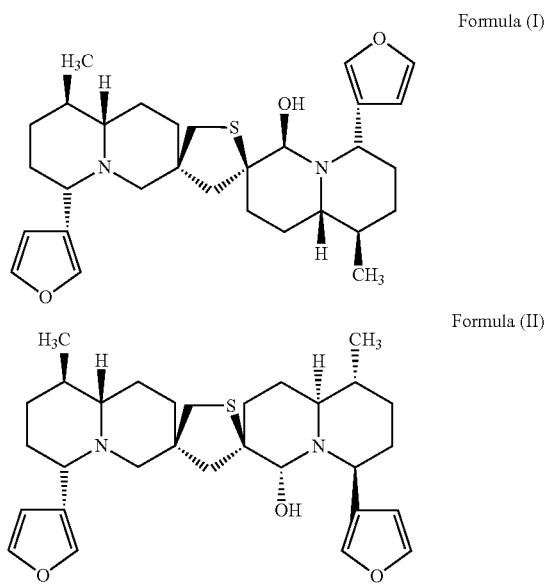

and; b) a composition comprising podophyllotoxin drug or platinum drug.

6. The method of claim 5, wherein said podophyllotoxin drug is etoposide.

7. The method of claim 5, wherein said platinum drug is cisplatin.

8. The method of claim 5, wherein said Nymphaeaceae is Nuphar lutea.

9. A method for reducing or treating an inflammation disease in a subject in need thereof, comprising administering to said subject a compound of Formula (I) or (II), a composition comprising a a fraction of a Nymphaeaceae extract comprising a compound of Formula (I) and a compound of Formula (II) ; or a combination of the compound of Formula (I) and the compound of Formula (II).

10. The method of claim 9, wherein said reducing or treating inflammation disease is affected by reducing pro-inflammatory cytokines and elevating anti-inflammatory cytokine in the blood of said subject.

11. The method of claim 9, wherein said inflammation disease is inflammatory bowel disease (IBD), ulcerative colitis (UC) or Crohn's disease (CD).

12. The method of claim 9, wherein said Nymphaeaceae is Nuphar lutea.

13. A method for treating a subject afflicted with Respiratory Syncytial Virus, comprising administering to said subject a compound of Formula (I) or (II), a composition comprising a fraction of a Nymphaeaceae extract comprising a compound of Formula (I) and a compound of Formula (II); or a combination of the compound of Formula (I) and the compound of Formula (II).

14. The method of claim 13, wherein said Nymphaeaceae is Nuphar lutea.

15. A method for reducing a cytotoxic effect of a Respiratory Syncytial Virus in a subject, comprising administering to said subject a compound of Formula (I) or (II), a composition comprising a fraction of a Nymphaeaceae extract comprising a compound of Formula (I) and a compound of Formula (II) (NUP),; or a combination of the compound of Formula (I) and the compound of Formula (II).

16. A method of reducing the contagiousness of a subject infected by a Respiratory Syncytial Virus, comprising administering to said subject a compound of Formula (I) or (II), a composition comprising a fraction of a Nymphaeaceae extract comprising a compound of Formula (I) and a compound of Formula (II), or a combination of the compound of Formula (I) and the compound of Formula (II).

17. A method of reducing a cytotoxic effect of a Respiratory Syncytial Virus in a cell, comprising contacting said cell with a compound of Formula (I) or (II), a composition comprising a fraction of a Nymphaeaceae extract comprising a compound of Formula (I) and a compound of Formula (II) (NUP); or a combination of the compound of Formula (I) and the compound of Formula (II).

\* \* \* \* \*